US012780895B2

(12) United States Patent
Cathomen et al.

(10) Patent No.: US 12,780,895 B2
(45) Date of Patent: Nov. 3, 2026

(54) CHIMERIC ANTIGEN RECEPTORS THAT BIND TO PROSTATE SPECIFIC MEMBRANE ANTIGEN

(71) Applicant: Albert-Ludwigs-Universitaet Freiburg, Freiburg (DE)

(72) Inventors: Toni Cathomen, Freiburg (DE); Jamal Alzubi, Freiburg (DE); Viviane Dettmer, Freiburg (DE); Philipp Wolf, Sexau (DE); Susanne Schultze-Seemann, Merzhausen (DE); Irina Kuckuck, Freiburg (DE); Hinrich Abken, Geiselhoering (DE); Johannes Kuehle, Cologne (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 1180 days.

(21) Appl. No.: 17/255,546

(22) PCT Filed: Jun. 17, 2019

(86) PCT No.: PCT/EP2019/065822
§ 371 (c)(1),
(2) Date: Dec. 23, 2020

(87) PCT Pub. No.: WO2020/002015
PCT Pub. Date: Jan. 2, 2020

(65) Prior Publication Data

US 2021/0371491 A1 Dec. 2, 2021

(30) Foreign Application Priority Data

Jun. 27, 2018 (EP) .................................... 18180026

(51) Int. Cl.

| | |
|---|---|
| ***C07K 14/705*** | (2006.01) |
| ***A61K 38/00*** | (2006.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61K 45/06*** | (2006.01) |
| ***A61P 35/00*** | (2006.01) |
| ***C07K 16/30*** | (2006.01) |

(52) U.S. Cl.
CPC .......... *C07K 14/7051* (2013.01); *A61K 40/11* (2025.01); *A61K 40/31* (2025.01); *A61K 40/4276* (2025.01); *A61K 45/06* (2013.01); *A61P 35/00* (2018.01); *C07K 14/70521* (2013.01); *C07K 16/3069* (2013.01); *A61K 38/00* (2013.01); *A61K 2039/505* (2013.01); *A61K 2239/31* (2023.05); *A61K 2239/38* (2023.05); *A61K 2239/58* (2023.05)

(58) Field of Classification Search
CPC ...................... C07K 14/7051; A61K 2039/505
See application file for complete search history.

(56) References Cited

U.S. PATENT DOCUMENTS 8,198,416 B2 * 6/2012 Elsasser-Beile ... A61K 47/6869 530/391.1

FOREIGN PATENT DOCUMENTS

| | | | | |
|---|---|---|---|---|
| EP | 2 363 486 A1 | 9/2011 | | |
| WO | WO 2009/017823 A2 | 2/2009 | | |
| WO | WO-2016126608 A1 * | 8/2016 | ............ | A61K 35/17 |
| WO | WO 2019/232503 A1 | 12/2019 | | |

OTHER PUBLICATIONS

Zhong et. al. Molecular Therapy 18(2):413-420. (2010) (Year: 2010).*
Almagro et. al., Front. Immunol. 2018; 8:1751 (Year: 2018).*
By Rudikoff et al., Proc. Nat'l Acad. Sci. USA, 79:1979-83 (1982) (Year: 1982).*
Brown et al., J. Immunol., 156(9):3285-91 (1996) (Year: 1996).*
Chiu et al., Antibodies, 8(55):1-80. (2019) (Year: 2019).*
Alzubi, J. et al., "A Novel Chimeric Antigen Receptor CAR-T Cell Approach Eliminates Prostate Cancer in a Mouse Tumour Model", *Human Gene Therapy,* vol. 29, No. 12, p. A21 (Dec. 2018).
Junghans, Richard P. et al., "Phase I Trial of Anti-PSMA Designer CAR-T Cells in Prostate Cancer: Possible Role for Interacting Interleukin 2-T Cell Pharmacodynamics as a Determinant of Clinical Response", *The Prostate,* vol. 76, No. 14, pp. 1257-1270 (Oct. 2016).
Ma, Qiangzhong et al., Advanced Generation Anti-Prostate Specific Membrane Antigen Designer T Cells for Prostate Cancer Immunotherapy, *The Prostate,* vol. 74, No. 3, pp. 286-296 (Feb. 2014).
Ma, Qiangzhong et al., "Anti-Prostate Specific Membrane Antigen Designer T Cells for Prostate Cancer Therapy", *The Prostate,* vol. 61, No. 1, pp. 12-25 (Sep. 2004).
Santoro, Stephen P. et al.. "T Cells Bearing a Chimeric Antigen Receptor Against Prostate-Specific Membrane Antigen Mediate Vascular Disruption and Result in Tumor Regression", *Cancer Immunology Research,* vol. 3, No. 1, pp. 68-84 (Jan. 2015).
Wolf, Philipp et al., "Preclinical Evaluation of a Recombinant Anti-Prostate Specific Membrane Antigen Single-Chain Immunotoxin Against Prostate Cancer", *Journal of Immunotherapy,* vol. 33, No. 3, pp. 262-271 (Mar. 2010).

(Continued)

*Primary Examiner* — Julie Wu
*Assistant Examiner* — Francesca Edgingtongiordano
(74) *Attorney, Agent, or Firm* — Smith Patent, LLC; Chalin A. Smith

(57) ABSTRACT

The present invention relates to a novel chimeric antigen receptor (CAR) comprising an antigen-binding fragment which binds specifically to PSMA antigen, and a method of manufacturing high-quality CAR T cell products by transfection and/or transduction of T cells therewith, which allows to eradicate tumors in vivo alone or in combination with pharmaceutical drugs, such chemotherapies, biopharmaceutical drugs, such as antibodies, or small-molecule drugs, such as protein kinase inhibitors.

19 Claims, 28 Drawing Sheets

Specification includes a Sequence Listing.

(56) References Cited

OTHER PUBLICATIONS

Zhong, Xiao-Song et al., “Chimeric Antigen Receptors Combining 4-1BB and CD28 Signaling Domains Augment $PI_3$ kinase / AKT / Bcl-XL Activation and CD8+ T Cell-mediate Tumor Eradication”, *Molecular Therapy,* vol. 18, No. 2, pp. 413-420 (Feb. 2010).

Tobias Deller et al., “Engineering of Humanized PSMA-Directed CAR T Cells for Potent and Specific Elimination of Prostate Cancer Cells”, Cells (2025), 14: 1333.

* cited by examiner

A
CAR41
ΔU3 R U5 EFS scFv (D7) 41BB CD3ζ WPRE ΔU3 R U5
CAR28
ΔU3 R U5 EFS scFv (D7) CD28 CD3ζ WPRE ΔU3 R U5
B
UT
CAR41
48%
CAR28
49%
CAR
CD3
C
UT
Tcm 43%
Tn,scm 47%
Tem 8%
Teff 2%
CAR41
Tcm 35%
Tn,scm 55%
Tem 5%
Teff 5%
CAR28
Tcm 40%
Tn,scm 52%
Tem 6%
Teff 2%
CD62L
CD45RA
D
% T cell subsets
100%
80%
60%
40%
20%
0%
UT
CAR41
CAR28
Teff
Tem
Tcm
Tn, scm A
UT
CAR41
CAR28
Tcm 45%
Tn,scm 46%
Tem 7%
Teff 2%
Tcm 31%
Tn,scm 43%
Tem 13%
Teff 14%
Tcm 6%
Tn,scm 9%
Tem 38%
Teff 47%
CD62L
CD45RA
B
% T cell subsets
Teff
Tem
Tcm
Tn, scm
C
CD223
CD279
CD3
12%
48%
82%
5%
43%
57%
D
% T cell exhaustion
PD-1
LAG3
NS
UT
CAR41
CAR28

Fig.10

```
             1         10        20        30        40        50        60        70        80        90
                                                                                                          CDR-H1
scFv D7      ATG GCC CAG GTG CAG CTT CAA CAG TCT GGC GCG GAG CTG GTC GAG CCC GGT GCT AGC GTT AAG CTG AGT TGT AAG GCG TCC GGC TAC ACA TTT ACC TAC
Frame 1       M   A   Q   V   Q   L   Q   Q   S   G   A   E   L   V   E   P   G   A   S   V   K   L   S   C   K   A   S   G   Y   T   F   T   Y
Complement   TAC CGG GTC CAC GTC GAA GTT GTC AGA CCG CGC CTC GAC CAG CTC GGG CCA CGA TCG CAA TTC GAC TCA ACA TTC CGC AGG CCG ATG TGT AAA TGG ATG
             100       110       120       130       140       150       160       170       180       190

             CDR-H1                                                  CDR-H2
scFv D7      TTC GAT ATC AAT TGG CTG AGA CAA AGG CCT GAA CAG GGC CTG GAA TGG ATC GGC GGA ATC TCT CCC GGA GAT GGG AAT ACA AAT TAT AAC GAG AAC TTC
Frame 1       F   D   I   N   W   L   R   Q   R   P   E   Q   G   L   E   W   I   G   G   I   S   P   G   D   G   N   T   N   Y   N   E   N   F
Complement   AAG CTA TAG TTA ACC GAC TCT GTT TCC GGA CTT GTC CCG GAC CTT ACC TAG CCG CCT TAG AGA GGG CCT CTA CCC TTA TGT TTA ATA TTG CTC TTG AAG
             200       210       220       230       240       250       260       270       280       290

             CDR-H2
scFv D7      AAG GGA AAG GCT ACT CTT ACT ATA GAC AAG TCC AGC ACT ACG GCC TAC ATC CAG CTG TCC CGC CTC ACG AGC GAG GAC AGC GCC GTG TAT TTC TGT GCA
Frame 1       K   G   K   A   T   L   T   I   D   K   S   S   T   T   A   Y   I   Q   L   S   R   L   T   S   E   D   S   A   V   Y   F   C   A
Complement   TTC CCT TTC CGA TGA GAA TGA TAT CTG TTC AGG TCG TGA TGC CGG ATG TAG GTC GAC AGG GCG GAG TGC TCG CTC CTG TCG CGG CAC ATA AAG ACA CGT
             300       310       320       330       340       350       360       370       380       390

                 CDR-H3
scFv D7      AGG GAC GGC AAC TTC CCC TAC TAT GCA ATG GAT TCT TGG GGG CAG GGC ACT TCC GTC ACA GTG AGC TCT GCC AAG ACC ACA CCG AAA CTG GGC GGA GGA
Frame 1       R   D   G   N   F   P   Y   Y   A   M   D   S   W   G   Q   G   T   S   V   T   V   S   S   A   K   T   T   P   K   L   G   G   G
Complement   TCC CTG CCG TTG AAG GGG ATG ATA CGT TAC CTA AGA ACC CCC GTC CCG TGA AGG CAG TGT CAC TCG AGA CGG TTC TGG TGT GGC TTT GAC CCG CCT CCT
             400       410       420       430       440       450       460       470       480       490

scFv D7      GGC AGT GGA GGT GGG GGG AGC GGG GGT GGG GGA AGT GCT CGC GTG GAT ATT GAG CTC ACT CAG AGT CCT CTG TCT CTC CCT GTG ATA CTG GGC GAC CAA
Frame 1       G   S   G   G   G   G   S   G   G   G   G   S   A   R   V   D   I   E   L   T   Q   S   P   L   S   L   P   V   I   L   G   D   Q
Complement   CCG TCA CCT CCA CCC CCC TCG CCC CCA CCC CCT TCA CGA GCG CAC CTA TAA CTC GAG TGA GTC TCA GGA GAC AGA GAG GGA CAC TAT GAC CCG CTG GTT
             500       510       520       530       540       550       560       570       580       590

                     CDR-L1
scFv D7      GCT AGC ATT AGC TGC CGA AGC AGC CAA TCA CTG GTC CAC TCT AAC GGA AAC ACC TAT CTT CAC TGG TTT CTC CAA AAG CCT GGA CAG TCC CCG AAG TTG
Frame 1       A   S   I   S   C   R   S   S   Q   S   L   V   H   S   N   G   N   T   Y   L   H   W   F   L   Q   K   P   G   Q   S   P   K   L
Complement   CGA TCG TAA TCG ACG GCT TCG TCG GTT AGT GAC CAG GTG AGA TTG CCT TTG TGG ATA GAA GTG ACC AAA GAG GTT TTC GGA CCT GTC AGG GGC TTC AAC
             600       610       620       630       640       650       660       670       680       690

                 CDR-L2
scFv D7      CTT ATT TAT ACT GTC AGC AAC CGA TTC TCA GGG GTC CCC GAT CGA TTC AGC GGC AGC GGG AGC GGG ACC GAC TTT ACC CTC AAG ATC TCC CGC GTG GAG
Frame 1       L   I   Y   T   V   S   N   R   F   S   G   V   P   D   R   F   S   G   S   G   S   G   T   D   F   T   L   K   I   S   R   V   E
Complement   GAA TAA ATA TGA CAG TCG TTG GCT AAG AGT CCC CAG GGG CTA GCT AAG TCG CCG TCG CCC TCG CCC TGG CTG AAA TGG GAG TTC TAG AGG GCG CAC CTC
             700       710       720       730       740       750       760       770  777

                                         CDR-L3
scFv D7      GCC GAG GAC CTG GGA GTC TAT TTC TGC AGC CAG TCT ACT CAT GTG CCG ACG TTC GGA GGA GGG ACG AAG TTG GAG ATA AAA AGA
Frame 1       A   E   D   L   G   V   Y   F   C   S   Q   S   T   H   V   P   T   F   G   G   G   T   K   L   E   I   K   R
Complement   CGG CTC CTG GAC CCT CAG ATA AAG ACG TCG GTC AGA TGA GTA CAC GGC TGC AAG CCT CCT CCC TGC TTC AAC CTC TAT TTT TCT
```

Fig. 11

| | | CDR-H1 | | | | | | CDR-H2 | | | | | | | | | | | | | | | | | | CDR-H3 | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| D7 VH murine | murine FR-1 | Y | F | D | I | N | murine FR-2 | G | I | S | P | G | D | G | N | T | N | Y | N | E | N | F | K | G | murine FR-3 | D | G | N | F | P | Y | Y | A | M | D | S | murine FR-4 |
| D7 VH hum 1 | human FR-1 | Y | F | D | I | N | human FR-2 | G | I | S | P | G | D | G | N | T | N | Y | N | E | N | F | K | G | human FR-3 | D | G | N | F | P | Y | Y | A | M | D | S | human FR-4 |
| D7 VH hum 2 | human FR-1 | Y | F | D | I | N | human FR-2 | G | I | S | P | G | D | G | N | T | N | Y | X3 | X4 | X5 | F | X6 | G | human FR-3 | D | G | N | F | P | Y | Y | A | M | D | S | human FR-4 |
| D7 VH hum 3 | human FR-1 | Y | F | D | I | N | human FR-2 | G | I | S | P | G | D | G | N | X2 | N | Y | X3 | X4 | X5 | F | X6 | G | human FR-3 | D | G | N | F | P | Y | Y | A | M | D | S | human FR-4 |
| D7 VH hum 4 | human FR-1 | Y | F | D | I | N | human FR-2 | G | I | S | P | G | D | X1 | N | X2 | N | Y | X3 | X4 | X5 | F | X6 | G | human FR-3 | D | G | N | F | P | Y | Y | A | M | D | S | human FR-4 |

amino acid replacement (shaded)

F: framework sequence

| | | CDR-L1 | | | | | | | | | | | | | | | | | CDR-L2 | | | | | | | | CDR-L3 | | | | | | | | |
|---|---|---|---|---|---|---|---|---|---|---|---|---|---|---|---|---|---|---|---|---|---|---|---|---|---|---|---|---|---|---|---|---|---|---|---|
| D7 VL murine | murine FR-1 | R | S | S | Q | S | L | V | H | S | N | G | N | T | Y | L | H | murine FR-2 | T | V | S | N | R | F | S | murine FR-3 | S | Q | S | T | H | V | P | T | murine FR-4 |
| D7 VL hum 1 | human FR-1 | R | S | S | Q | S | L | V | H | S | N | G | N | T | Y | L | H | human FR-2 | T | V | S | N | R | F | S | human FR-3 | S | Q | S | T | H | V | P | T | human FR-4 |
| D7 VL hum 2 | human FR-1 | R | S | S | Q | S | L | V | H | S | N | G | X8 | T | Y | L | H | human FR-2 | T | V | S | N | R | F | S | human FR-3 | S | Q | S | T | H | V | P | T | human FR-4 |
| D7 VL hum 3 | human FR-1 | R | S | S | Q | S | L | V | H | S | X7 | G | X8 | T | Y | L | H | human FR-2 | T | V | S | N | R | F | S | human FR-3 | S | Q | S | T | H | V | P | T | human FR-4 |
| D7 VL hum 4 | human FR-1 | R | S | S | Q | S | L | V | H | S | X7 | G | X8 | T | Y | L | H | human FR-2 | T | V | S | N | R | X9 | S | human FR-3 | S | Q | S | T | H | V | P | T | human FR-4 |

amino acid replacement (shaded)

X1, X4, X6, X7, X8: hydrophilic, uncharged amino acids [serine (S), threonine (T), asparagine (N), glutamine (Q)]
X2, X3, X9: aliphatic, uncharged amino acids [glycine (G), alanine (A), valine (V), leucine (L), isoleucine (I), proline (P)]
X5: basic amino acids [(histidine (H), lysine (K), arginine (R)]

Fig. 12a

```
                           IgKappa Leader
    ~~~~~~~~~~~~~~~~~~~~~~~~~~~~~~~~~~~~~~~~~~~~~~~~~~~~~~~~~~~~~~~~
     M  D  F  Q   V  Q  I   F  S  F   L  L  I  S   A  S  V   I  M  S
  1 ATGGATTTTC AGGTGCAGAT TTTCAGCTTC CTGCTAATCA GTGCCTCAGT CATAATGTCT
    TACCTAAAAG TCCACGTCTA AAAGTCGAAG GACGATTAGT CACGGAGTCA GTATTACAGA
                    scFv D7 codon splice optimized
       ~~~~~~~~~~~~~~~~~~~~~~~~~~~~~~~~~~~~~~~~~~~~~~~~~~~~~~~~~~~~~~
                                VH-D7
          ~~~~~~~~~~~~~~~~~~~~~~~~~~~~~~~~~~~~~~~~~~~~~~~~~~~~~~~~~~~
    IgKappa Leader
    ~~~
     R  M  A  Q   V  Q  L   Q  Q  S   G  A  E  L   V  E  P   G  A  S
 61 AGAATGGCCC AGGTGCAGCT TCAACAGTCT GGCGCGGAGC TGGTCGAGCC CGGTGCTAGC
    TCTTACCGGG TCCACGTCGA AGTTGTCAGA CCGCGCCTCG ACCAGCTCGG GCCACGATCG
                           VH-D7
    ~~~~~~~~~~~~~~~~~~~~~~~~~~~~~~~~~~~~~~~~~~~~~~~~~~~~~~~~~~~~~~~~
                                          CDR-H1
                                      ~~~~~~~~~~~~~~~~~
                   scFv D7 codon splice optimized
    ~~~~~~~~~~~~~~~~~~~~~~~~~~~~~~~~~~~~~~~~~~~~~~~~~~~~~~~~~~~~~~~~
     V  K  L  S   C  K  A   S  G  Y   T  F  T  Y   F  D  I   N  W  L
121 GTTAAGCTGA GTTGTAAGGC GTCCGGCTAC ACATTTACCT ACTTCGATAT CAATTGGCTG
    CAATTCGACT CAACATTCCG CAGGCCGATG TGTAAATGGA TGAAGCTATA GTTAACCGAC
                           VH-D7
    ~~~~~~~~~~~~~~~~~~~~~~~~~~~~~~~~~~~~~~~~~~~~~~~~~~~~~~~~~~~~~~~~
                                            CDR-H2
                                   ~~~~~~~~~~~~~~~~~~~~~~~~~~
                   scFv D7 codon splice optimized
    ~~~~~~~~~~~~~~~~~~~~~~~~~~~~~~~~~~~~~~~~~~~~~~~~~~~~~~~~~~~~~~~~
     R  Q  R  P   E  Q  G   L  E  W   I  G  G  I   S  P  G   D  G  N
181 AGACAAAGGC CTGAACAGGG CCTGGAATGG ATCGGCGGAA TCTCTCCCGG AGATGGGAAT
    TCTGTTTCCG GACTTGTCCC GGACCTTACC TAGCCGCCTT AGAGAGGGCC TCTACCCTTA
                           VH-D7
    ~~~~~~~~~~~~~~~~~~~~~~~~~~~~~~~~~~~~~~~~~~~~~~~~~~~~~~~~~~~~~~~~
              CDR-H2
    ~~~~~~~~~~~~~~~~~~~~~~~~~~~~~
                   scFv D7 codon splice optimized
    ~~~~~~~~~~~~~~~~~~~~~~~~~~~~~~~~~~~~~~~~~~~~~~~~~~~~~~~~~~~~~~~~
     T  N  Y  N   E  N  F   K  G  K   A  T  L  T   I  D  K   S  S  T
241 ACAAATTATA ACGAGAACTT CAAGGGAAAG GCTACTCTTA CTATAGACAA GTCCAGCACT
    TGTTTAATAT TGCTCTTGAA GTTCCCTTTC CGATGAGAAT GATATCTGTT CAGGTCGTGA
                           VH-D7
    ~~~~~~~~~~~~~~~~~~~~~~~~~~~~~~~~~~~~~~~~~~~~~~~~~~~~~~~~~~~~~~~~
                   scFv D7 codon splice optimized
    ~~~~~~~~~~~~~~~~~~~~~~~~~~~~~~~~~~~~~~~~~~~~~~~~~~~~~~~~~~~~~~~~
     T  A  Y  I   Q  L  S   R  L  T   S  E  D  S   A  V  Y   F  C  A
301 ACGGCCTACA TCCAGCTGTC CCGCCTCACG AGCGAGGACA GCGCCGTGTA TTTCTGTGCA
    TGCCGGATGT AGGTCGACAG GGCGGAGTGC TCGCTCCTGT CGCGGCACAT AAAGACACGT
                           VH-D7
    ~~~~~~~~~~~~~~~~~~~~~~~~~~~~~~~~~~~~~~~~~~~~~~~~~~~~~~~~~~~~~~~~
                    CDR-H3
       ~~~~~~~~~~~~~~~~~~~~~~~~~~~~~~~~~~~~
                   scFv D7 codon splice optimized
    ~~~~~~~~~~~~~~~~~~~~~~~~~~~~~~~~~~~~~~~~~~~~~~~~~~~~~~~~~~~~~~~~
     R  D  G  N   F  P  Y   Y  A  M   D  S  W  G   Q  G  T   S  V  T
361 AGGGACGGCA ACTTCCCCTA CTATGCAATG GATTCTTGGG GGCAGGGCAC TTCCGTCACA
    TCCCTGCCGT TGAAGGGGAT GATACGTTAC CTAAGAACCC CCGTCCCGTG AAGGCAGTGT
      VH-D7
    ~~~~~~~~~
                   scFv D7 codon splice optimized
    ~~~~~~~~~~~~~~~~~~~~~~~~~~~~~~~~~~~~~~~~~~~~~~~~~~~~~~~~~~~~~~~~
     V  S  S  A   K  T  T   P  K  L   G  G  G  G   S  G  G   G  G  S
421 GTGAGCTCTG CCAAGACCAC ACCGAAACTG GGCGGAGGAG GCAGTGGAGG TGGGGGGAGC
    CACTCGAGAC GGTTCTGGTG TGGCTTTGAC CCGCCTCCTC CGTCACCTCC ACCCCCCTCG
                                          VL-D7
                           ~~~~~~~~~~~~~~~~~~~~~~~~~~~~~~~~~~~~~~~
                   scFv D7 codon splice optimized
    ~~~~~~~~~~~~~~~~~~~~~~~~~~~~~~~~~~~~~~~~~~~~~~~~~~~~~~~~~~~~~~~~
     G  G  G  G   S  A  R   V  D  I   E  L  T  Q   S  P  L   S  L  P
481 GGGGGTGGGG GAAGTGCTCG CGTGGATATT GAGCTCACTC AGAGTCCTCT GTCTCTCCCT
    CCCCCACCCC CTTCACGAGC GCACCTATAA CTCGAGTGAG TCTCAGGAGA CAGAGAGGGA
                           VL-D7
    ~~~~~~~~~~~~~~~~~~~~~~~~~~~~~~~~~~~~~~~~~~~~~~~~~~~~~~~~~~~~~~~~
```

Fig. 12b

```
                                                         CDR-L1
                                                 ~~~~~~~~~~~~~~~~~~~~~~~~~~~~~
                     scFv D7 codon splice optimized
      ~~~~~~~~~~~~~~~~~~~~~~~~~~~~~~~~~~~~~~~~~~~~~~~~~~~~~~~~~~~~~~~~~
       V  I  L  G   D  Q  A   S  I  S   C  R  S  S   Q  S  L   V  H  S
 541  GTGATACTGG GCGACCAAGC TAGCATTAGC TGCCGAAGCA GCCAATCACT GGTCCACTCT
      CACTATGACC CGCTGGTTCG ATCGTAATCG ACGGCTTCGT CGGTTAGTGA CCAGGTGAGA
                                  VL-D7
      ~~~~~~~~~~~~~~~~~~~~~~~~~~~~~~~~~~~~~~~~~~~~~~~~~~~~~~~~~~~~~~~~~
             CDR-L1
      ~~~~~~~~~~~~~~~~~~~~~~~
                     scFv D7 codon splice optimized
      ~~~~~~~~~~~~~~~~~~~~~~~~~~~~~~~~~~~~~~~~~~~~~~~~~~~~~~~~~~~~~~~~~
       N  G  N  T   Y  L  H   W  F  L   Q  K  P  G   Q  S  P   K  L  L
 601  AACGGAAACA CCTATCTTCA CTGGTTTCTC CAAAAGCCTG GACAGTCCCC GAAGTTGCTT
      TTGCCTTTGT GGATAGAAGT GACCAAAGAG GTTTTCGGAC CTGTCAGGGG CTTCAACGAA
                                  VL-D7
      ~~~~~~~~~~~~~~~~~~~~~~~~~~~~~~~~~~~~~~~~~~~~~~~~~~~~~~~~~~~~~~~~~
                   CDR-L2
            ~~~~~~~~~~~~~~~~~~~~~~~
                     scFv D7 codon splice optimized
      ~~~~~~~~~~~~~~~~~~~~~~~~~~~~~~~~~~~~~~~~~~~~~~~~~~~~~~~~~~~~~~~~~
       I  Y  T  V   S  N  R   F  S  G   V  P  D  R   F  S  G   S  G  S
 661  ATTTATACTG TCAGCAACCG ATTCTCAGGG GTCCCCGATC GATTCAGCGG CAGCGGGAGC
      TAAATATGAC AGTCGTTGGC TAAGAGTCCC CAGGGGCTAG CTAAGTCGCC GTCGCCCTCG
                                  VL-D7
      ~~~~~~~~~~~~~~~~~~~~~~~~~~~~~~~~~~~~~~~~~~~~~~~~~~~~~~~~~~~~~~~~~
                     scFv D7 codon splice optimized
      ~~~~~~~~~~~~~~~~~~~~~~~~~~~~~~~~~~~~~~~~~~~~~~~~~~~~~~~~~~~~~~~~~
       G  T  D  F   T  L  K   I  S  R   V  E  A  E   D  L  G   V  Y  F
 721  GGGACCGACT TTACCCTCAA GATCTCCCGC GTGGAGGCCG AGGACCTGGG AGTCTATTTC
      CCCTGGCTGA AATGGGAGTT CTAGAGGGCG CACCTCCGGC TCCTGGACCC TCAGATAAAG
                                  VL-D7
      ~~~~~~~~~~~~~~~~~~~~~~~~~~~~~~~~~~~~~~~~~~~~~~~~~~~~~~~~~~~~~~~~~
                  CDR-L3
         ~~~~~~~~~~~~~~~~~~~~~~~~~~
                     scFv D7 codon splice optimized
      ~~~~~~~~~~~~~~~~~~~~~~~~~~~~~~~~~~~~~~~~~~~~~~~~~~~~~~~~~~~~~~~~~
       C  S  Q  S   T  H  V   P  T  F   G  G  G  T   K  L  E   I  K  R
 781  TGCAGCCAGT CTACTCATGT GCCGACGTTC GGAGGAGGGA CGAAGTTGGA GATAAAAAGA
      ACGTCGGTCA GATGAGTACA CGGCTGCAAG CCTCCTCCCT GCTTCAACCT CTATTTTTCT
                        Human IgG1 Fc Hinge-CH2/CH3 delta
               ~~~~~~~~~~~~~~~~~~~~~~~~~~~~~~~~~~~~~~~~~~~~~~~~~~~~~~~~
       S  D  P  A   E  P  K   S  P  D   K  T  H  T   C  P  P   C  P  A
 841  TCGGATCCCG CCGAGCCCAA ATCTCCTGAC AAAACTCACA CATGCCCACC GTGCCCAGCA
      AGCCTAGGGC GGCTCGGGTT TAGAGGACTG TTTTGAGTGT GTACGGGTGG CACGGGTCGT
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
       P  P  V  A   G  P  S   V  F  L   F  P  P  K   P  K  D   T  L  M
 901  CCTCCAGTCG CGGGACCGTC AGTCTTCCTC TTCCCCCCAA AACCCAAGGA CACCCTCATG
      GGAGGTCAGC GCCCTGGCAG TCAGAAGGAG AAGGGGGGTT TTGGGTTCCT GTGGGAGTAC
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
       I  A  R  T   P  E  V   T  C  V   V  V  D  V   S  H  E   D  P  E
 961  ATCGCCCGGA CCCCTGAGGT CACATGCGTG GTGGTGGACG TGAGCCACGA AGACCCTGAG
      TAGCGGGCCT GGGGACTCCA GTGTACGCAC CACCACCTGC ACTCGGTGCT TCTGGGACTC
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
       V  K  F  N   W  Y  V   D  G  V   E  V  H  N   A  K  T   K  P  R
1021  GTCAAGTTCA ACTGGTACGT GGACGGCGTG GAGGTGCATA ATGCCAAGAC AAAGCCGCGG
      CAGTTCAAGT TGACCATGCA CCTGCCGCAC CTCCACGTAT TACGGTTCTG TTTCGGCGCC
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
       E  E  Q  Y   N  S  T   Y  R  V   V  S  V  L   T  V  L   H  Q  D
1081  GAGGAGCAGT ACAACAGCAC GTACCGTGTG GTCAGCGTCC TCACCGTCCT GCACCAGGAC
      CTCCTCGTCA TGTTGTCGTG CATGGCACAC CAGTCGCAGG AGTGGCAGGA CGTGGTCCTG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
       W  L  N  G   K  E  Y   K  C  K   V  S  N  K   A  L  P   A  P  I
1141  TGGCTGAATG GCAAGGAGTA CAAGTGCAAG GTCTCCAACA AAGCCCTCCC AGCCCCCATC
      ACCGACTTAC CGTTCCTCAT GTTCACGTTC CAGAGGTTGT TTCGGGAGGG TCGGGGGTAG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
```

Fig. 12c

```
      E  K  T  I   S  K  A   K  G  Q   P  R  E  P   Q  V  Y   T  L  P
1201  GAGAAAACCA TCTCCAAAGC CAAAGGGCAG CCCCGAGAAC CACAGGTGTA CACCCTGCCC
      CTCTTTTGGT AGAGGTTTCG GTTTCCCGTC GGGGCTCTTG GTGTCCACAT GTGGGACGGG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
      P  S  R  D   E  L  T   K  N  Q   V  S  L  T   C  L  V   K  G  F
1261  CCATCCCGGG ATGAGCTGAC CAAGAACCAG GTCAGCCTGA CCTGCCTGGT CAAAGGCTTC
      GGTAGGGCCC TACTCGACTG GTTCTTGGTC CAGTCGGACT GGACGGACCA GTTTCCGAAG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
      Y  P  S  D   I  A  V   E  W  E   S  N  G  Q   P  E  N   N  Y  K
1321  TATCCCAGCG ACATCGCCGT GGAGTGGGAG AGCAATGGGC AGCCGGAGAA CAACTACAAG
      ATAGGGTCGC TGTAGCGGCA CCTCACCCTC TCGTTACCCG TCGGCCTCTT GTTGATGTTC
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
      T  T  P  P   V  L  D   S  D  G   S  F  F  L   Y  S  K   L  T  V
1381  ACCACGCCTC CCGTGCTGGA CTCCGACGGC TCCTTCTTCC TCTACAGCAA GCTCACCGTG
      TGGTGCGGAG GGCACGACCT GAGGCTGCCG AGGAAGAAGG AGATGTCGTT CGAGTGGCAC
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
      D  K  S  R   W  Q  Q   G  N  V   F  S  C  S   V  M  H   E  A  L
1441  GACAAGAGCA GGTGGCAGCA GGGGAACGTC TTCTCATGCT CCGTGATGCA TGAGGCTCTG
      CTGTTCTCGT CCACCGTCGT CCCCTTGCAG AAGAGTACGA GGCACTACGT ACTCCGAGAC
                                                        human CD28 deltaLck TM+IC
                                                         ~~~~~~~
                Human IgG1 Fc Hinge-CH2/CH3 delta
      ~~~~~~~~~~~~~~~~~~~~~~~~~~~~~~~~~~~~~~~~~~~~~~~~~~~~~~~~~
      H  N  H  Y   T  Q  K   S  L  S   L  S  P  G   K  K  D   P  K  F
1501  CACAACCACT ACACGCAGAA GAGCCTCTCC CTGTCTCCGG GTAAAAAAGA TCCCAAATTT
      GTGTTGGTGA TGTGCGTCTT CTCGGAGAGG GACAGAGGCC CATTTTTTCT AGGGTTTAAA
                       human CD28 deltaLck TM+IC
      ~~~~~~~~~~~~~~~~~~~~~~~~~~~~~~~~~~~~~~~~~~~~~~~~~~~~~~~~~~~~~~~~~
      W  V  L  V   V  V  G   G  V  L   A  C  Y  S   L  L  V   T  V  A
1561  TGGGTGCTGG TGGTGGTTGG TGGAGTCCTG GCTTGCTATA GCTTGCTAGT AACAGTGGCC
      ACCCACGACC ACCACCAACC ACCTCAGGAC CGAACGATAT CGAACGATCA TTGTCACCGG
                       human CD28 deltaLck TM+IC
      ~~~~~~~~~~~~~~~~~~~~~~~~~~~~~~~~~~~~~~~~~~~~~~~~~~~~~~~~~~~~~~~~~
      F  I  I  F   W  V  R   S  K  R   S  R  L  L   H  S  D   Y  M  N
1621  TTTATTATTT TCTGGGTGAG GAGTAAGAGG AGCAGGCTCC TGCACAGTGA CTACATGAAC
      AAATAATAAA AGACCCACTC CTCATTCTCC TCGTCCGAGG ACGTGTCACT GATGTACTTG
                       human CD28 deltaLck TM+IC
      ~~~~~~~~~~~~~~~~~~~~~~~~~~~~~~~~~~~~~~~~~~~~~~~~~~~~~~~~~~~~~~~~~
      M  T  P  R   R  P  G   P  T  R   K  H  Y  Q   A  Y  A   A  A  R
1681  ATGACTCCCC GCCGCCCCGG GCCCACCCGC AAGCATTACC AGGCCTATGC CGCCGCACGC
      TACTGAGGGG CGGCGGGGCC CGGGTGGGCG TTCGTAATGG TCCGGATACG GCGGCGTGCG
                                             Human CD3zeta
                                 ~~~~~~~~~~~~~~~~~~~~~~~~~~~~~~~~~~~~~~~~~~
      human CD28 deltaLck TM+IC
      ~~~~~~~~~~~~~~~~~~~~~~~
      D  F  A  A   Y  R  S   L  R  V   K  F  S  R   S  A  D   A  P  A
1741  GACTTCGCAG CCTATCGCTC CCTGAGAGTG AAGTTCAGCA GGAGCGCAGA CGCCCCCGCG
      CTGAAGCGTC GGATAGCGAG GGACTCTCAC TTCAAGTCGT CCTCGCGTCT GCGGGGGCGC
                             Human CD3zeta
      ~~~~~~~~~~~~~~~~~~~~~~~~~~~~~~~~~~~~~~~~~~~~~~~~~~~~~~~~~~~~~~~~~
      Y  Q  Q  G   Q  N  Q   L  Y  N   E  L  N  L   G  R  R   E  E  Y
1801  TACCAGCAGG GCCAGAACCA GCTCTATAAC GAGCTCAATC TAGGACGAAG AGAGGAGTAC
      ATGGTCGTCC CGGTCTTGGT CGAGATATTG CTCGAGTTAG ATCCTGCTTC TCTCCTCATG
                             Human CD3zeta
      ~~~~~~~~~~~~~~~~~~~~~~~~~~~~~~~~~~~~~~~~~~~~~~~~~~~~~~~~~~~~~~~~~
      D  V  L  D   K  R  R   G  R  D   P  E  M  G   G  K  P   R  R  K
1861  GATGTTTTGG ACAAGAGACG TGGCCGGGAC CCTGAGATGG GGGGAAAGCC GAGAAGGAAG
      CTACAAAACC TGTTCTCTGC ACCGGCCCTG GGACTCTACC CCCCTTTCGG CTCTTCCTTC
                             Human CD3zeta
      ~~~~~~~~~~~~~~~~~~~~~~~~~~~~~~~~~~~~~~~~~~~~~~~~~~~~~~~~~~~~~~~~~
      N  P  Q  E   G  L  Y   N  E  L   Q  K  D  K   M  A  E   A  Y  S
1921  AACCCTCAGG AAGGCCTGTA CAATGAACTG CAGAAAGATA AGATGGCGGA GGCCTACAGT
      TTGGGAGTCC TTCCGGACAT GTTACTTGAC GTCTTTCTAT TCTACCGCCT CCGGATGTCA
                             Human CD3zeta
      ~~~~~~~~~~~~~~~~~~~~~~~~~~~~~~~~~~~~~~~~~~~~~~~~~~~~~~~~~~~~~~~~~
      E  I  G  M   K  G  E   R  R  R   G  K  G  H   D  G  L   Y  Q  G
1981  GAGATTGGGA TGAAAGGCGA GCGCCGGAGG GGCAAGGGGC ACGATGGCCT TTACCAGGGT
      CTCTAACCCT ACTTTCCGCT CGCGGCCTCC CCGTTCCCCG TGCTACCGGA AATGGTCCCA
                             Human CD3zeta
```

Fig. 12d

```
      ~~~~~~~~~~~~~~~~~~~~~~~~~~~~~~~~~~~~~~~~~~~~~~~~~~~~~~~~~~~~~~~~~
       L  S  T  A   T  K  D   T  Y  D   A  L  H  M   Q  A  L   P  P  R
2041  CTCAGTACAG CCACCAAGGA CACCTACGAC GCCCTTCACA TGCAGGCCCT GCCCCCTCGC
      GAGTCATGTC GGTGGTTCCT GTGGATGCTG CGGGAAGTGT ACGTCCGGGA CGGGGGAGCG
      Human CD3zeta
      ~~~
       *
2101  TAA
      ATT
```

Fig. 13a

```
                          IgKappa Leader
      ~~~~~~~~~~~~~~~~~~~~~~~~~~~~~~~~~~~~~~~~~~~~~~~~~~~~~~~~~~~~
      M  D  F  Q   V  Q  I   F  S  F   L  L  I  S   A  S  V   I  M  S
  1   ATGGATTTTC AGGTGCAGAT TTTCAGCTTC CTGCTAATCA GTGCCTCAGT CATAATGTCT
      TACCTAAAAG TCCACGTCTA AAAGTCGAAG GACGATTAGT CACGGAGTCA GTATTACAGA
                    scFv D7 codon splice optimized
         ~~~~~~~~~~~~~~~~~~~~~~~~~~~~~~~~~~~~~~~~~~~~~~~~~~~~~~~~~
                                   VH-D7
            ~~~~~~~~~~~~~~~~~~~~~~~~~~~~~~~~~~~~~~~~~~~~~~~~~~~~~~
      IgKappa Leader
      ~~~
      R  M  A  Q   V  Q  L   Q  Q  S   G  A  E  L   V  E  P   G  A  S
 61   AGAATGGCCC AGGTGCAGCT TCAACAGTCT GGCGCGGAGC TGGTCGAGCC CGGTGCTAGC
      TCTTACCGGG TCCACGTCGA AGTTGTCAGA CCGCGCCTCG ACCAGCTCGG GCCACGATCG
                              VH-D7
      ~~~~~~~~~~~~~~~~~~~~~~~~~~~~~~~~~~~~~~~~~~~~~~~~~~~~~~~~~~~~
                                              CDR-H1
                                          ~~~~~~~~~~~~~~~~
                   scFv D7 codon splice optimized
      ~~~~~~~~~~~~~~~~~~~~~~~~~~~~~~~~~~~~~~~~~~~~~~~~~~~~~~~~~~~~
      V  K  L  S   C  K  A   S  G  Y   T  F  T  Y   F  D  I   N  W  L
121   GTTAAGCTGA GTTGTAAGGC GTCCGGCTAC ACATTTACCT ACTTCGATAT CAATTGGCTG
      CAATTCGACT CAACATTCCG CAGGCCGATG TGTAAATGGA TGAAGCTATA GTTAACCGAC
                              VH-D7
      ~~~~~~~~~~~~~~~~~~~~~~~~~~~~~~~~~~~~~~~~~~~~~~~~~~~~~~~~~~~~
                                                CDR-H2
                                       ~~~~~~~~~~~~~~~~~~~~~~~~
                   scFv D7 codon splice optimized
      ~~~~~~~~~~~~~~~~~~~~~~~~~~~~~~~~~~~~~~~~~~~~~~~~~~~~~~~~~~~~
      R  Q  R  P   E  Q  G   L  E  W   I  G  G  I   S  P  G   D  G  N
181   AGACAAAGGC CTGAACAGGG CCTGGAATGG ATCGGCGGAA TCTCTCCCGG AGATGGGAAT
      TCTGTTTCCG GACTTGTCCC GGACCTTACC TAGCCGCCTT AGAGAGGGCC TCTACCCTTA
                              VH-D7
      ~~~~~~~~~~~~~~~~~~~~~~~~~~~~~~~~~~~~~~~~~~~~~~~~~~~~~~~~~~~~
               CDR-H2
      ~~~~~~~~~~~~~~~~~~~~~~~~~~~
                   scFv D7 codon splice optimized
      ~~~~~~~~~~~~~~~~~~~~~~~~~~~~~~~~~~~~~~~~~~~~~~~~~~~~~~~~~~~~
      T  N  Y  N   E  N  F   K  G  K   A  T  L  T   I  D  K   S  S  T
241   ACAAATTATA ACGAGAACTT CAAGGGAAAG GCTACTCTTA CTATAGACAA GTCCAGCACT
      TGTTTAATAT TGCTCTTGAA GTTCCCTTTC CGATGAGAAT GATATCTGTT CAGGTCGTGA
                              VH-D7
      ~~~~~~~~~~~~~~~~~~~~~~~~~~~~~~~~~~~~~~~~~~~~~~~~~~~~~~~~~~~~
                   scFv D7 codon splice optimized
      ~~~~~~~~~~~~~~~~~~~~~~~~~~~~~~~~~~~~~~~~~~~~~~~~~~~~~~~~~~~~
      T  A  Y  I   Q  L  S   R  L  T   S  E  D  S   A  V  Y   F  C  A
301   ACGGCCTACA TCCAGCTGTC CCGCCTCACG AGCGAGGACA GCGCCGTGTA TTTCTGTGCA
      TGCCGGATGT AGGTCGACAG GGCGGAGTGC TCGCTCCTGT CGCGGCACAT AAAGACACGT
                              VH-D7
      ~~~~~~~~~~~~~~~~~~~~~~~~~~~~~~~~~~~~~~~~~~~~~~~~~~~~~~~~~~~~
                    CDR-H3
         ~~~~~~~~~~~~~~~~~~~~~~~~~~~~~~~~~
                   scFv D7 codon splice optimized
      ~~~~~~~~~~~~~~~~~~~~~~~~~~~~~~~~~~~~~~~~~~~~~~~~~~~~~~~~~~~~
      R  D  G  N   F  P  Y   Y  A  M   D  S  W  G   Q  G  T   S  V  T
361   AGGGACGGCA ACTTCCCCTA CTATGCAATG GATTCTTGGG GGCAGGGCAC TTCCGTCACA
      TCCCTGCCGT TGAAGGGGAT GATACGTTAC CTAAGAACCC CCGTCCCGTG AAGGCAGTGT
        VH-D7
      ~~~~~~~~
                   scFv D7 codon splice optimized
      ~~~~~~~~~~~~~~~~~~~~~~~~~~~~~~~~~~~~~~~~~~~~~~~~~~~~~~~~~~~~
      V  S  S  A   K  T  T   P  K  L   G  G  G  G   S  G  G   G  G  S
421   GTGAGCTCTG CCAAGACCAC ACCGAAACTG GGCGGAGGAG GCAGTGGAGG TGGGGGGAGC
      CACTCGAGAC GGTTCTGGTG TGGCTTTGAC CCGCCTCCTC CGTCACCTCC ACCCCCCTCG
                                             VL-D7
                                ~~~~~~~~~~~~~~~~~~~~~~~~~~~~~~~~~~~~
                   scFv D7 codon splice optimized
      ~~~~~~~~~~~~~~~~~~~~~~~~~~~~~~~~~~~~~~~~~~~~~~~~~~~~~~~~~~~~
      G  G  G  G   S  A  R   V  D  I   E  L  T  Q   S  P  L   S  L  P
481   GGGGGTGGGG GAAGTGCTCG CGTGGATATT GAGCTCACTC AGAGTCCTCT GTCTCTCCCT
      CCCCCACCCC CTTCACGAGC GCACCTATAA CTCGAGTGAG TCTCAGGAGA CAGAGAGGGA
                              VL-D7
      ~~~~~~~~~~~~~~~~~~~~~~~~~~~~~~~~~~~~~~~~~~~~~~~~~~~~~~~~~~~~
```

Fig. 13b

```
                                                         CDR-L1
                                               ~~~~~~~~~~~~~~~~~~~~~~~~~~~~~
                 scFv D7 codon splice optimized
      ~~~~~~~~~~~~~~~~~~~~~~~~~~~~~~~~~~~~~~~~~~~~~~~~~~~~~~~~~~~~~~~~~~~~~
       V  I  L  G   D  Q  A   S  I  S   C  R  S  S   Q  S  L   V  H  S
 541  GTGATACTGG GCGACCAAGC TAGCATTAGC TGCCGAAGCA GCCAATCACT GGTCCACTCT
      CACTATGACC CGCTGGTTCG ATCGTAATCG ACGGCTTCGT CGGTTAGTGA CCAGGTGAGA
                             VL-D7
      ~~~~~~~~~~~~~~~~~~~~~~~~~~~~~~~~~~~~~~~~~~~~~~~~~~~~~~~~~~~~~~~~~~~~~
             CDR-L1
      ~~~~~~~~~~~~~~~~~~~~~~~
                 scFv D7 codon splice optimized
      ~~~~~~~~~~~~~~~~~~~~~~~~~~~~~~~~~~~~~~~~~~~~~~~~~~~~~~~~~~~~~~~~~~~~~
       N  G  N  T   Y  L  H   W  F  L   Q  K  P  G   Q  S  P   K  L  L
 601  AACGGAAACA CCTATCTTCA CTGGTTTCTC CAAAAGCCTG GACAGTCCCC GAAGTTGCTT
      TTGCCTTTGT GGATAGAAGT GACCAAAGAG GTTTTCGGAC CTGTCAGGGG CTTCAACGAA
                             VL-D7
      ~~~~~~~~~~~~~~~~~~~~~~~~~~~~~~~~~~~~~~~~~~~~~~~~~~~~~~~~~~~~~~~~~~~~~
                   CDR-L2
            ~~~~~~~~~~~~~~~~~~~~~~~
                 scFv D7 codon splice optimized
      ~~~~~~~~~~~~~~~~~~~~~~~~~~~~~~~~~~~~~~~~~~~~~~~~~~~~~~~~~~~~~~~~~~~~~
       I  Y  T  V   S  N  R   F  S  G   V  P  D  R   F  S  G   S  G  S
 661  ATTTATACTG TCAGCAACCG ATTCTCAGGG GTCCCCGATC GATTCAGCGG CAGCGGGAGC
      TAAATATGAC AGTCGTTGGC TAAGAGTCCC CAGGGGCTAG CTAAGTCGCC GTCGCCCTCG
                             VL-D7
      ~~~~~~~~~~~~~~~~~~~~~~~~~~~~~~~~~~~~~~~~~~~~~~~~~~~~~~~~~~~~~~~~~~~~~
                 scFv D7 codon splice optimized
      ~~~~~~~~~~~~~~~~~~~~~~~~~~~~~~~~~~~~~~~~~~~~~~~~~~~~~~~~~~~~~~~~~~~~~
       G  T  D  F   T  L  K   I  S  R   V  E  A  E   D  L  G   V  Y  F
 721  GGGACCGACT TTACCCTCAA GATCTCCCGC GTGGAGGCCG AGGACCTGGG AGTCTATTTC
      CCCTGGCTGA AATGGGAGTT CTAGAGGGCG CACCTCCGGC TCCTGGACCC TCAGATAAAG
                             VL-D7
      ~~~~~~~~~~~~~~~~~~~~~~~~~~~~~~~~~~~~~~~~~~~~~~~~~~~~~~~~~~~~~~~~~~~~~
                  CDR-L3
         ~~~~~~~~~~~~~~~~~~~~~~~~~~
                 scFv D7 codon splice optimized
      ~~~~~~~~~~~~~~~~~~~~~~~~~~~~~~~~~~~~~~~~~~~~~~~~~~~~~~~~~~~~~~~~~~~~~
       C  S  Q  S   T  H  V   P  T  F   G  G  G  T   K  L  E   I  K  R
 781  TGCAGCCAGT CTACTCATGT GCCGACGTTC GGAGGAGGGA CGAAGTTGGA GATAAAAAGA
      ACGTCGGTCA GATGAGTACA CGGCTGCAAG CCTCCTCCCT GCTTCAACCT CTATTTTTCT
                        Human IgG1 Fc Hinge-CH2/CH3 delta
                   ~~~~~~~~~~~~~~~~~~~~~~~~~~~~~~~~~~~~~~~~~~~~~~~~~~~~~~~
       A  A  A  L   P  A  E   P  K  S   P  D  K  T   H  T  C   P  P  C
 841  GCGGCCGCTC TACCCGCCGA GCCCAAATCT CCTGACAAAA CTCACACATG CCCACCGTGC
      CGCCGGCGAG ATGGGCGGCT CGGGTTTAGA GGACTGTTTT GAGTGTGTAC GGGTGGCACG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~~~~~
       P  A  P  P   V  A  G   P  S  V   F  L  F  P   P  K  P   K  D  T
 901  CCAGCACCTC CAGTCGCGGG ACCGTCAGTC TTCCTCTTCC CCCCAAAACC CAAGGACACC
      GGTCGTGGAG GTCAGCGCCC TGGCAGTCAG AAGGAGAAGG GGGGTTTTGG GTTCCTGTGG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~~~~~
       L  M  I  A   R  T  P   E  V  T   C  V  V  V   D  V  S   H  E  D
 961  CTCATGATCG CCCGGACCCC TGAGGTCACA TGCGTGGTGG TGGACGTGAG CCACGAAGAC
      GAGTACTAGC GGGCCTGGGG ACTCCAGTGT ACGCACCACC ACCTGCACTC GGTGCTTCTG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~~~~~
       P  E  V  K   F  N  W   Y  V  D   G  V  E  V   H  N  A   K  T  K
1021  CCTGAGGTCA AGTTCAACTG GTACGTGGAC GGCGTGGAGG TGCATAATGC CAAGACAAAG
      GGACTCCAGT TCAAGTTGAC CATGCACCTG CCGCACCTCC ACGTATTACG GTTCTGTTTC
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~~~~~
       P  R  E  E   Q  Y  N   S  T  Y   R  V  V  S   V  L  T   V  L  H
1081  CCGCGGGAGG AGCAGTACAA CAGCACGTAC CGTGTGGTCA GCGTCCTCAC CGTCCTGCAC
      GGCGCCCTCC TCGTCATGTT GTCGTGCATG GCACACCAGT CGCAGGAGTG GCAGGACGTG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~~~~~
       Q  D  W  L   N  G  K   E  Y  K   C  K  V  S   N  K  A   L  P  A
1141  CAGGACTGGC TGAATGGCAA GGAGTACAAG TGCAAGGTCT CCAACAAAGC CCTCCCAGCC
      GTCCTGACCG ACTTACCGTT CCTCATGTTC ACGTTCCAGA GGTTGTTTCG GGAGGGTCGG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~~~~~
```

Fig. 13c

```
      P  I  E  K   T  I  S   K  A  K   G  Q  P  R   E  P  Q   V  Y  T
1201  CCCATCGAGA AAACCATCTC CAAAGCCAAA GGGCAGCCCC GAGAACCACA GGTGTACACC
      GGGTAGCTCT TTTGGTAGAG GTTTCGGTTT CCCGTCGGGG CTCTTGGTGT CCACATGTGG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
      L  P  P  S   R  D  E   L  T  K   N  Q  V  S   L  T  C   L  V  K
1261  CTGCCCCCAT CCCGGGATGA GCTGACCAAG AACCAGGTCA GCCTGACCTG CCTGGTCAAA
      GACGGGGGTA GGGCCCTACT CGACTGGTTC TTGGTCCAGT CGGACTGGAC GGACCAGTTT
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
      G  F  Y  P   S  D  I   A  V  E   W  E  S  N   G  Q  P   E  N  N
1321  GGCTTCTATC CCAGCGACAT CGCCGTGGAG TGGGAGAGCA ATGGGCAGCC GGAGAACAAC
      CCGAAGATAG GGTCGCTGTA GCGGCACCTC ACCCTCTCGT TACCCGTCGG CCTCTTGTTG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
      Y  K  T  T   P  P  V   L  D  S   D  G  S  F   F  L  Y   S  K  L
1381  TACAAGACCA CGCCTCCCGT GCTGGACTCC GACGGCTCCT TCTTCCTCTA CAGCAAGCTC
      ATGTTCTGGT GCGGAGGGCA CGACCTGAGG CTGCCGAGGA AGAAGGAGAT GTCGTTCGAG
                   Human IgG1 Fc Hinge-CH2/CH3 delta
      ~~~~~~~~~~~~~~~~~~~~~~~~~~~~~~~~~~~~~~~~~~~~~~~~~~~~~~~~~~~~~~~~~
      T  V  D  K   S  R  W   Q  Q  G   N  V  F  S   C  S  V   M  H  E
1441  ACCGTGGACA AGAGCAGGTG GCAGCAGGGG AACGTCTTCT CATGCTCCGT GATGCATGAG
      TGGCACCTGT TCTCGTCCAC CGTCGTCCCC TTGCAGAAGA GTACGAGGCA CTACGTACTC
                                              Ser-Insert          Human CD8a(tm)
                                              ~~~                 ~~~
                  Human IgG1 Fc Hinge-CH2/CH3 delta
      ~~~~~~~~~~~~~~~~~~~~~~~~~~~~~~~~~~~~~~~~~~~~~~~~~~~~~~~~~~~~~
      A  L  H  N   H  Y  T   Q  K  S   L  S  S  L   S  P  G   K  K  I
1501  GCTCTGCACA ACCACTACAC GCAGAAGAGC CTCTCGAGCC TGTCTCCGGG TAAAAAAATC
      CGAGACGTGT TGGTGATGTG CGTCTTCTCG GAGAGCTCGG ACAGAGGCCC ATTTTTTTAG
                              Human CD8a(tm)
      ~~~~~~~~~~~~~~~~~~~~~~~~~~~~~~~~~~~~~~~~~~~~~~~~~~~~~~~~~~~~~~~~~
      Y  I  W  A   P  L  A   G  T  C   G  V  L  L   L  S  L   V  I  T
1561  TACATCTGGG CGCCCTTGGC CGGGACTTGT GGGGTCCTTC TCCTGTCACT GGTTATCACC
      ATGTAGACCC GCGGGAACCG GCCCTGAACA CCCCAGGAAG AGGACAGTGA CCAATAGTGG
      Human CD8a(tm)
      ~~~~~~~~~
                                 Human 4-1BB(ic)
               ~~~~~~~~~~~~~~~~~~~~~~~~~~~~~~~~~~~~~~~~~~~~~~~~~~~~~~~~
      L  Y  C  K   R  G  R   K  K  L   L  Y  I  F   K  Q  P   F  M  R
1621  CTTTACTGCA AACGGGGCAG AAAGAAACTC CTGTATATAT TCAAACAACC ATTTATGAGA
      GAAATGACGT TTGCCCCGTC TTTCTTTGAG GACATATATA AGTTTGTTGG TAAATACTCT
                             Human 4-1BB(ic)
      ~~~~~~~~~~~~~~~~~~~~~~~~~~~~~~~~~~~~~~~~~~~~~~~~~~~~~~~~~~~~~~~~~
      P  V  Q  T   T  Q  E   E  D  G   C  S  C  R   F  P  E   E  E  E
1681  CCAGTACAAA CTACTCAAGA GGAAGATGGC TGTAGCTGCC GATTTCCAGA AGAAGAAGAA
      GGTCATGTTT GATGAGTTCT CCTTCTACCG ACATCGACGG CTAAAGGTCT TCTTCTTCTT
                                        Human CD3zeta
                      ~~~~~~~~~~~~~~~~~~~~~~~~~~~~~~~~~~~~~~~~~~~~~~~~~
      Human 4-1BB(ic)
      ~~~~~~~~~~~~~~~~
      G  G  C  E   L  L  R   V  K  F   S  R  S  A   D  A  P   A  Y  Q
1741  GGAGGATGTG AACTGCTGAG AGTGAAGTTC AGCAGGAGCG CAGACGCCCC CGCGTACCAG
      CCTCCTACAC TTGACGACTC TCACTTCAAG TCGTCCTCGC GTCTGCGGGG GCGCATGGTC
                              Human CD3zeta
      ~~~~~~~~~~~~~~~~~~~~~~~~~~~~~~~~~~~~~~~~~~~~~~~~~~~~~~~~~~~~~~~~~
      Q  G  Q  N   Q  L  Y   N  E  L   N  L  G  R   R  E  E   Y  D  V
1801  CAGGGCCAGA ACCAGCTCTA TAACGAGCTC AATCTAGGAC GAAGAGAGGA GTACGATGTT
      GTCCCGGTCT TGGTCGAGAT ATTGCTCGAG TTAGATCCTG CTTCTCTCCT CATGCTACAA
                              Human CD3zeta
      ~~~~~~~~~~~~~~~~~~~~~~~~~~~~~~~~~~~~~~~~~~~~~~~~~~~~~~~~~~~~~~~~~
      L  D  K  R   R  G  R   D  P  E   M  G  G  K   P  R  R   K  N  P
1861  TTGGACAAGA GACGTGGCCG GGACCCTGAG ATGGGGGGAA AGCCGAGAAG GAAGAACCCT
      AACCTGTTCT CTGCACCGGC CCTGGGACTC TACCCCCCTT TCGGCTCTTC CTTCTTGGGA
                              Human CD3zeta
      ~~~~~~~~~~~~~~~~~~~~~~~~~~~~~~~~~~~~~~~~~~~~~~~~~~~~~~~~~~~~~~~~~
      Q  E  G  L   Y  N  E   L  Q  K   D  K  M  A   E  A  Y   S  E  I
1921  CAGGAAGGCC TGTACAATGA ACTGCAGAAA GATAAGATGG CGGAGGCCTA CAGTGAGATT
      GTCCTTCCGG ACATGTTACT TGACGTCTTT CTATTCTACC GCCTCCGGAT GTCACTCTAA
                              Human CD3zeta
      ~~~~~~~~~~~~~~~~~~~~~~~~~~~~~~~~~~~~~~~~~~~~~~~~~~~~~~~~~~~~~~~~~
      G  M  K  G   E  R  R   R  G  K   G  H  D  G   L  Y  Q   G  L  S
1981  GGGATGAAAG GCGAGCGCCG GAGGGGCAAG GGGCACGATG GCCTTTACCA GGGTCTCAGT
```

Fig. 13d

```
      CCCTACTTTC CGCTCGCGGC CTCCCCGTTC CCCGTGCTAC CGGAAATGGT CCCAGAGTCA
                                                                STOP
                                                                ~~~
                           Human CD3zeta
      ~~~~~~~~~~~~~~~~~~~~~~~~~~~~~~~~~~~~~~~~~~~~~~~~~~~~~~~~~~~~~~~
       T  A  T  K   D  T  Y   D  A  L   H  M  Q  A   L  P  P   R  *
2041  ACAGCCACCA AGGACACCTA CGACGCCCTT CACATGCAGG CCCTGCCCCC TCGCTAA
      TGTCGGTGGT TCCTGTGGAT GCTGCGGGAA GTGTACGTCC GGGACGGGGG AGCGATT
```

CHIMERIC ANTIGEN RECEPTORS THAT BIND TO PROSTATE SPECIFIC MEMBRANE ANTIGEN

PRIORITY

This application corresponds to the U.S. National phase of International Application No. PCT/EP2019/065822, filed Jun. 17, 2019, which, in turn, claims priority to European Patent Application No. 18180026.9 filed Jun. 27, 2018, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created Sep. 5, 2025, is named LNK_223US_SLV2.txt and is 37,487 bytes in size.

TECHNICAL FIELD OF THE PRESENT INVENTION

The present invention relates to chimeric antigen receptors that bind to tumor antigens whereby the antigen is the prostate specific membrane antigen (PSMA). The chimeric antigen receptors (in the following CAR) are brought into immune cells, in particular T cells, NK cells, iNKT cells and CIK cells, which then specifically react with tumor cells expressing PSMA which leads to the elimination of the tumor cells. The constructs of the present invention contain two major parts. On the one hand the antigen-binding region which specifically binds to the prostate specific membrane antigen (PSMA) and on the other hand co-stimulatory domains derived from a receptor of an immune cell responsible for signal transduction and activation of the immune cell.

BACKGROUND OF THE PRESENT INVENTION

Prostate cancer remains the second-most frequently diagnosed cancer among men worldwide with estimated 1.1 million new cases per year. Moreover, with expected 307,000 deaths, it represents the fifth leading cause of cancer deaths. Whereas primary tumors can successfully be treated, there is no curative treatment for advanced stages. Therefore, new therapeutic options are urgently needed.

The prostate specific membrane antigen (PSMA) is the best characterized antigen in prostate cancer for antibody-based diagnostic and therapeutic intervention. This protein is also known as glutamate carboxypeptidase II (EC 3.4.17.21), N-acetyl-linked acidic dipeptidase I (NAALADase), or folate hydrolase. PSMA is a type II membrane glycoprotein consisting of 750 amino acids (aa) with a small intracellular domain of 19 aa, a transmembrane domain of 24 aa, and a large extracellular domain of 707 aa. The extracellular domain folds into three distinct domains: the protease domain (aa 57-116 and 352-590), the apical domain (aa 117-351), and the C-terminal domain (aa 591-750). It shows a high structural similarity and identity to the human transferrin receptor 1. PSMA is highly restricted to the surface of prostate cancer cells, is present on cancer cells during all tumor stages, and shows an enhanced expression in androgen-independent and metastatic disease. PSMA is not secreted into the extracellular space and undergoes constitutive internalization, which is enhanced by binding of PSMA-specific antibodies. These characteristics make it an ideal candidate for the targeted treatment of advanced prostate cancer. Moreover, PSMA was also found to be expressed in the neovascular endothelium of virtually all solid tumor types without expression in normal vascular endothelium. It is therefore considered to be a unique antiangiogenic target.

Monoclonal antibodies (mAbs) are highly specific and versatile tools for cell targeting. In the last decades, they have attracted high interest in medical research and have become the most rapidly expanding class of pharmaceuticals for treating a variety of human diseases including cancer. Antibody 7E11 was the first published PSMA-specific mAb and was found to bind to the N-terminus (MWNLLH) of the intracellular domain of PSMA. The In-labeled form of 7E11 (ProstaScint, Cytogen, Philadelphia, PA) has received approval from the U.S. Food and Drug Administration (FDA) for the detection and imaging of metastatic prostate cancer in soft tissues. However, because the antibody binds an intracellular epitope, 7E11 is not capable to bind to viable cells. Positive signals in the in vivo imaging with ProstaScint had to be traced back to the detection of dead or dying cells within the tumor masses. Therefore, a new class of anti-PSMA mAbs was generated, which specifically bind to extracellular epitopes of PSMA expressed by living cells.

EP 1 883 698 discloses three different mAbs, 3/A12, 3/E7, 3/F11, which show a strong and specific binding to the extracellular moiety of PSMA on the surface of prostate cancer cells and prostate tissue specimens. In direct comparison with mAb J591, a clinically validated antibody for radioimmunotherapy (PMID:18552139; PMID:24135437; PMID:25771365; PMID: 26175541), the mAb 3/F11 showed higher binding to PSMA expressing C4-2 prostate cancer target cells ($K_d$ [defined as mean half-maximal saturation concentration] of 3/F11=9 nM; $K_d$ of J591=16 nM). Moreover, competitive binding studies demonstrated that mAb 3/F11 binds to a different extracellular PSMA epitope than J591 (PMID:19938014). In an immunohistological study on a panel of human normal tissues, no binding of the 3/F11 mAb to PSMA-negative tissues (adrenal, bone marrow, cerebellum, cerebrum, pituitary, colon, esophagus, heart, kidney, liver, lung, mesothelial cells of the pericardium, nerve, ovary, pancreas, skeletal muscle, skin, spleen, stomach, testis, thymus, thyroid, tonsil, and uterus) was detected. Only binding to secretory cells of the salivary glands and to duodenal brush border cells was observed, which are known to express PSMA (PMID:19938014). The mAb 3/F11 showed a moderate immunoreactivity on acinar secretory epithelial cells of all tested normal prostate tissues. A more intense and extensive staining was noticed in nearly all epithelial cells of adenocarcinomas as well as in lymph node metastases. No immunohistological staining on frozen sections of breast specimen was detected. In contrast and in accordance with other published data, staining of the mammary ductal epithelium was detected with mAb J591. Since PSMA expression in the breast tissue was neither detected by PCR nor by Western blotting, it is likely that mAb J591 cross-reacts with another antigen.

The single-chain variable fragment (scFv) D7 (as disclosed in EP 1 883 698 B1) was generated by phage display technique from the mAb 3/F11. The most important fragments for the specificity of the anti-PSMA scFv are the $V_L$ and the $V_H$ parts, which are preferably linked with a polyglycin linker.-D7 bound to PSMA-expressing C4-2 cells with a $K_d$ of about 18 nM, and preincubation with the parental mAb 3/F11 fully inhibited the binding activity. This proved that the scFv D7 binds to the same PSMA epitope as 3/F11. The scFv D7 and a humanized version thereof were successfully used for the construction of *Pseudomonas* Exotoxin A (PE) based immunotoxins, which showed high and specific cytotoxicity against PSMA-expressing prostate cancer cells and in vivo antitumor activity in mice bearing prostate tumors.

SUMMARY OF THE PRESENT INVENTION

According to the present invention the D7 scFv was used for the construction of chimeric antigen receptors (CAR's) to provide constructs for use in immune cells for targeting cancer cells expressing PSMA.

Ma et al. [The Prostate (2014) 74, pp 286-296] disclose a second generation CAR against PSMA comprising a CD28 costimulatory domain and CD3ζ signaling domains and an antigen binding part from a mouse anti-human PSMA monoclonal antibody 3D8 which is commercially available from Northwest Biopharmaceutics, Inc.

Santoro et al. [Cancer Immunol. Res. (2015), pp 68-84] describe T-cells bearing a chimeric antigen receptor against prostate-specific membrane antigen, whereby the PSMA binding portion is derived from the antibody J591.

Zhong et al. [Molecular Therapy (2010), pp. 413-420] disclose also chimeric antigen receptors whereby the PSMA binding fragment is also derived from the antibody J591. The sequence of J591 is well-known in the art. WO 2009/017823 discloses the VH and VL domains thereof.

The amino acid sequence of the antigen-binding fragment D7 (FIG. 10; SEQ ID NO:1) and the nucleic acid sequence (SEQ ID NO:8), including complementary strand coding for said construct (SEQ ID NO:9), is provided. Moreover, the highly important parts of the antigen-binding fragment, namely the CDRs: (CDR-H1 (SEQ ID NO:2), CDR-H2 (SEQ ID NO:3), CDR-H3 (SEQ ID NO:4), CDR-L1 (SEQ ID NO:5), CDR-L2 (SEQ ID NO:6) and CDR-L3 (SEQ ID NO:7)) are shown and highlighted by grey arrows.

Humanization of murine antibodies involves the transfer of beneficial properties (e.g. antigen-specific binding, avoidance of off-target effects by non-crossreactivity with other antigens) from one antibody to another to reduce immunogenicity. Humanization is usually necessary for human use as patients typically respond with an immune reaction against non-human antibodies that can lead to ineffectiveness of treatment and, in the worst-case scenario, to a life-threatening situation. A humanized construct can be derived from the sequence of the antigen-binding fragment shown in FIG. 10. The CDR regions structurally define the paratope, that is, the contact site of the antigen-binding fragment with the antigen. The remainder of the sequence codes for the framework regions, which form the scaffold of the paratope. For the humanization process (e.g. by in silico modeling), the framework sequence is first compared with other antigen-binding sequences derived from humans. Usually a human sequence (acceptor framework) is selected which has the highest similarity with the framework sequence shown in FIG. 10. The CDR regions are grafted into the human acceptor framework to eliminate amino acid sequences which may cause undesired human anti-mouse-antibody (HAMA) immune reactions. Substitutions at potentially critical positions (e.g. amino acids responsible for folding the paratope or the VH-VL interface) are analyzed for prospective back mutations. Even in the CDR sequences exceptional modifications of amino acids may be made to avoid immunogenicity, to ensure the right folding of the paratope, and to maintain the antigen-specific binding.

In the course of the humanization of antibodies preferably a sequence is selected among human immune sequences which have the highest homology with the corresponding murine sequence. Then the location of the CDRs is determined. The determination of the CDRs is well-known in the art and it should be noted that different methods for the determination are known whereby it is possible that the locations of the CDRs differ somewhat. In the course of the present invention the determination of the CDRs according to Kabat was used and also the determination according to the IMGT (International Immunogene Ticks).

In a preferred embodiment of the present invention the humanization was performed according to the so-called "CDR-grafting". The functional CDRs are determined preferably according the IMGT method and those CDRs are transferred in a human framework region which has the highest sequence homology to the starting murine antibody. Then the differences regarding the single amino acids in the framework region of the humanized and murine antibodies were determined with regard to the biochemical properties like size, polarity or charge. In the first step similar amino acids were adapted and successively the different amino acids were changed in order to end up with a complete human framework.

Since the humanized versions disclosed herein have maintained the CDRs either completely or to a very large extent the humanized variants have the same function of the murine antibody whereby, however, the affinity may differ somewhat from each other.

The results of the humanization experiments are shown in FIG. 11. It turned out that the CDR-H1, CDR-H3 and CDR-L3 should be maintained without any amendment. In the CDR-L2 one amino acid can be replaced which is indicated as X9. X9 may have the meaning of an aliphatic, uncharged amino acid which can be glycine, alanine, valine, lysine, isolysine and/or proline.

In CDR-L1 two amino acids can be replaced which are designated as X7 and X8. Those amino acids can be hydrophilic, uncharged amino acids such as serine, threonine, asparagine and/or glutamine.

The highest flexibility seems to have CDR-H2 wherein up to six amino acids can be replaced. Those amino acids are designated as X1, X2, X3, X4, X5 and X6. The amino acids used for replacement in the humanized antibodies or antigen-binding fragments have the following meaning:

X1, X4, X6: hydrophilic, uncharged amino acids [serine (S), threonine (T), asparagine (N), glutamine (Q)]

X2, X3: aliphatic, uncharged amino acids [glycine (G), alanine (A), valine (V), leucine (L), isoleucine (1), proline (P)]

X5: basic amino acids [histidine (H), lysine (K), arginine (R)].

In recent years, adoptive immune cell therapy has been introduced as a novel concept to treat different cancers by redirecting the immune system to eliminate the tumor cells. One of the most successful concepts is based on the genetic engineering of T cells to express chimeric antigen receptors (CARs) that bind tumor antigens or tumor-associated antigens in a human leukocyte antigen (HLA)-independent manner. CD19 targeting CAR T cells have been successfully used to treat B cell acute lymphoblastic leukemia (B-ALL), with >90% of patients going into complete remission in several clinical trials. Based on this success, more than 200 clinical trials have been initiated to treat mostly hematological malignancies. For solid tumors, however, the potency of CAR T cell therapy seems rather low to date. The main reason for this failure seems to be the tumor microenvironment (TME), which is the cellular environment in which the tumor exists. It includes various kinds of immune cells, fibroblasts, the extracellular matrix (ECM) as well as the surrounding blood vessels. Many mechanisms that describe restriction of cytotoxic T cell activity in the TME have been described, including the activation of PD-1 based T cell immune checkpoint inhibition. Overcoming these restrictions, combined with T cell checkpoint antagonists, will help to improve anti-tumor activity in the TME.

The tumor eradication, as used in the present invention, requires an adequate survival and intratumoral activation of tumor antigen-specific immune cells, preferably T cells. To meet these requirements T cells must be given appropriate activating signals at the time of antigen-priming and stimulation. The chimeric antigen receptors of the present invention combine therefore an antigen-binding fragment as part of the receptor on T cells. The antigen-binding fragment binds to the specific antigen (here PSMA) to which the T cells should bind. Moreover, the receptors contain sequences from CD28 and 4-1BB, respectively, as co-stimulatory signaling domains. It has been shown that the addition of CD28 sequences, or other co-stimulatory signaling domains, to CD3ζ chain-based receptors increases antigen-induced secretion of interleukin-2 and in vitro T cell expansion. In the present case the signaling domain consists of the CD3ζ domain and either the intracellular CD28 or the 4-1BB domain.

In general, the design of a CAR can vary and meanwhile several generations of CARs are known. The main components of a CAR system are the CD3ζ intracellular domain of the T cell receptor (TCR) complex, the transmembrane domain, the hinge region and the antigen-binding part. In the design of a CAR, the antigen-binding domain is linked to a hinge region, which is also called a spacer region, the transmembrane domain, and a cytoplasmic domain. Those parts are responsible for the position of the antigen-binding part, the attachment in T cell membrane, and intracellular signaling. Besides this structural rule in the CAR design the morphological characteristics of the hinge region, such as their length and sequence, are important for an efficient targeting. The intracellular domain acts as a signal transducer. The cytoplasmic segment of the CD3ζ plays the principal rule due to different functions in activated T cells and the resting ones. However, this cytoplasmic part cannot activate the resting T cells alone. Therefore, there is a need of at least a secondary signal for the full activation of T cells. In the present invention, preferably 4-1BB or CD28 co-stimulatory domains were used. Other co-stimulatory domains, such as co-stimulatory domains derived e.g. from CD27, ICOS and OX40, can be used alternatively.

In preferred embodiments mutations are introduced into the human IgG1 Fc hinge region whereby side effects like preventing LcK activation or an unintended initiation of an innate immune response are avoided. One of those mutations avoids LcK binding and another mutation may inhibit the binding of Treg cells to the construct. Such mutations may improve the biological activity of the construct.

For the treatment of human patients, T cells have to be enriched from the individual patient's peripheral blood (autologous setting) or provided by a donor (allogeneic setting). This can be done for example by leukapheresis. The enriched T cells are then transfected or transduced ex vivo with a suitable vector comprising the genetic information for the CAR.

The genetic information coding for the CAR is inserted into a suitable vector. Such vectors are preferably lentiviral or retroviral vectors. A gold standard for transduction of primary T cells are presently considered lentiviral vectors which seem to be a valid alternative to simpler retroviral vectors. As a further alternative to lentiviral vectors the information can be introduced into the T cells with the help of transposons or plasmids. An alternative to both viral and non-viral delivery are the recently described gene editing tools, designated as CRISPR/Cas or other designer nucleases, such as transcription activator-like effector nucleases (TALENs) or zinc finger nucleases (ZFNs). This technology platforms offer the possibility to target virtually any genomic site in a targeted manner. In the case of CRISPR/Cas, the editing complex comprises a Cas nuclease and a guide RNA, usually composed of a CRISPR RNA (crRNA) and a transacting crRNA. Upon hybridization of the guide RNA to the target sequence, Cas9 (or another Cas nuclease, such as e.g. Cpf1/Cas12a) generates a double-strand break, which can be repaired by non-homologous end joining (NHEJ), an event that can result in a loss of function of the genomic locus. In the presence of a suitable donor DNA, by a mechanism of homology-directed repair (HDR), an exogenous sequence (CAR sequence) can be introduced into the targeted locus. This can be exploited to deliver CAR expression cassette in a desired genomic locus that does not interfere with endogenous gene function and therefore minimizing the genotoxic effects experienced with integrating viral vectors. In a further preferred embodiment, genome editing is used to place the CAR coding sequence under control of an endogenous promoter. The expression from an endogenous promoter, such as the promoter of the TRAC locus, could ensure optimal expression levels of the CAR construct to fulfill its function. The nucleic acid sequence coding for the CARs of the present invention is preferably optimized for the human codon usage. Particularly preferred embodiments are SE ID NO:10 coding for the CAR28 construct and SEQ ID NO:11 coding for the CAR41 construct.

In another preferred embodiment of the present invention the RNA coding for the CAR construct is introduced into the target cells, such as T-cells. Nucleic acid coding for the CAR construct may be introduced into the target cells by physical procedures, such as electroporation, or by fusion of the cells' membranes with suitable vesicles. In this embodiment, the CAR construct is preferably transiently expressed in the T-cells. The advantage is that there is then a population of transduced T-cells which is present in the treated patient only for a transient time.

In other preferred embodiments the CAR construct is introduced into natural killer cells (NK), invariant natural killer T-cells (iNKT), diverse natural killer cells (dNKT), cytokine-induced killer cells (CIK) or γ-δ T-cells. Furthermore, suitable allogenic cells may be used.

In a further preferred embodiment, in addition to the CAR construct described herein, another transgene that modulates the immune system, such a genes coding for cytokines, chemokine receptors and/or checkpoint inhibitors, may be introduced in the immune cells. In a further preferred embodiment, genome editing is used to disrupt the expression of genes that modulate the immune system, such as genes coding for cytokines, chemokine receptors and/or checkpoint inhibitors.

In another embodiment the constructs according to the present invention and immune cells containing such constructs can be used for focal therapy with a targeted tumor injection. In this embodiment, which is performed preferably with automated devices that apply the CAR T-cells to certain places in the body of the patient, where local tumor areas are located. With a biopsy needle a sample is then withdrawn whereby a small cavity is formed. In this cavity the transduced or transfected T-cells are introduced and then the needle is withdrawn. This embodiment is particularly advantageous when there are solid tumors which are extremely difficult to treat with regular methods.

The chimeric antigen receptors disclosed herein can be used for the treatment of diseases which are related to the expression of PSMA. PSMA is expressed in tumor cells derived from prostatic cancer. There are several stages of prostatic cancer known, but it seems that PSMA is one of the markers best suited for the treatment of prostate cancer. The term "prostate cancer" comprises all forms of prostate cancer cells either derived from a primary tumor or from a metastatic tumor or from circulating tumor cells. In a particularly preferred embodiment immune cells engineered with the chimeric antigen receptors of the present invention are used against the neovascularization of solid tumors expressing PSMA.

In a further embodiment of the present invention immune cells engineered with the chimeric antigen receptors disclosed herein are used in combination with a therapeutic agent, in particular a cytotoxic agent. Cytotoxic agents as used for the treatment of prostate cancer are known. Preferably such substances comprise taxol derivatives, 5-fluorouracil, cyclophosphamide, mitoxantrone, docetaxel, cabazitaxel and etoposide. The following drugs are approved for prostate cancer and preferably used: Abiraterone Acetate, Apalutamide, Bicalutamide, Cabazitaxel, Casodex (Bicalutamide), Degarelix, Docetaxel, Eligard (Leuprolide Acetate), Enzalutamide, Erleada (Apalutamide), Firmagon (Degarelix), Flutamide, Goserelin Acetate, Jevtana (Cabazitaxel), Leuprolide Acetate, Lupron Depot (Leuprolide Acetate), Mitoxantrone Hydrochloride, Nilandron (Nilutamide), Nilutamide, Provenge (Sipuleucel-T), Radium 223 Dichloride, Sipuleucel-T, Taxotere (Docetaxel), Xofigo (Radium 223 Dichloride), Xtandi (Enzalutamide), Zoladex (Gosereliin Acetate), Zytiga (Abiraterone Acetate). It is understood that the chimeric antigen receptors of the present invention can also be used in combination with a medicament used to treat hormone sensitive forms of prostate cancer like for example Leuprolide Acetate.

The preferred embodiments of the present invention are further described and illustrated in the Figures and Examples of the present application. All aspects disclosed in the Figures or the examples, respectively, relate to the present invention unless expressly excluded. The single features of the present invention as disclosed in the experimental part can be combined unless there are technical reasons which speak against such combination. In particular, the Figures show the results of the experiments as follows:

BRIEF DESCRIPTION OF THE FIGURES

In the Figures and in the experiments the following abbreviations were used.

| Abbreviation | Explanation |
|---|---|
| 4-1BB | tumor necrosis factor receptor superfamily member 9 |
| BLI | bioluminescence imaging |
| bw | body weight |
| C4-2 | PSMA positive prostate cancer cell line |
| CAR | Chimeric Antigen Receptor |
| CAR28 | anti-PSMA CAR with CD28 co-stimulatory domain |
| CAR41 | anti-PSMA CAR with 4-1BB co-stimulatory domain |
| CD28 | cluster of differentiation 28 |
| CD3ζ | CD3 zeta region |
| CD45RA | cluster of differentiation 45 isoform RA |
| CD62L | cluster of differentiation 62, L-selectin |
| CR | complete remission |
| DOC | docetaxel |
| DU 145 | PSMA negative prostate cancer cell line |
| EFS | Short version of the elongation factor alpha gene promoter |
| ELISA | enzyme-linked immunosorbent assay |
| i.v | intravenously |
| i.p. | intraperitoneally |
| s.c. | subcutaneously |
| Gr. A | Granzyme A |
| Gr. B | Granzyme B. |
| IFN-g | Interferon-gamma |
| LTR | long terminal repeat of retroviral vector |
| PR | partial remission |
| R | R region of the retroviral long terminal repeat |
| scFv | single chain variable fragment |
| SD | standard deviation |
| Tcm | T cell central memory |
| Teff | T cell effector |
| Tem | T cell effector memory |
| Tn, scm | T cell naïve or T stem cell memory |
| U5 | U5 region of the retroviral long terminal repeat |
| UT | untransduced T cell |
| WPRE | woodchuck hepatitis virus post-transcriptional regulatory element |
| XTT | sodium 3'-[1-(phenylaminocarbonyl)-3,4-tetrazolium]-bis(4-methoxy-6-nitro) benzene sulfonic acid hydrate |
| ΔU3 | deletion in the U3 region in the retroviral long terminal repeat |

(A) Schematic of self-inactivating gamma-retroviral vectors to express 2$^{nd}$ generation anti-PSMA CARs. CAR expression is driven by an EFS promoter. The CAR consists of a single chain variable fragment D7 (derived from 3F/11 murine monoclonal antibody against PSMA), a hinge region (not shown), a transmembrane domain, a costimulatory domain either derived from 4-1BB (CAR41) or CD28 (CAR28), and an intracellular signaling domain derived from CD3ζ chain. The hinge region, which is included in both CARs, is derived from human IgG and provides a physical spacer between the D7-scFv and the transmembrane domain for optimal target recognition.

(B) CAR expression. T cells were activated for 2-3 days with anti-CD2/3/28 antibodies prior to retrovirus transduction. Following viral transduction, T cells were expanded for 8-9 days before cells were harvested and stained with anti-human IgG antibody (CAR) and CD3 to evaluate the transduction efficiencies.

(C) Qualitative CAR T cell phenotype characterization with flow cytometric analysis. T cell subsets were evaluated by assessing the expression of CD62L and CD45RA, pre-gated on CAR-CD3+ for the untransduced T cells (UT) (not shown) or CAR+CD3+ for both types of CAR T cells (not shown).

(D) Qualitative assessment of CAR T cell phenotype. Shown are the average percentages of the different T cell subsets from at least three independent experiments. PSMA, prostate specific membrane antigen; scFv, single chain variable fragment; EFS, elongation factor 1 alpha short promoter; Tn/Tscm, T cell naïve or T stem cell memory; Tcm, T cell central memory; Tem, T cell effector memory; Teff, T cell effector.

This characterization of the CAR T cell phenotype confirms that the chosen CAR design enables the generation of high-quality of CAR T cell products with a minimal amount of terminally differentiated T cell subsets.

Figure 2:
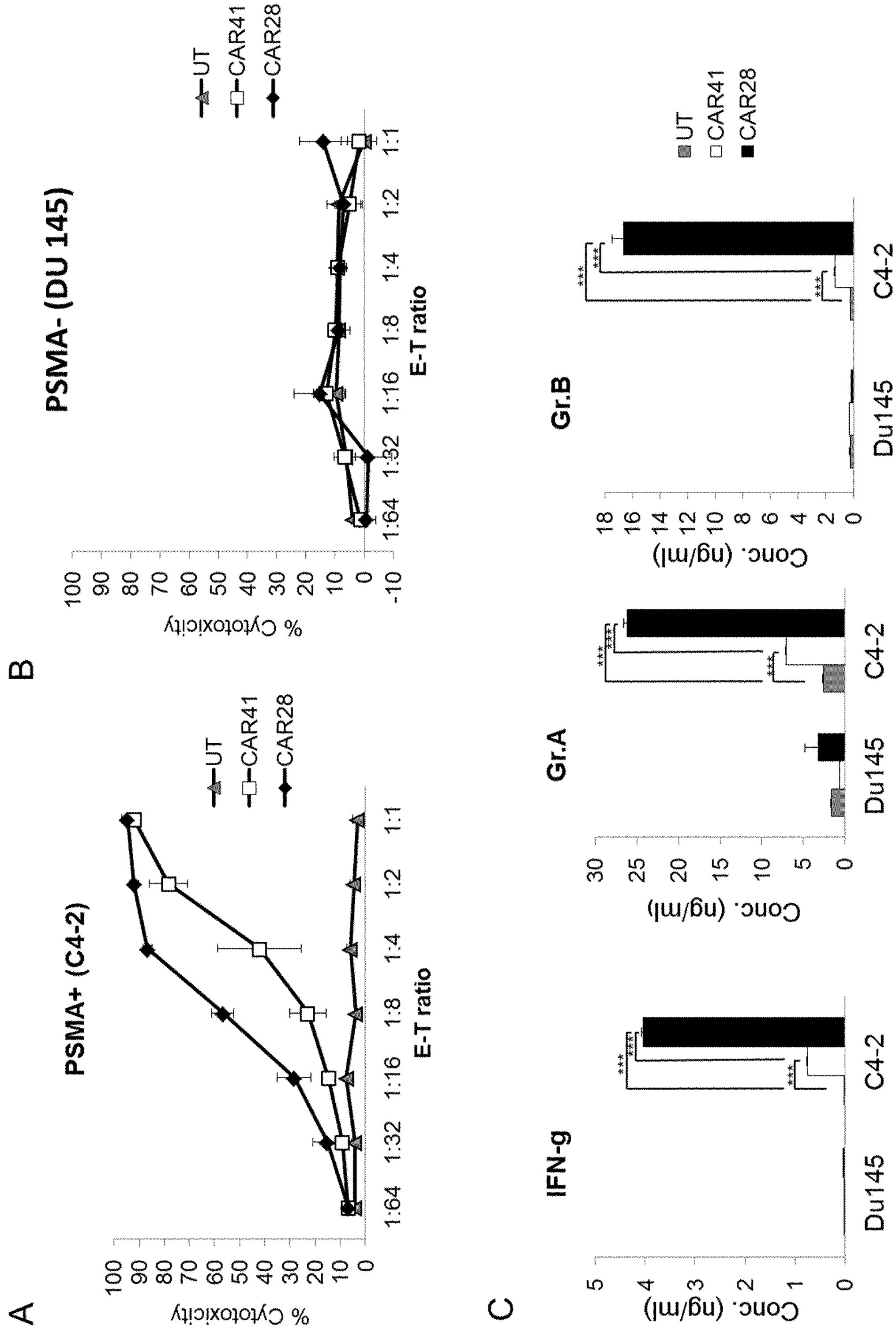

FIG. 2. Cytotoxicity and cytokine release of PSMA-CAR T cells.

(A) Cytotoxicity profile of CAR T cells on PSMA positive C4-2 tumor cells. CAR T cells were co-cultured for 48 hours at different effector to target (E:T) ratios, with either antigen positive C4-2 tumor cells or PSMA negative cells (DU145) were used.

(B) Cytotoxicity of CAR T cells on PSMA-negative DU 145 tumor cells. CAR-T cells were co-cultured for 48 hours at different effector to target (E:T) ratios with DU145 cells.

Cytotoxicity was measured by an XTT ELISA based colorimetric assay (% cytotoxicity=100−% viability).

A comparison of the results as presented in FIG. 2A and FIG. 2B shows that the T cells transfected with the CAR, according to the invention, have a cytotoxic activity only with the cell line expressing the PSMA antigen since in panel A a PSMA expressing cell line (C4-2) was used. When the cell line does not express PSMA, as for example cell line DU 145, no cytotoxicity can be seen with the CAR T cells (FIG. 2B). Furthermore, the CAR28 and CAR41 cells of this invention showed superior cytotoxicity as compared to previously published data (PMID 16204083, PMID: 18026115, PMID: 19773745, PMID: 25358763, PMID: 23242161, PMID: 4174378, PMID: 25279468): up to 90% of PSMA expressing cells were eliminated (FIG. 2A), using a low E:T ratio of 1:1. The observed high in vitro cytotoxicity with a low E:T ratio of 1:1 is unique and was not described in any of the available PSMA-CARs so far, indicating the superior performance our CAR T cells based on the scFv D7.

(C) Quantification of pro-inflammatory cytokine release upon antigen stimulation. CAR T cells were stimulated with either PSMA-positive C4-2 cells or PSMA-negative DU 145 cells for 48 hours. Cytokines in supernatant were quantified by flow cytometry based cytokine-bead assay. Statistically significant differences are indicated by ***(P<0.001; n=3). UT; untransduced T cells, IFN-g; interferon gamma, Gr.A; Granzyme A, Gr.B; Granzyme B.

It can be seen from FIG. 2C that pro-inflammatory cytokine release occurred only when CAR T cells were co-cultured with cell lines expressing PSMA (cell line: C4-2). CAR28 were activated to a higher extend than CAR41 cells.

Figure 3:
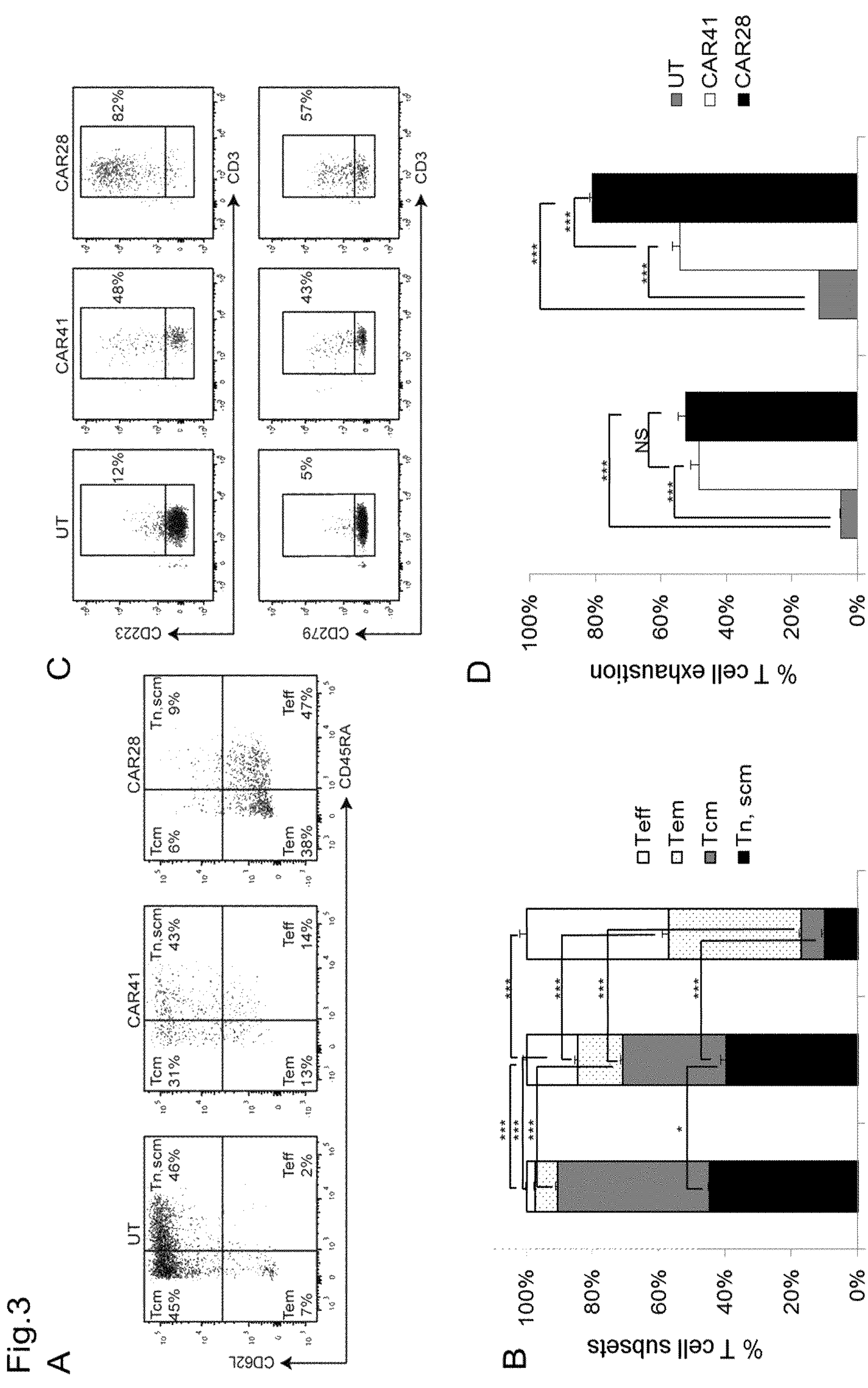

FIG. 3. CAR T cell phenotype and exhaustion profiles upon antigen specific stimulation.

(A) CAR T cell phenotype. CAR T cells were stimulated with PSMA-positive C4-2 tumor cells for 24 hours at a 1:1 effector-to-target (E:T) ratio before T cell phenotype profile was assessed based on the expression of CD62L and CD45RA. Cells were pre-gated on either CAR-CD3+ for UT control (not shown) or CAR+CD3+ for both types of CAR T cells (not shown).

(B) Quantitative assessment of CAR T cell phenotype. Shown are the average percentages of the different T cell subsets from three independent experiments. Statistical significant differences are indicated by ***(P<0.001) or *(P<0.05).

(C) T cell exhaustion profile. CAR T cells were stimulated with PSMA-positive tumor cells (C4-2) for 24 hours before T cell exhaustion profile was assessed by measuring the expression of CD223 (LAG-3) and CD279 (PD-1). Cells were pre-gated on CAR-CD3+ for UT control (not shown) or CAR+CD3+ for both types of CAR T cells (not shown).

(D) Quantitative assessment of CAR T cell exhaustion profiles. Shown are the average percentages of PD-1 or LAG-3 positive cells (three independent experiments). Statistically significant differences are indicated by *** (P<0.001). NS, not significant; UT, untransduced T cells; Tn/Tscm, T cell naïve or T stem cell memory; Tcm, T cell central memory; Tem, T cell effector memory; Teff, T cell effector; LAG-3, lymphocyte activation gene 3; PD-1, programmed cell death protein 1.

This set of experiments addressed the T cell phenotype and the exhaustion profiles of the CAR41 and CAR28 T cells upon antigen-specific stimulation. As seen in panels 3A and 3B, in contrast to CAR28 cells, a high percentage of CAR41 cells preserved an undifferentiated T cell phenotype upon antigen-specific stimulation. Furthermore, the CAR41 cells were less sensitive to exhaustion as compared to CAR28 T cells upon antigen-specific differentiation (FIGS. 3C and 3D).

Figure 4:
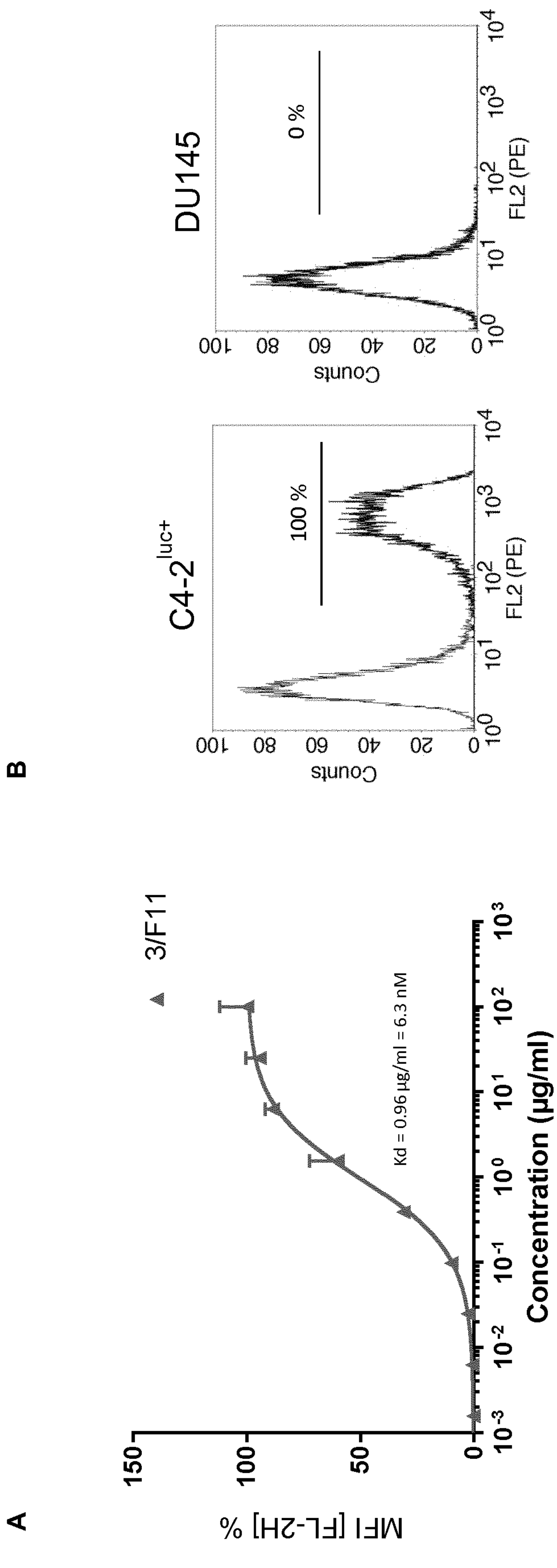

FIG. 4: PSMA expression of the prostate cancer target cell line C4-$2^{luc+}$.

For in vivo bioluminescence imaging, PSMA-positive prostate cancer C4-2 cells were transduced with a lentiviral vector encoding firefly luciferase, a neomycin resistance gene and green-fluorescent protein (GFP). The transduced cell line was named C4-$2^{luc+}$.

(A) Binding of the anti-PSMA mAb 3/F11 to C4-$2^{luc+}$ cells as determined by flow cytometry.

(B) Binding at a saturation concentration of 25 μg/ml 3/F11 to C4-$2^{luc+}$ and PSMA-negative DU 145 cells as determined by flow cytometry.

Binding of the anti-PSMA mAb 3/F11, the parental mAb of the scFv D7, verified the PSMA expression on the surface of all C4-$2^{luc+}$ prostate cancer target cells, while DU 145 prostate cancer control cells were shown to be PSMA negative.

Figure 5:
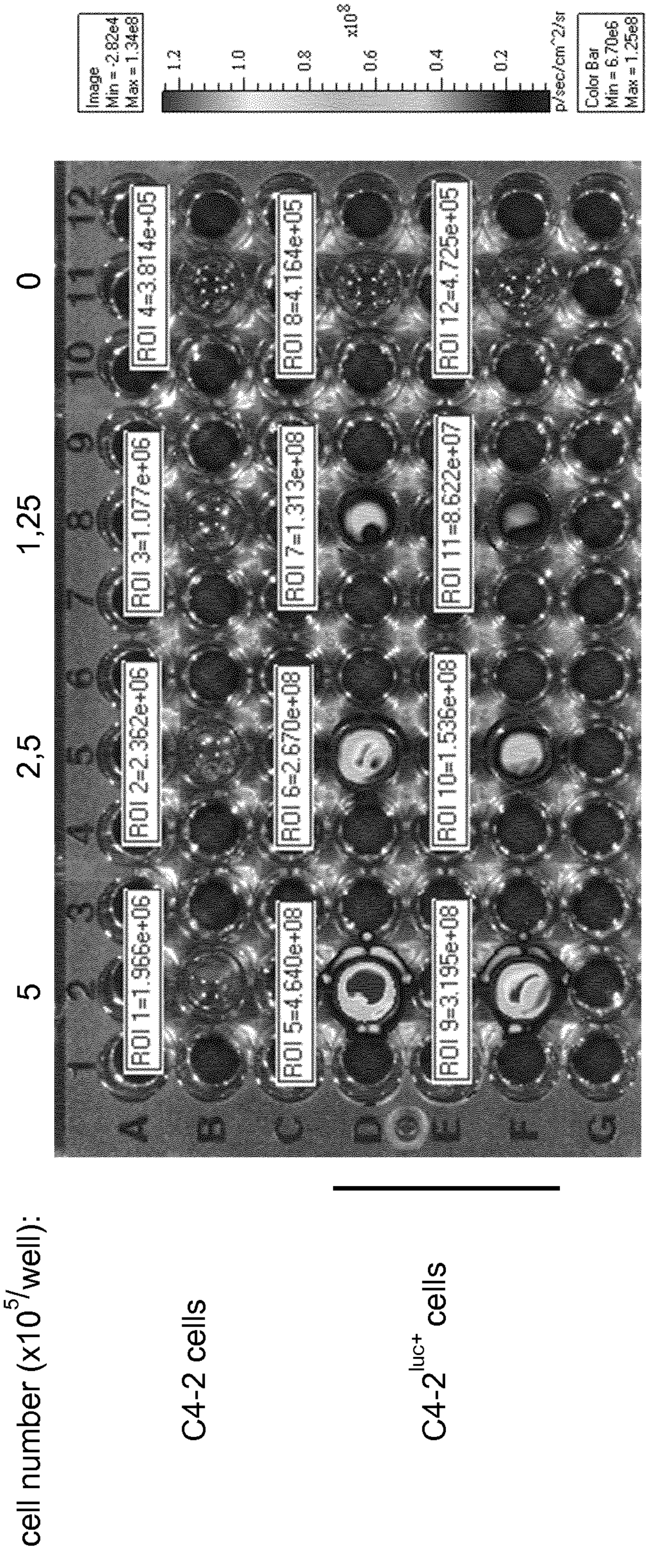

FIG. 5: Bioluminescence of C4-$2^{luc+}$ cells as determined by bioluminescence imaging (BLI) with the Living imaging system IVIS 200 (Xenogen VivoVision).

The luminescence of the C4-$2^{luc+}$ target cells was tested using the In Vivo Imaging System IVIS 200 (Xenogen VivoVision) after incubation with luciferin. Compared to the non-transduced C4-2 cells, the C4-$2^{luc+}$ cells showed bioluminescence, with an intensity (photons/sec/$cm^2$) that was linear to the cell number. Thus, these cells were suitable for their use in the mouse tumor xenograft model with tumor detection by bioluminescence imaging (BLI). ROI, region of interest.

Figure 6:
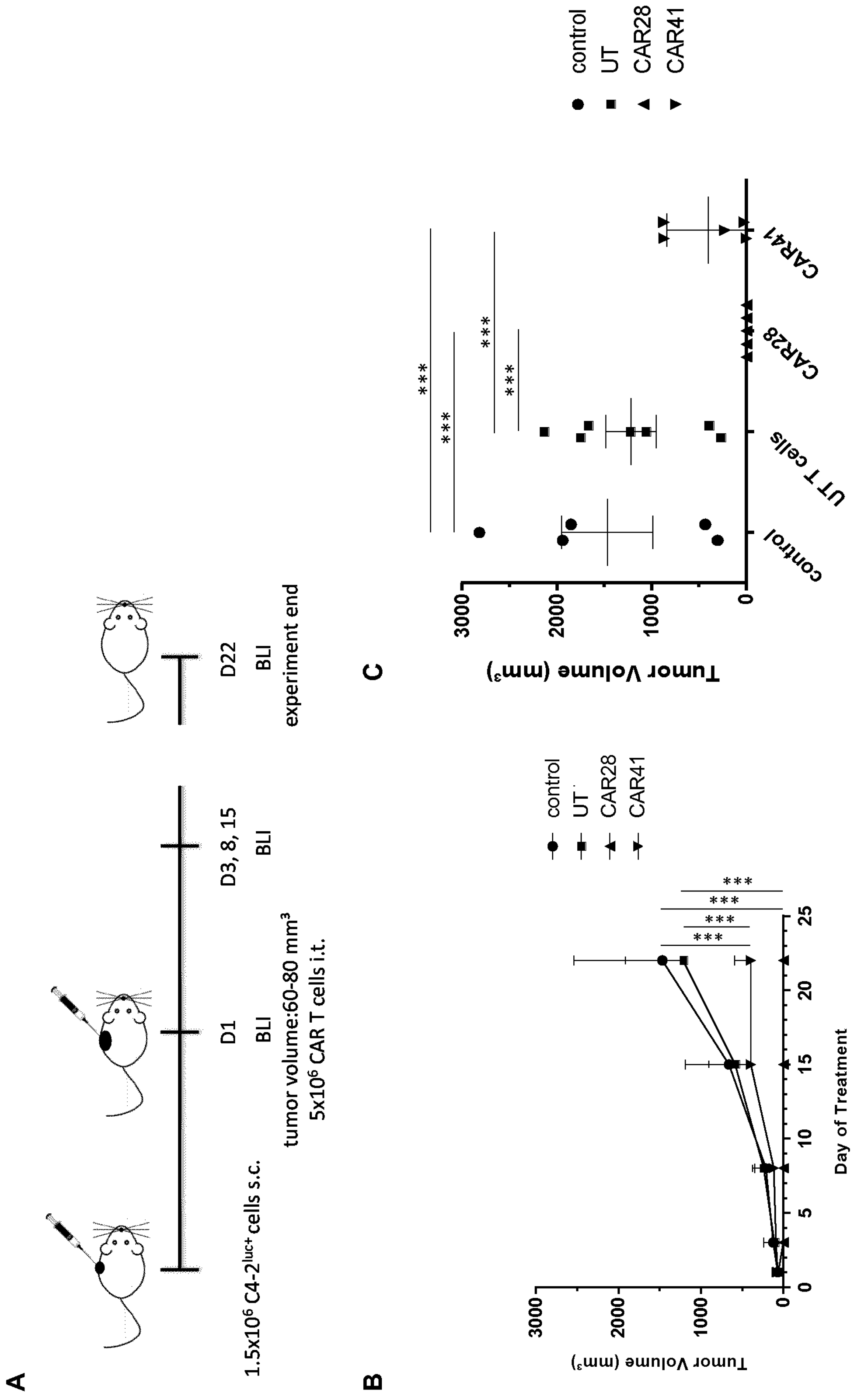
Figure 6:
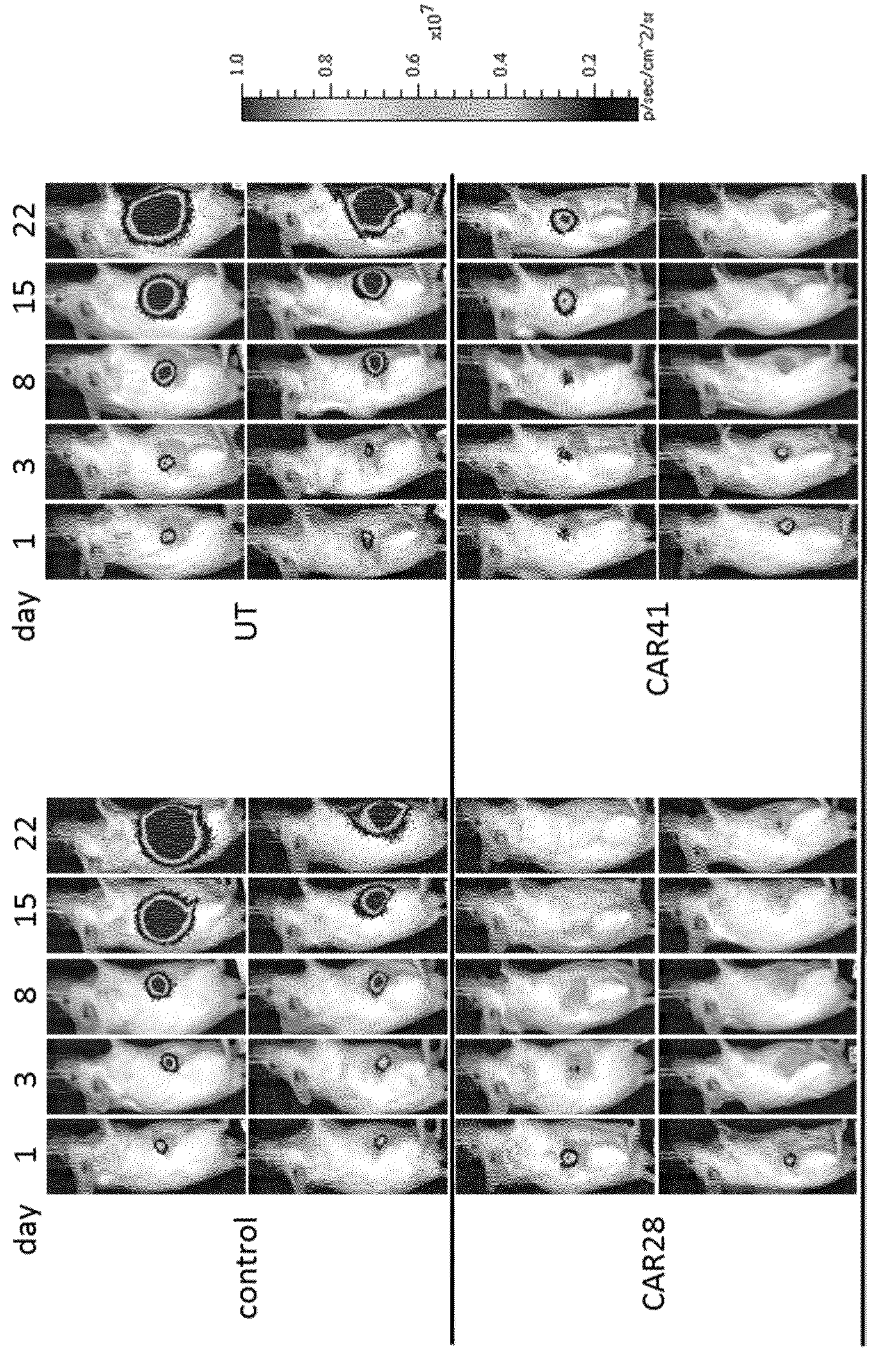

FIG. 6 Intratumoral CAR T cell therapy (A) Schematic of intratumoral CAR T cell therapy. Tumor engraftment was established in animals by subcutaneous injection of 1.5×$10^6$ cells. When the growing solid C4-$2^{luc+}$ tumors have reached 60-80 $mm^3$ volume, CAR T cells were intratumorally injected with single doses of 5×$10^6$ CAR28 (n=5) or CAR41 T cells (n=5) at day 1 of treatment. Control mice were injected with the same number of UT cells (n=7) or left untreated (control, n=6). Tumors were visualized by bioluminescence imaging (BLI) until the end of treatment at day 22. D, day; i.t, intratumoral; s.c, subcutaneous.

(B) Antitumor activity of CAR28 and CAR41 T cells after intratumoral injection. Animals with subcutaneously growing solid C4-$2^{luc+}$ tumors (60-80 $mm^3$ volume) were intratumorally injected with single doses of 5×$10^6$ CAR28 (n=5) or CAR41 T cells (n=5) on day 1 of treatment. Control mice were injected with the same number of UT cells (n=7) or left untreated (control, n=6). Tumors were visualized by BLI until the end of treatment on day 22. Tumor volumes, represented as Mean±SD were calculated from the BLI images using the formula Vol=$d^2$×D/2, where d was the small diameter and D was the large diameter of the tumor. Statistical significant differences are indicated by ***p<0.001.

(C) Antitumor activity of intratumorally injected CAR28 and CAR41 T cells at the end of treatment (day 22). Tumor volumes were calculated from BLI images as described above. Tumor volumes are shown as Mean±SD. Statistical significant differences are indicated by ***p<0.001. Since 1/6 mice of the control group developed an ulcerating tumor, this mouse had to be euthanized on day 15 and was not included into the statistical analysis of day 22.

(D) Representative bioluminescence images of mice intratumorally treated on day 1 of treatment with single injections of CAR28 or CAR41 T cells compared to untreated animals (control) or animals treated with UT T cells. Two mice representing animals with large or small tumors of each treatment group are shown.

Intratumoral treatment of mice bearing solid C4-$2^{luc+}$ tumors of 60-80 $mm^3$ volume with one injection of 5×$10^6$ CAR28 T cells on day 1 of treatment led to a significant inhibition of tumor growth and to 5/5 complete tumor remissions (CR) until day 15 (FIGS. 6B, C and D). One animal showed a recurrence of the tumor at day 22 with a tumor end volume of 0.55 $mm^3$ (FIG. 6D, mouse pictured). For all mice of the group a mean tumor volume of 0.11±0.22 $mm^3$ was calculated for day 22 (FIGS. 6B and C). Mice intratumorally treated with CAR41 T cells showed a different response. 1/5 CR and 1/5 partial remission (PR) were noted leading to a statistically significant inhibition of tumor growth with a mean tumor end volume of 397.3±393.6 $mm^3$ on day 22 (FIGS. 6B and C). In contrast, all mice of the UT and control groups showed tumor progression leading to tumor end volumes of 1469.4±961.5 $mm^3$ and 1289.1±636.8 $mm^3$, respectively (FIGS. 6B and C).

Figure 7:
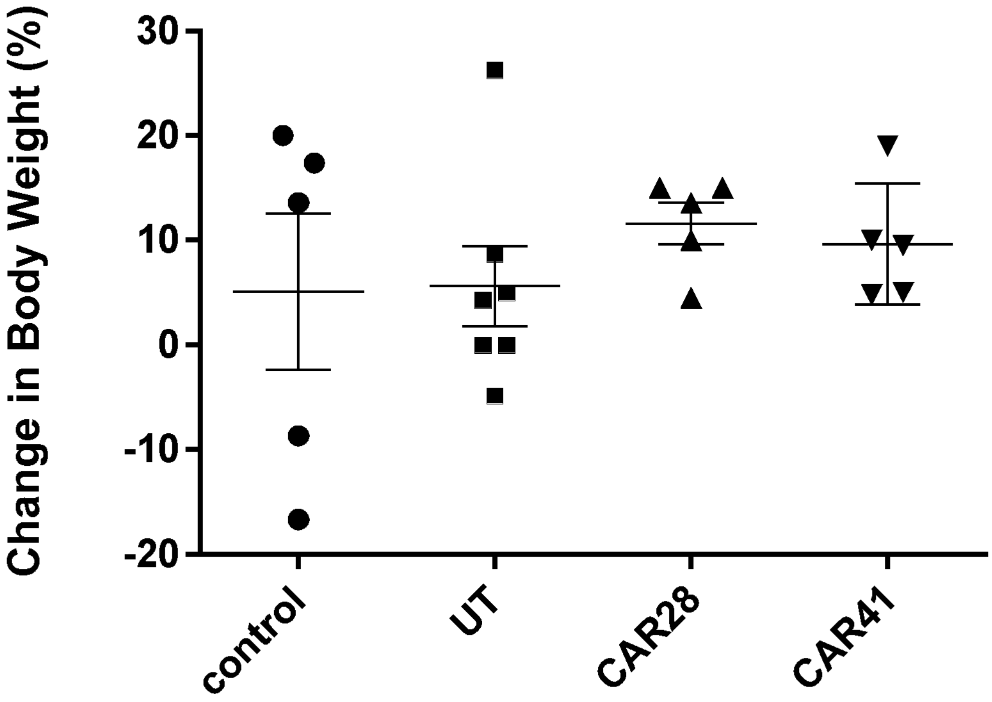

FIG. 7: Changes in body weight of intratumorally treated mice at the end of treatment (day 22).

According to animal protection guidelines, a decrease in body weight is an essential sign of toxicity during treatment. No animal showed a critical decrease of its initial body weight of more than 20%. This evidences that the intratumoral treatment was tolerated well without apparent signs of off-target toxicity.

Figure 8:
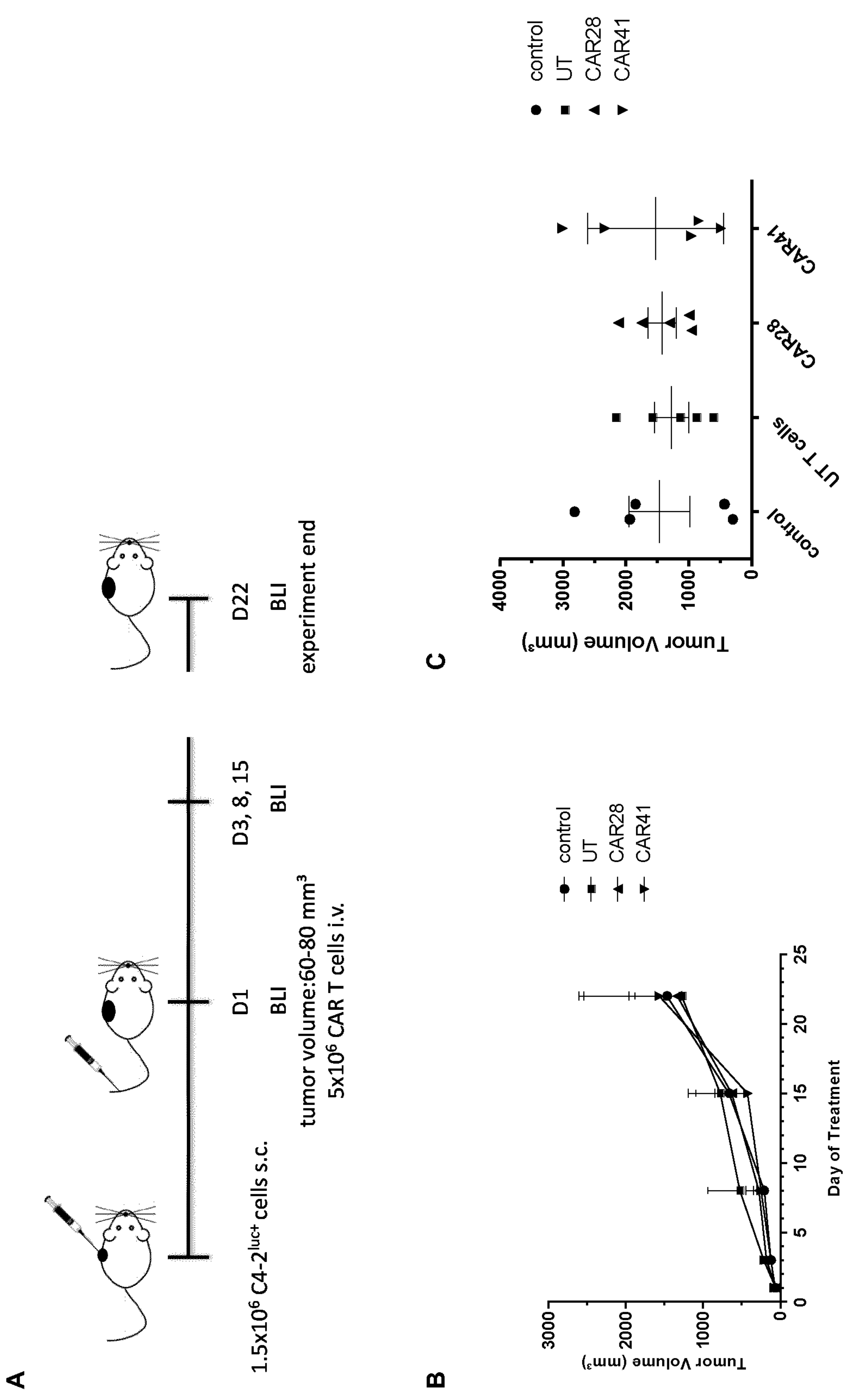
Figure 8D:
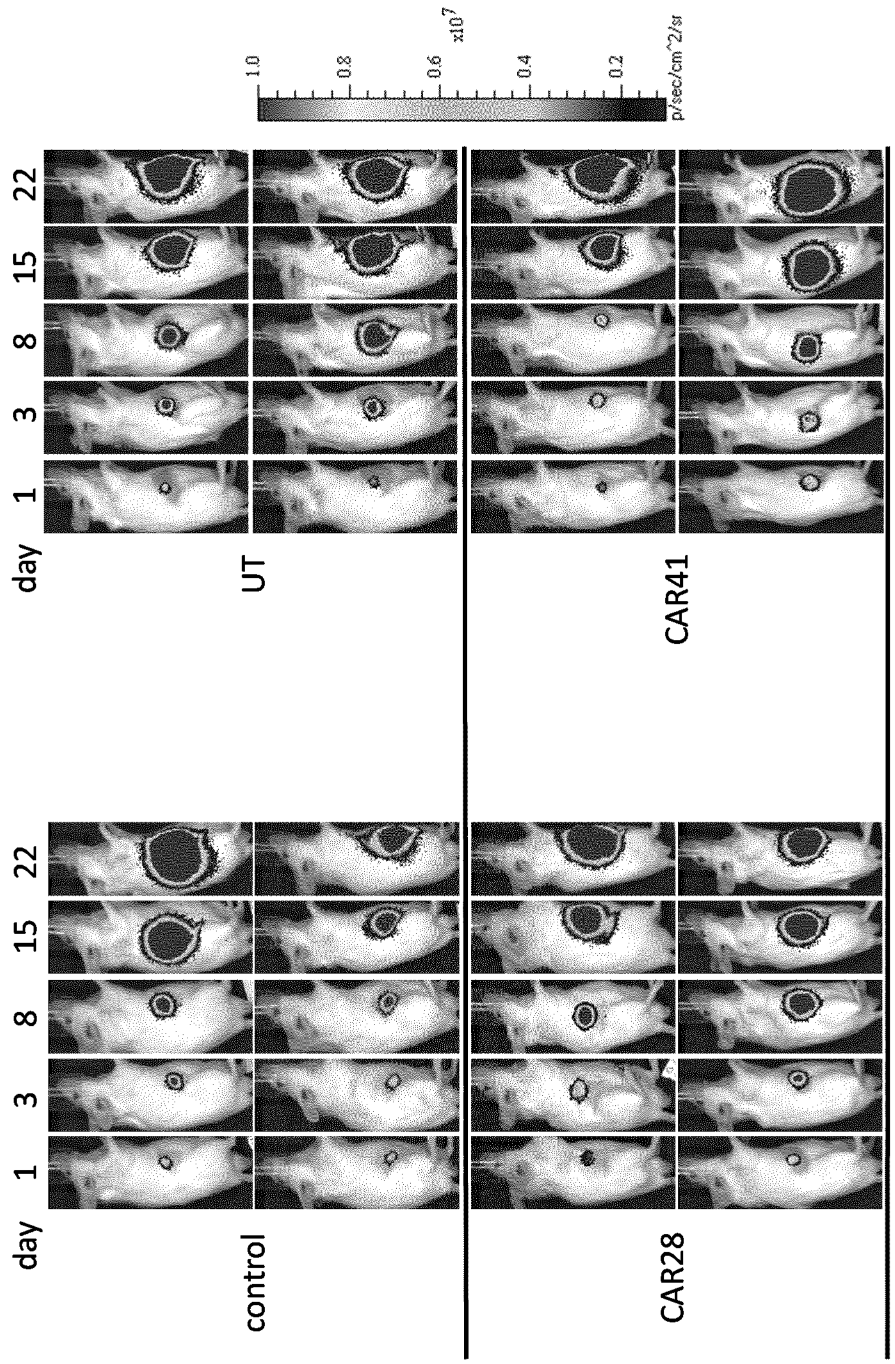

FIG. 8: Intravenous CAR T cell therapy.

(A) Schematic of intravenous CAR T cell therapy. Tumor engraftment was established in animals by subcutaneous injection of 1.5×$10^6$ cells. When the growing solid C4-$2^{luc+}$ tumors have reached 60-80 $mm^3$ volume, CAR T cells were intravenously injected with single doses of 5×$10^6$ CAR28 (n=5) or CAR41 T cells (n=5) on day 1 of treatment. Control mice were injected with the same number of UT cells (n=7) or left untreated (control, n=6). Tumors were visualized via BLI until the end of treatment on day 22. D, day; i.v, intravenous; s.c, subcutaneous.

(B) Antitumor activity of CAR28 and CAR41 T cells after intravenous injection. Animals with subcutaneously growing solid C4-$2^{luc+}$ tumors (60-80 $mm^3$ volume) were intravenously injected with single doses of 5×$10^6$ CAR28 (n=5) or CAR41 T cells (n=5) at day 1 of treatment. Control mice were injected with the same number of untransduced T cells (UT cells) (n=5) or left untreated (control, n=6). Tumors were visualized via bioluminescence imaging until the end of treatment on day 22. Tumor volumes, represented as Mean±SD were calculated from the BLI images using the formula Vol=$d^2$×D/2, where d was the small diameter and D was the large diameter of the tumor.

(C) Antitumor activity of intravenously injected CAR28 and CAR41 T cells at the end of treatment (day 22). Tumor volumes were calculated from BLI images as described above. Tumor volumes are shown as Mean±SD.

(D) Representative bioluminescence images of mice intravenously injected with single doses of CAR28 or CAR41 T cells. Two mice representing animals with large or small tumors of each treatment group are shown.

No inhibition of tumor growth could be measured after single intravenous injections of CAR28 or CAR41 T cells into mice bearing solid tumors with volumes of 60-80 $mm^3$ (FIGS. 8B and C). As demonstrated in FIG. 8C+D, animals of all treatment groups showed comparable tumor growth leading to tumor end volumes on day 22 of 1469.4±961.4 $mm^3$ (control), 1275.7±544.5 $mm^3$ (UT), 1427.3±448.5 $mm^3$ (CAR28), and 1529.3±971.0 $mm^3$ (CAR41).

Figure 9:
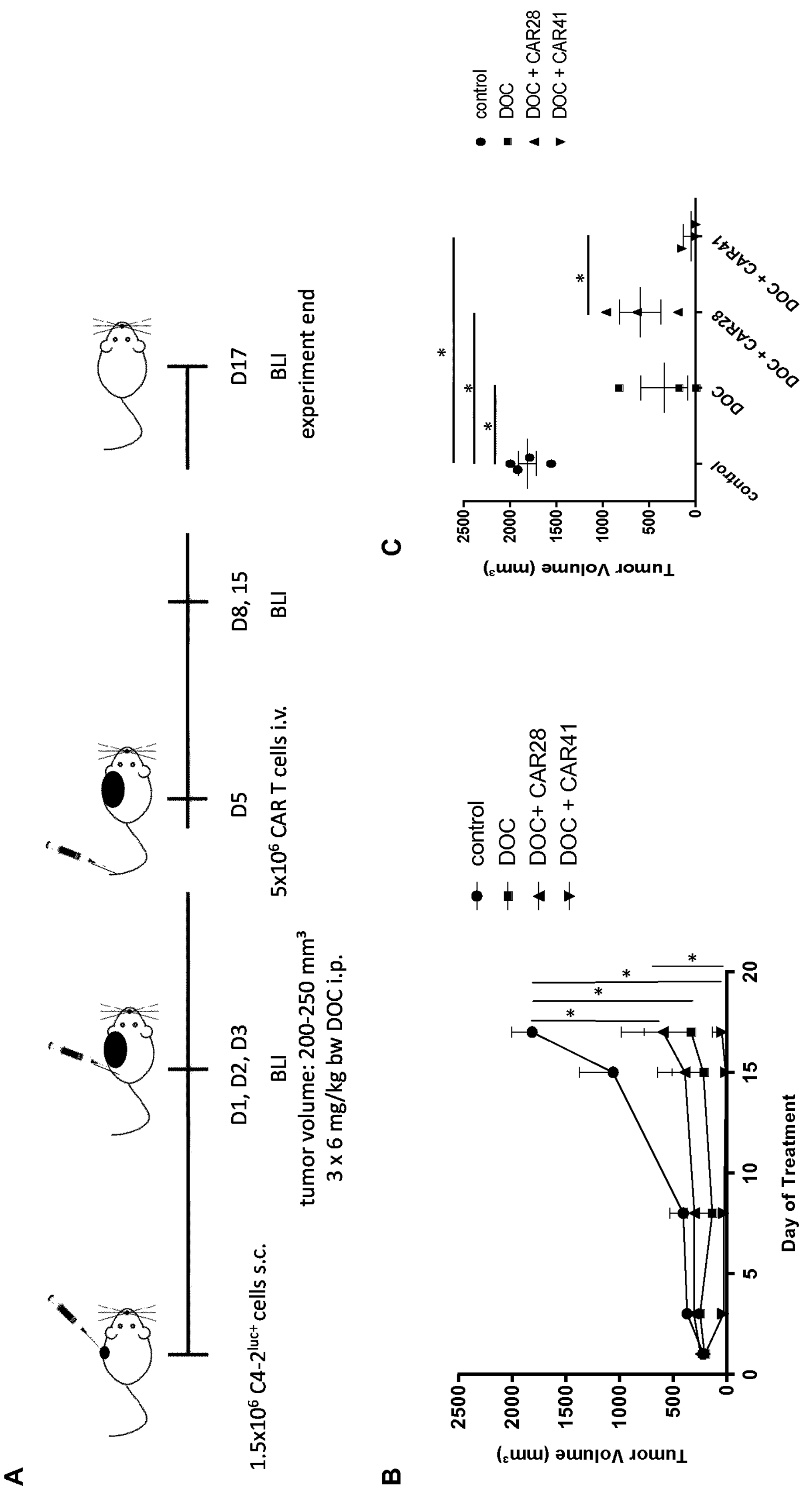
Figure 9:
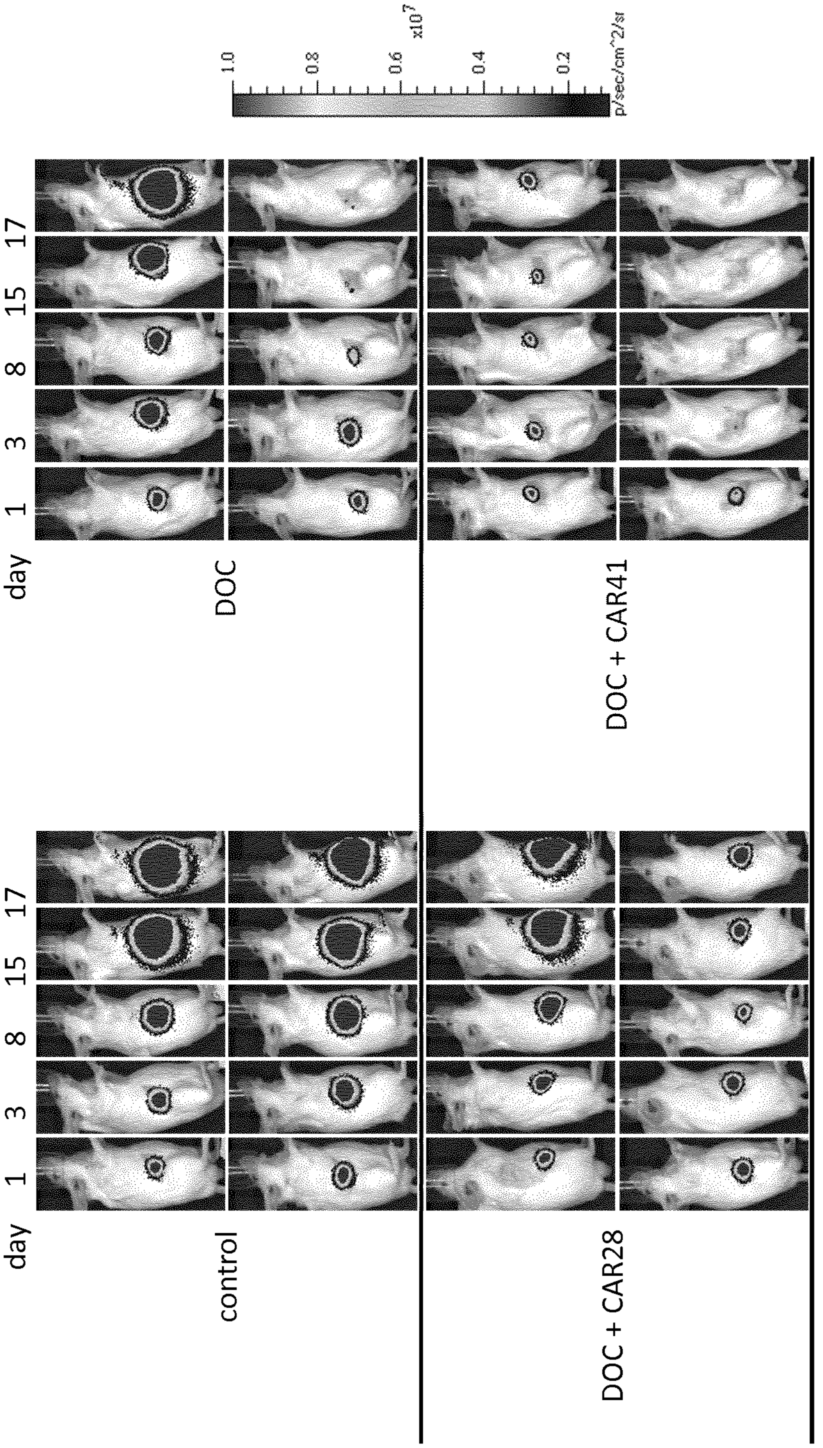

FIG. 9: Combination therapy (A) Schematic of combined chemotherapy with intravenous CAR T cell therapy. Tumor engraftment was established in animals by subcutaneous injection of 1.5×$10^6$ cells. Chemotherapy had started at day 1 of the treatment for 3 days by intraperitoneal injection of docetaxel (DOC, 6 mg/kg bw). 48 hours after the last chemotherapy cycle, mice were injected intravenously with single doses of 5×$10^6$ CAR28 (n=3) or CAR41 T cells (n=3). Control mice were injected with docetaxel alone (n=3) or left untreated (control, n=4). Tumors were visualized via BLI until the end of treatment at day 17. D, day; i.v, intravenous injection; i.p, intraperitoneal; s.c, subcutaneous.

(B) Antitumor activity of CAR28 and CAR41 T cells in combination with docetaxel chemotherapy. Mice with subcutaneously growing C4-$2^{luc+}$ tumors (200-250 $mm^3$) were intraperitoneally injected with docetaxel (DOC; 6 mg/kg bw) on days 1, 2, and 3 of treatment. 48 hours later mice were additionally injected with a single dose of 5×$10^6$ CAR28 (n=3) or CAR41 T cells (n=3) intravenously. Tumor growth was monitored by BLI. Compared to the untreated control (n=4), DOC treatment led to a significant inhibition of tumor growth, which was enhanced by the addition of CAR28 or CAR41 T cells. 4/4 mice of the control group showed growing tumors during treatment, whereas in the DOC group 2/3 mice showed a PR. In the DOC+CAR28 group 1/3 animals showed a PR. In the DOC+CAR41 group 2/3 mice showed a CR and 1/3 mice a PR. A statistically significant difference between the DOC+CAR28 and DOC+CAR41 groups demonstrated the superior effects of the CAR41 T cells in this treatment scheme. Statistical significant differences are indicated by $*p<0.05$.

(C) Antitumor activity of CAR28 and CAR41 T cells in combination with docetaxel chemotherapy on day 17 of treatment. At the end of treatment on day 17 the mean tumor volume of mice of the control group was determined with 1817.5±165.5 $mm^3$. The DOC group and the DOC+CAR28 group exhibited significantly lower volumes of 338.3±355.6 $mm^3$ and of 559.9±317.2 $mm^3$, respectively. Animals of the DOC+CAR41 group only had a mean tumor volume of 50.2±71.1 $mm^3$. Statistical significant differences are indicated by $*p<0.05$.

(D) Representative bioluminescence images of mice pretreated with DOC and intravenously injected with single doses of CAR28 or CAR41 T cells. Two mice representing animals with large or small tumors of each treatment group are shown.

Taken together, pretreatment of tumors with docetaxel chemotherapy led to an antitumor activity of intravenously applicated CAR41 T cells.

FIG. 10: Sequences

FIG. 10 shows the amino acid sequence ("Frame1") of the antigen-binding construct D7 which is derived from mice. Moreover, the coding nucleic acid sequence and the complementary strand thereof are provided. The CDR H1-H3 and CDR L1-L3 nucleic acid and amino acid sequences are marked with grey arrows.

The amino acid sequence of the ScFv fragment of D7 (SEQ ID NO:1) is essential for the present invention insofar as it is the starting sequence for the humanization of the antigen binding fragment. The humanized sequences have a homology of at least 80% to SEQ ID NO:1. In a more preferred embodiment the sequences have a homology of at least 90% and more preferred at least 95% to SEQ ID NO:1 and even more preferred the homology is at least 98% to SEQ ID NO:1. It should be noted that the CDR regions which are shown in FIG. 10 are conserved to a very high level which means that the CDR regions which are determined by the Kabat method have not more than three, preferably not more than one and preferably no amino acid exchange.

Figure 14A:
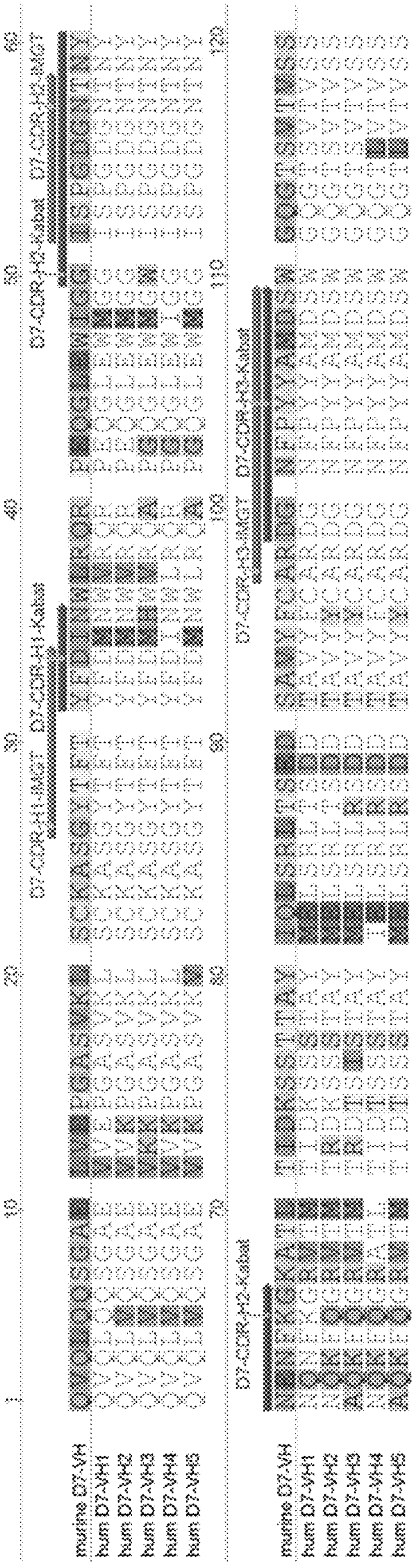
Figure 14B:
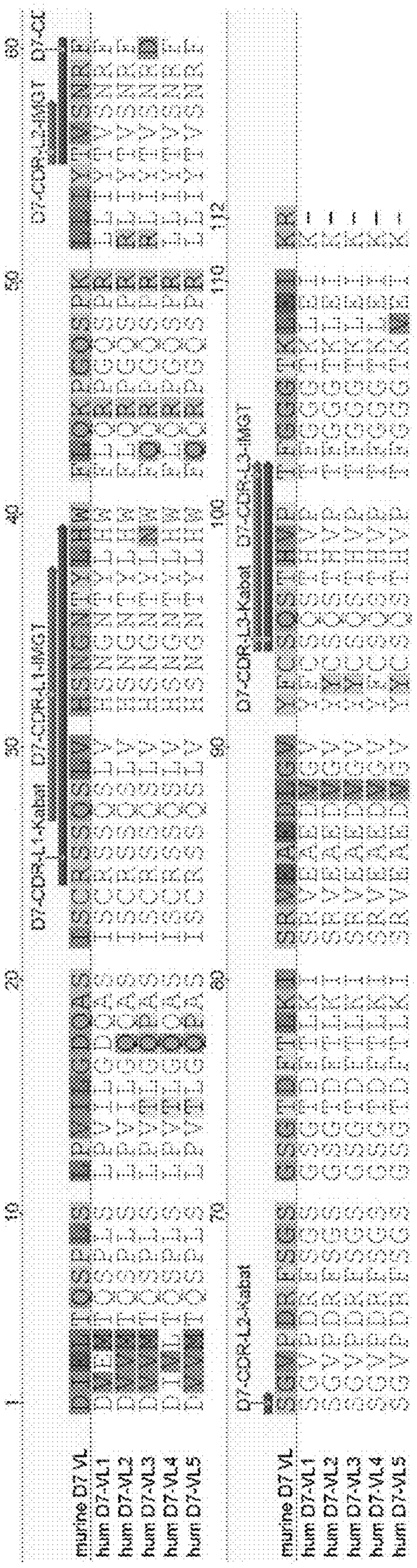

The sequences as disclosed in the present application are summarized as follows:

| SEQ ID NO: | nucleic/amino acid | description | |
|---|---|---|---|
| 1 | amino acid | antigen binding fragment D7 | FIG. 10 |
| 2 | amino acid | CDR-H1 (YFDIN) | FIG. 10, 11 |
| 3 | amino acid | CDR-H2 (GISPGDGNTNYNENFKG) | FIG. 10, 11 |
| 4 | amino acid | CDR-H3 (DGNFPYYAMDS) | FIG. 10, 11 |
| 5 | amino acid | CDR-L1 (RSSQSLVHSNGNTYLH) | FIG. 10, 11 |
| 6 | amino acid | CDR-L2 (TVSNRFS) | FIG. 10, 11 |
| 7 | amino acid | CDR-L3 (SQSTHVPT) | FIG. 10, 11 |
| 8 | coding sequence | D7 | codon optimized for bacterial expresson |
| 9 | complementary strand | D7 | codon optimized for bacterial expression |
| 10 | coding strand | CAR 28 | FIG. 12 |
| 11 | coding strand | CAR 41 | FIG. 13 |
| 12 | nucleic acid | coding strand D7 | FIG. 10 |
| 13 | nucleic acid | complementary strand D7 | FIG. 10 |
| 14 | amino acid sequence | chimeric antigen receptor | FIG. 12 |
| 10 | coding sequence | with fragment of CD 28 | FIG. 12 |
| 16 | complementary strand | | FIG. 12 |
| 17 | amino acid sequence | chimeric antigen receptor | FIG. 13 |
| 11 | coding sequence | with fragment of 4-1 BB | FIG. 13 |
| 19 | complementary strand | | FIG. 13 |
| 20 | amino acid | D7 VH murine (complete) | FIG. 14a |
| 21 | amino acid | hum D7 VH1 | FIG. 14a |
| 22 | amino acid | hum D7 VH2 | FIG. 14a |
| 23 | amino acid | hum D7 VH3 | FIG. 14a |
| 24 | amino acid | hum D7 VH4 | FIG. 14a |
| 25 | amino acid | hum D7 VH5 | FIG. 14a |
| 26 | amino acid | hum D7 VL1 | FIG. 14b |
| 27 | amino acid | hum D7 VL2 | FIG. 14b |
| 28 | amino acid | hum D7 VL3 | FIG. 14b |
| 29 | amino acid | hum D7 VL4 | FIG. 14b |
| 30 | amino acid | hum D7 VL5 | FIG. 14b |
| 31 | amino acid | D7 VL murine (complete) | FIG. 14b |
| 32 | amino acid | D7 VH murine (CDR only) | FIG. 11 |
| 33 | amino acid | D7 VH hum 1 | FIG. 11 |
| 34 | amino acid | D7 VH hum 2 | FIG. 11 |
| 35 | amino acid | D7 VH hum 3 | FIG. 11 |
| 36 | amino acid | D7 VH hum 4 | FIG. 11 |
| 37 | amino acid | D7 VL murine (CDR only) | FIG. 11 |
| 38 | amino acid | D7 VL hum 1 | FIG. 11 |
| 39 | amino acid | D7 VL hum 2 | FIG. 11 |
| 40 | amino acid | D7 VL hum 3 | FIG. 11 |

-continued

| SEQ ID NO: | nucleic/amino acid | description | |
|---|---|---|---|
| 41 | amino acid | D7 VL hum 4 | FIG. 11 |
| 42 | amino acid | CDR-H1 variant (YFD**M**N) | FIG. 14a |
| 43 | amino acid | CDR-H1 variant (YFD**MH**) | FIG. 14a |
| 44 | amino acid | CDR-H2 variant (GISPGDGNTNYN**Q**NFKG) | FIG. 14a |
| 45 | amino acid | CDR-H2 variant (GISPGDGNTNYN**QK**F**Q**G) | FIG. 14a |
| 46 | amino acid | CDR-H2 variant (**W**ISPGDGNTNY**AQK**F**Q**G) | FIG. 14a |
| 47 | amino acid | CDR-H2 variant (GISPGDGNTNYN**QK**F**Q**G) | FIG. 14a |
| 48 | amino acid | CDR-H2 variant (GISPGDGNTNY**AQK**F**Q**G) | FIG. 14a |
| 49 | amino acid | CDR-H2 variant (GISPGDGNTNY$\mathbf{X_3X_4X_5}$F$\mathbf{X_6}$G) | FIG. 11 |
| 50 | amino acid | CDR-H2 variant (GISPGDGN$\mathbf{X_2}$NY$\mathbf{X_3X_4X_5}$F$\mathbf{X_6}$G) | FIG. 11 |
| 51 | amino acid | CDR-H2 variant (GISPGD$\mathbf{X_1}$N$\mathbf{X_2}$NY$\mathbf{X_3X_4X_5}$F$\mathbf{X_6}$G) | FIG. 11 |
| 52 | amino acid | CDR-L1 variant (RSSQSLVHSNGNTYL**N**) | FIG. 14b |
| 53 | amino acid | CDR-L1 variant (RSSQSLVHSNG$\mathbf{X_8}$TYLH) | FIG. 11 |
| 54 | amino acid | CDR-L1 variant (RSSQSLVHS$\mathbf{X_7}$G$\mathbf{X_8}$TYLH) | FIG. 11 |
| 55 | amino acid | CDR-L2 variant (TVSNRF**D**) | FIG. 14b |
| 56 | amino acid | CDR-L2 variant (TVSNR$\mathbf{X_9}$S) | FIG. 11 |

FIG. 11: Potential mutations in humanized sequences

In FIG. 11 the CDRs are shown. Usually the CDR-H1, CDR-H3 and CDR-L3 are without any amendments. It is possible, however, to replace one amino acid in CDR-L2, up to two amino acids in CDR-L1 and up to six amino acids in CDR-H3. The amino acids which can be replaced are designated as X1-X9 with the meaning shown in the legend to FIG. 11.

FIG. 12: Sequences of construct CAR28

FIGS. 12*a*-12*d* show the sequences of the construct designated as CAR-CD28.

FIG. 13: Sequence of construct CAR41

The sequence of the construct CAR-4-1BB is shown in FIGS. 13*a*-13*d*.

It should be noted that in FIGS. 10-13 the sequence information is provided together with an information which function the relevant parts of the sequences have. Therefore, it is understood that the person skilled in the art derives the information in the best manner from the sequences provided. Sequences 10-13 disclose preferred embodiments of the invention.

FIG. 14: Sequences of humanized ScFv derived from D7

(A) Shown are the murine sequence of the heavy chain of D7 and five humanized variants thereof whereby the locations of CDR-H1, CDR-H2 and CDR-H3 are shown according to the determination of Kabat and according to IMGT as well.

(B) Shown are the murine sequence of the light chain of D7 and of five humanized variants thereof, with CDR-L1, CDR-L2, and CDR-L3. It is understood that the heavy chains and the light chains can be combined with each other. It is for example possible to combine the heavy chain sequence of variant 1 (hum D7-VH1) with the light chain of variant 5 (hum D7-VL5).

Figure 15:
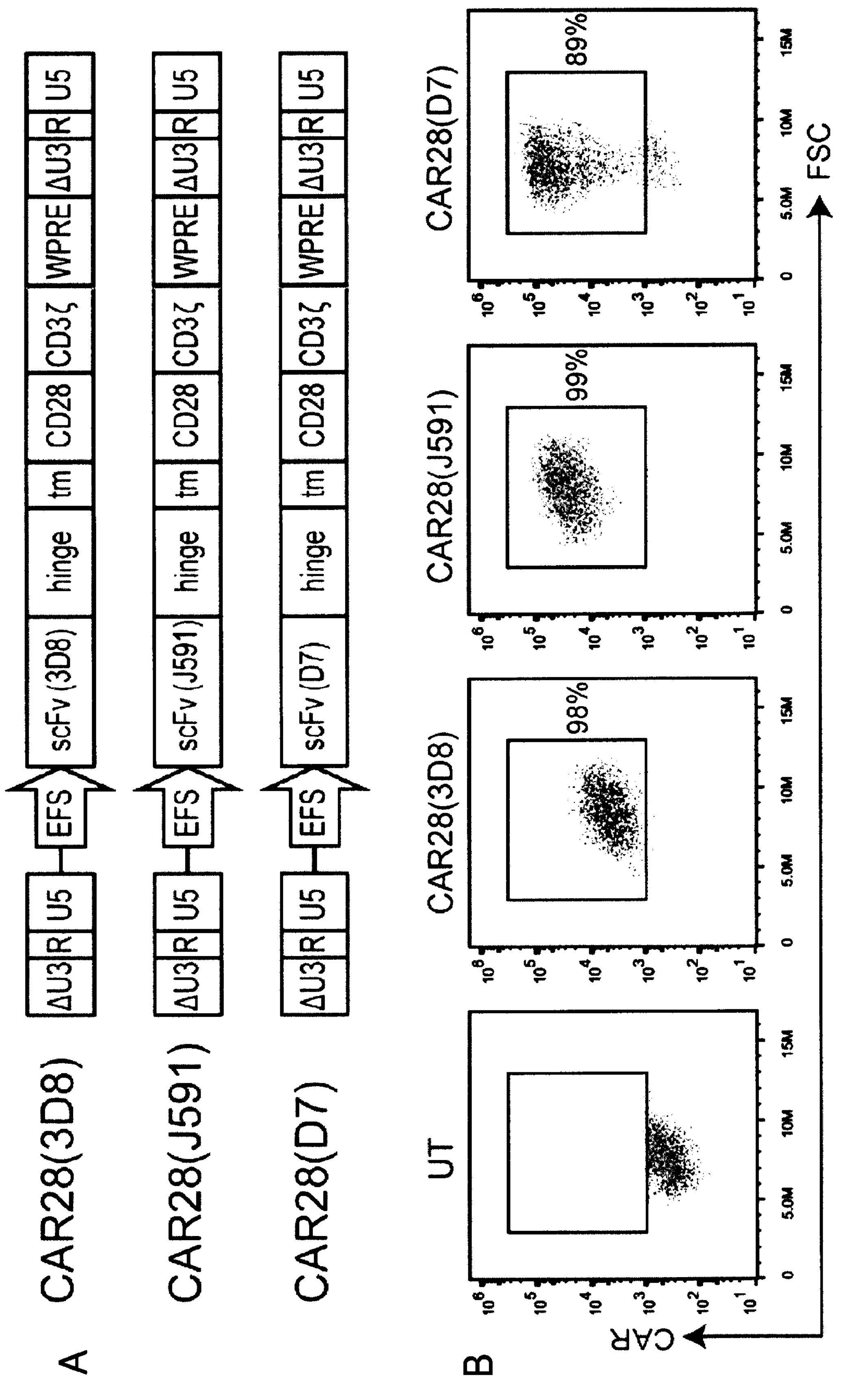
Figure 15:
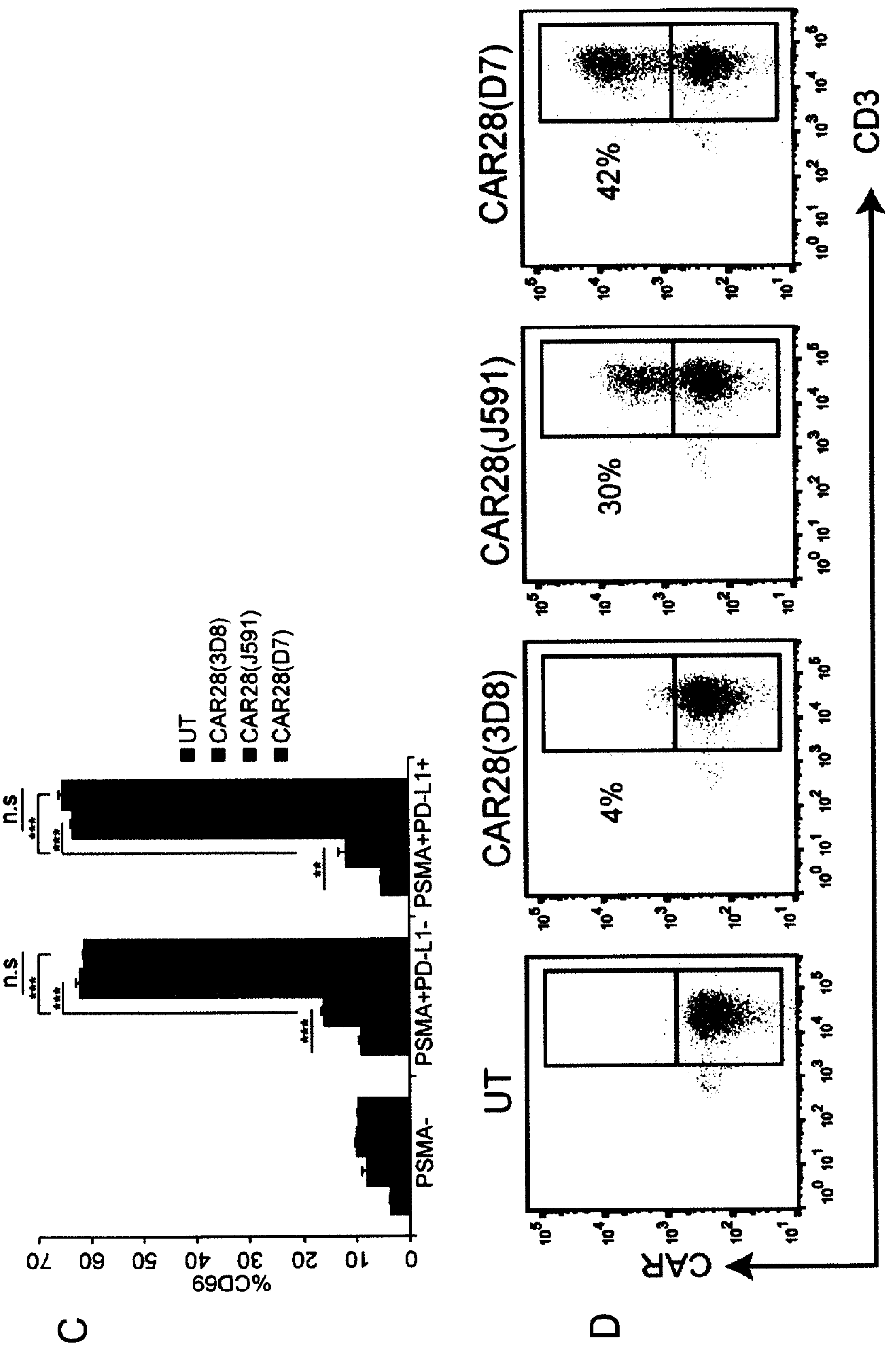
Figure 15:
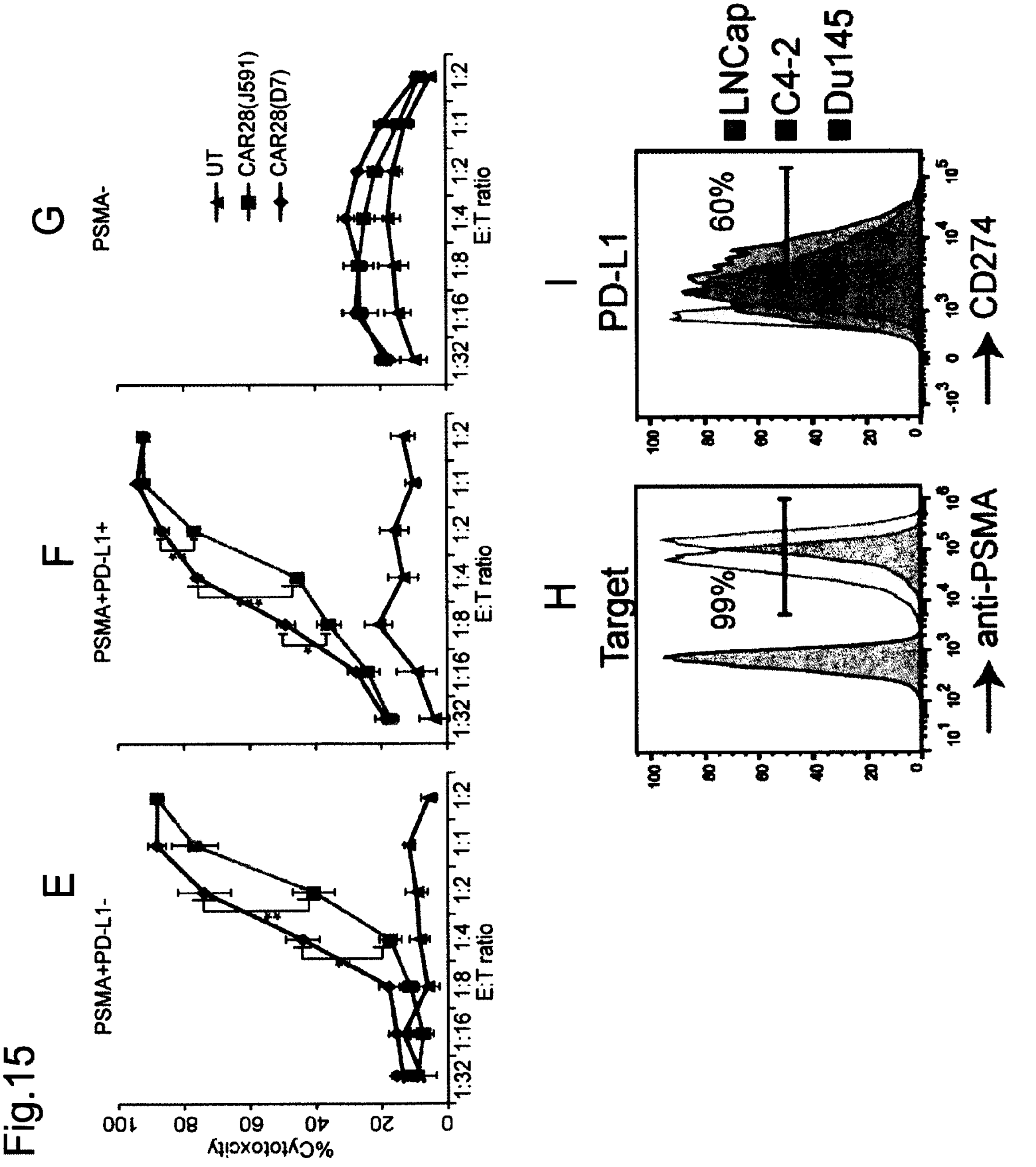

FIG. 15: Comparison of CAR constructs according to the invention with constructs wherein the PSMA antigen binding fragments were already described in the prior art (A) Schematic of the self-inactivating retroviral vector constructs to express $2^{nd}$ generation anti-PSMA CARs. CAR expression is driven by an EFS promoter. The anti-PSMA CARs contain either the single chain variable fragment (scFv) 3D8 or J591 (both described in the prior art), or D7 (derived from 3F/11 murine monoclonal antibody against PSMA), which is fused to an Fc IgG1 derived hinge region, a transmembrane (tm) domain, a CD28 derived costimulatory domain, and an intracellular signaling domain derived from CD3ζ chain. The hinge region provides a physical spacer between the scFv and the tm domains for optimal target recognition. The CD28 co-stimulatory domain contains amino acid exchanges that prevent LCK binding and enhance anti-tumor activity in the presence of inhibitory regulatory T cells (Tregs). All generated retroviral constructs have the same scaffold but differ only in the scFv fragments allowing for a side-by-side comparison of the CAR constructs with respect to activity and cytotoxicity.

(B) CAR expression in Jurkat cells were transduced with retroviral particles coding for the three different PSMA-CARs. Following viral transduction, Jurkat cells were expanded for 16 days before cells were harvested and stained with anti-human IgG antibody (CAR) to evaluate the transduction efficiencies and the CAR expression levels.

(C) Antigen-specific-activation profile, CAR expressing Jurkat cells were stimulated for 24 h at a 1:1 effector-to-target ratio with either PSMA positive, PD-L1 negative C4-2 tumor cells (PSMA+/PDL1−), or PSMA positive, PD-L1 positive LNCaP tumor cells (PSMA+/PDL1+). As a negative control, CAR cells were co-cultured with PSMA negative DU145 tumor cells (PSMA−). Following 24 h stimulation, cells were harvested and activation profile was assessed by evaluating the percentage of cells that are positive for the activation marker CD69.

The antigen-specific activation profiles were compared in D7-based CAR T Jurkat cells side-by-side with J591 and 3D8-based CAR T Jurkat cells. As indicated in Panel C, the D7-based CAR and the J591-based CAR were able to mediate massive activation of the Jurkat cells upon antigen-specific sensitization, as measured by upregulation of the activation marker CD69 in about ~70% of cells. Activation was not affected by the presence of the inhibitory ligand PD-L1. On the other hand, the 3D8-based CAR T cells were only weakly activated (up to 20% of CD69-positive cells).

(D) CAR surface expression in primary T cells. T cells were activated for 2-3 days with anti-CD2/CD3/CD28 antibodies prior to retrovirus transduction. After an expansion for 6-9 days, cells were harvested and stained with anti-human IgG antibody (CAR) and CD3 to evaluate the transduction efficiencies and CAR expression levels.

(E-G) Cytotoxicity profile of CAR T cells were generated by transducing primary T cells after 3 days of activation with anti.-CD3/CD28/CD2 antibodies. After an expansion for 8-9 days, the cytotoxicity profile was examined by co-culturing the CAR T cells for 48 hours at different effector-to-target (E:T) ratios, either C4-2 (PSMA+/PDL1−) tumor cells (E), LNCaP (PSMA+/PDL1+) tumor cells (F) or DU145 (PSMA−) tumor cells (G). Cytotoxicity was measured by an XTT ELISA based colorimetric assay (% cytotoxicity=100%−% viability). Statistically significant differences are indicated by *($P<0.05$), ($P<0.01$), or *($P<0.001$). UT, untransduced cells; PSMA, prostate specific membrane antigen; PD-L1, Programmed cell death ligand 1.

D7-based CAR T cells were compared side-by-side with J591-based CAR T cells. D7-based CAR T cells revealed a superior cytotoxicity profile as compared to J591-based CAR T cells on both tumor cell targets (E, F), as evidenced by the fact both tumor cell lines could be eliminated with lower effector-to-target ratios. Because of the weak activation profile (C) and the lack of efficient expression in T cells (D), 3D8-based CAR T cells were not further included in the comparison. In conclusion, both PSMA antigen-specific activation and cytotoxicity profile of the D7-based CAR T cells outperformed CAR T cells based on prior art CARs.

(H, I) Characterization of employed prostate cancer cell lines. The extent of PSMA target antigen expression (H) and PD-L1 (CD274) expression (I) was assessed on C4-2, LNCaP and DU145 prostate cell lines. For flow cytometric analysis, cells were either stained with 3/F11 antibody (anti-PSMA) or an anti-CD274 antibody. UT, untransduced T cells; PD-L1, Programmed cell death ligand 1; PSMA, prostate specific membrane antigen.

As shown in panel H, both C4-2 and LNCaP tumor cells express the PSMA antigen while the DU145 is negative for the PSMA antigen. Panel I shows that a large fraction of LNCaP and DU145 cells express PD-L1 while C4-2 cells were negative for PD-L1.

Figure 16:
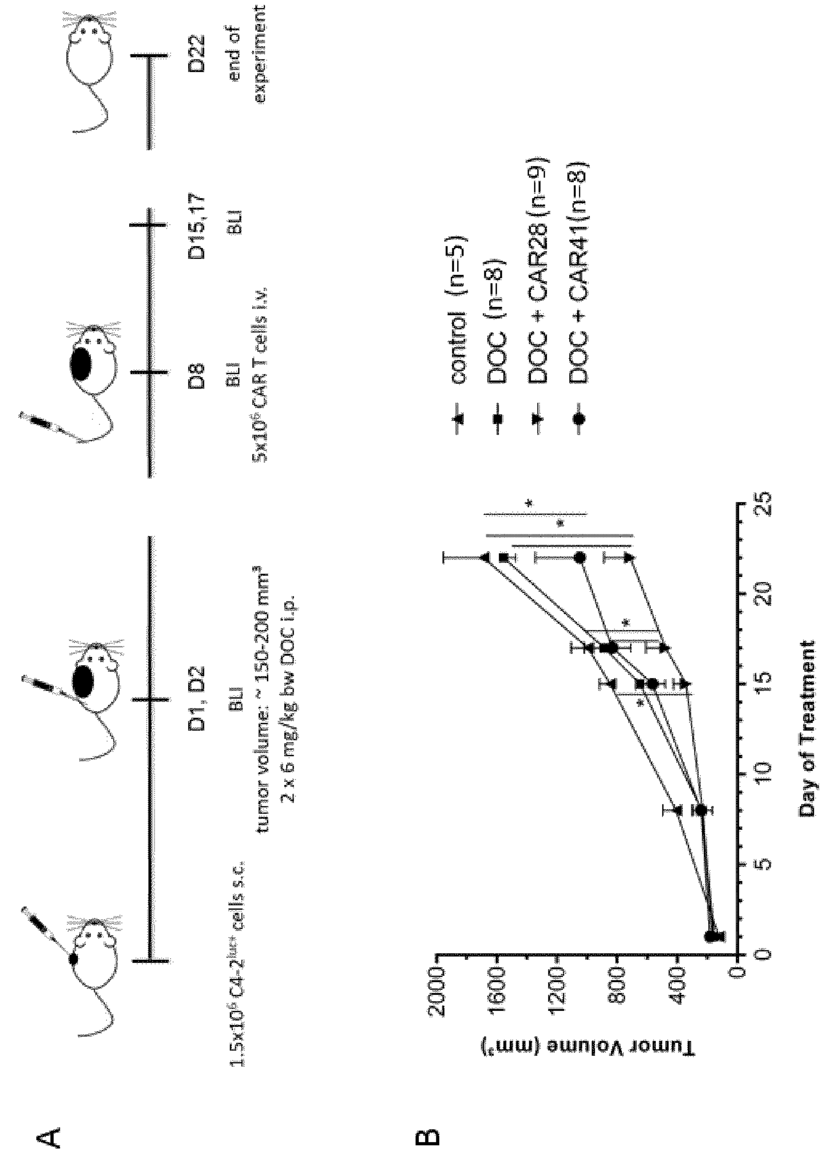

FIG. 16: Combination of chemotherapy together with CAR therapy is superior to chemotherapy alone (A) A schematic of combination therapy of mice being subcutaneous C4-$2^{luc}$ xenografts with docetaxel (DOC) plus CAR T in cells in accordance with the dictates of Example 15, wherein mice with 150-200 $mm^3$ tumors were injected with 2 doses of 6 mg/kg bw DOC on days 1 and 2 followed by i.v. injection of CAR28 or CAR41 T cells on day 8 and tumor hrowth was monitored by palpation and BLI until day 22.

(B) The results of the experiments of Example 15 which depict the synergistic effect of the CAR28 and CAR41 constructs according to the invention together with a chemotherapeutic agent whereby the effect has been exemplified with docetaxel.

DETAILED DESCRIPTION OF THE PREFERRED EMBODIMENTS

Figure 1:
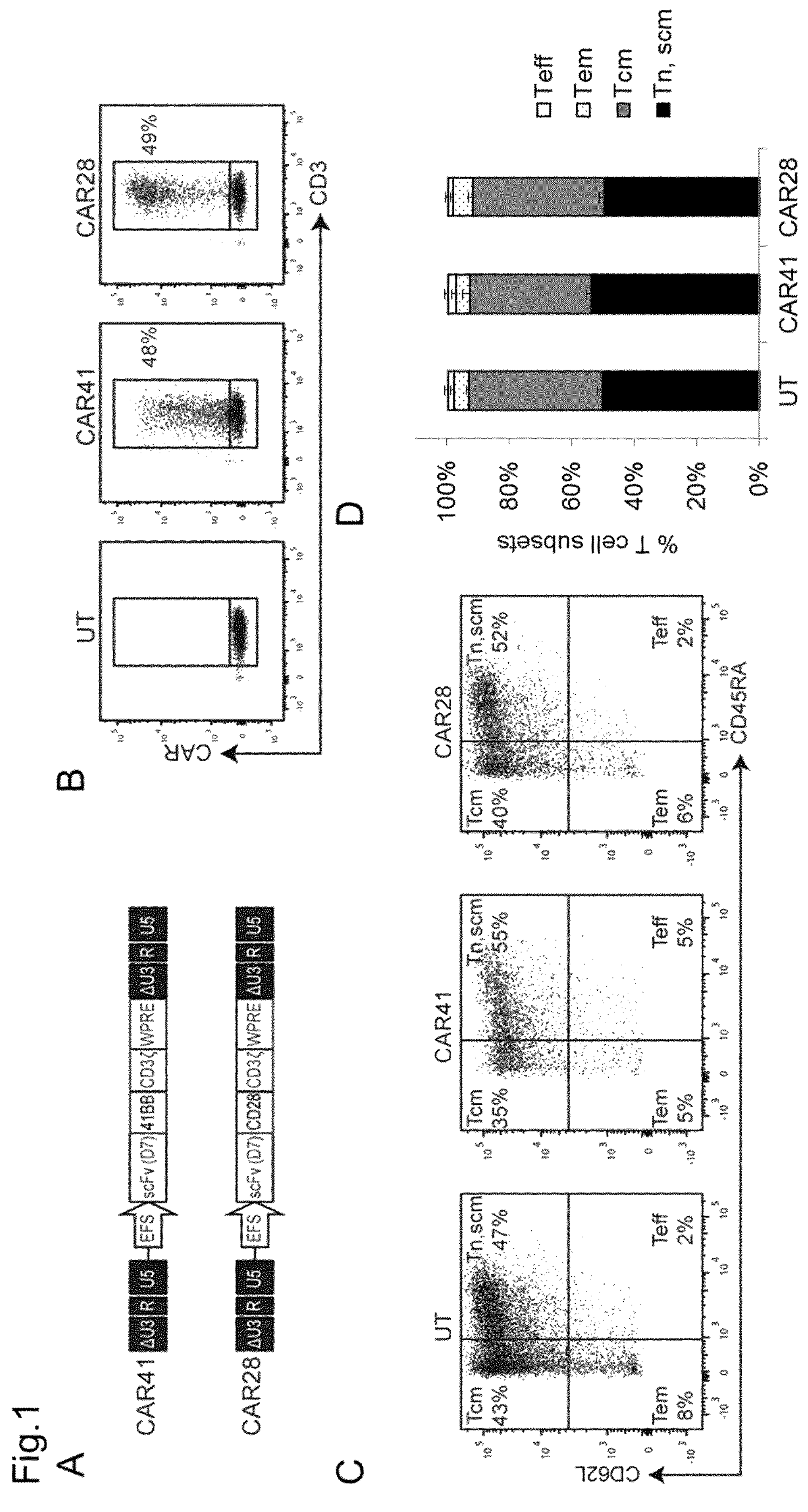
FIG. 1. Generation and quality assessment of PSMA targeting CAR T cells.

The results of the experiments shown in the Figures can be interpreted as follows:

In general, CARs are composed of an extracellular domain containing the antigen recognizing scFv, a hinge region, a transmembrane region, and one or more intracellular signaling domains that activate the T cell, including the CD3ζ chain. In $2^{nd}$ or $3^{rd}$ generation CARs, co-stimulatory domains, usually derived from CD28, 4-1BB, OX40, CD27 and/or ICOS are included (FIG. 1A). For the treatment of prostate cancer, many attempts had utilized CARs targeting PSMA epitopes and some of these strategies have already entered clinical trials (e.g. NCT01140373, NCT01929239). However, the potency of these CARs seems to be rather low both in vitro and in vivo. In particular, early studies based on $1^{st}$ generation CARs based on the anti-PSMA scFv 3D8 or J591 (known as Pzl), have shown low potency of the resulting CAR T cells, as indicated by the need of having to employ high effector to target (E:T) ratios up to 100:1 to eliminate the tumor cells in vitro. The in vitro potency improved when $2^{nd}$ or $3^{rd}$ generation CARs based on either D2B or J591 derived scFvs were used. However, the potency of these CAR T cells remained low in xenotransplantion tumor mouse models, as indicated by the fact that the these PSMA targeting CAR T cells were only able to suppress tumor growth but not to eliminate the tumors in vivo, although very high CAR T cell doses, sometimes up to $20\times10^6$ CAR T cells, or multiple infusions were applied (PMID 16204083, PMID: 18026115, PMID: 19773745, PMID: 25358763, PMID: 23242161, PMID: 4174378, PMID: 25279468). In view of these mixed results with rather inefficient PSMA-CAR T cells, it was intended to generate and validate novel, more efficient PSMA targeting CARs based on the scFv D7. Two different $2^{nd}$ generation PSMA-CARs were designed which either harbor a CD28 (CAR28) or 4-1 BB (CAR41) derived co-stimulatory domain (FIG. 1). The results demonstrate the high effectiveness of these newly developed D7-based PSMA-targeting CAR T cells both in vitro and in vivo. The manufactured CAR T cell products contained a high percentage of undifferentiated T cells, such as a naïve T cell, T stem cell memory and central memory T cell phenotypes (FIG. 1D). These D7-based CAR T cells completely eliminated PSMA-positive tumor cells in vitro at a low effector to target ratio and released the expected cytokines upon specific antigen stimulation (FIG. 2A-C).

CAR41 T cells maintained a more naïve phenotype and less exhaustion profile upon antigen specific stimulation as compared to CAR28 (FIG. 3).

Importantly, the D7-based CAR T cells eliminated solid PSMA-positive tumors in a mouse tumor model upon intratumoral application (FIG. 6). It can be seen that the control (untreated) and the control with untransduced (UT) T cells developed fast growing tumors. The two embodiments of the present invention (CAR28 T cells and CAR41 T cells), however, clearly blocked the tumor growth after an intratumoral single dose application and led to PR or CR. This proves that the concept works in vivo.

An intravenous single-dose injection of the CAR T cells of the present intervention did not cause growth inhibition of PSMA-positive solid tumors (FIG. 8). However, after chemotherapy with docetaxel, a single dose of intravenously injected CAR41 T cells led to a complete remission of large tumors (200-250 $mm^3$) (FIG. 9).

D7-based CAR T cells were compared side-by-side with J591 and 3D8-based CAR T cells (FIG. 15). The antigen-specific activation profiles were compared in Jurkat cells transduced with expression vectors coding for D7, J591 and 3D8-based CARs. While the D7-based CAR and the J591-based CAR were able to mediate massive activation of the Jurkat cells upon antigen-specific sensitization (FIG. 15C), 3D8-CAR bearing cells were only weakly activated. Furthermore, upon transduction of primary T cells, D7-based CAR T cells revealed a superior cytotoxicity profile as compared to J591-based CAR T cells on two PSMA tumor cell lines (FIG. 15E, 15F), as evidenced by the fact that both tumor cell lines were eliminated with lower effector-to-target ratios.

In summary, it has been demonstrated that the D7-based anti-PSMA CAR T cells have unexpected properties that are superior to previously published PSMA-targeting CAR T cells, particularly in view of their superior in vitro cytotoxicity and high in vivo antitumor activity. They are hence promising tools for the development of novel immunotherapies for the treatment of advanced prostate cancer.

The present invention relates therefore to chimeric antigen receptors for T cells which comprise an antigen-binding fragment which binds specifically to the PSMA antigen. The antigen-binding fragment comprises preferably a $V_H$ and a $V_L$ fragment which are connected with a suitable linker. Moreover, the chimeric antigen receptor comprises preferably a spacer element, a transmembrane fragment and a CDR3ζ cytoplasmic domain. Furthermore, the chimeric antigen receptor preferably comprises a fragment from the CD28 (FIG. 12) and/or a 4-1BB (FIG. 13) cytoplasmic domain.

The chimeric antigen receptors of the present invention contain preferably at least three CDRs selected from the group consisting of CDR-H1, CDR-H2, CDR-H3, CDR-L1, CDR-L2 and CDR-L3 as shown in FIG. 10. The CDRs are shown by grey arrows above the amino acid sequence and the relevant nucleic acid sequence coding. In a preferred embodiment the chimeric antigen receptor comprises at least three (CDR-H1, CDR-H3, CDR-L3), preferably four (CDR-H1, CDR-H3, CDR-L2, CDR-L3), and more preferred at least five (CDR-H1, CDR-H3, CDR-L1, CDR-L2, CDR-L3) of the CDRs as shown in FIGS. 10 and 11, respectively.

The chimeric antigen receptors are preferably present in a humanized format. Such a humanized format can be obtained by inserting the at least three, preferably four, more preferred five or six CDRs into a suitable human antigen-binding scaffold having a high homology to the murine scaffold as shown in FIG. 11.

Usually the genetic information coding for the chimeric antigen receptor is introduced with the help of a suitable vector into the target immune cells (e.g. T cell). Such a vector can preferably be a lentivirus vector or a retroviral vector or a transposon or a plasmid. Alternatively, the genetic information can be introduced into the genome of the T cell in a targeted fashion with the help of designer nuclease technology, such as the CRISPR/Cas technology or the TALEN technology, as described herein.

In a further aspect the present invention relates to an in vitro method of providing T cells comprising a chimeric antigen receptor as described herein. In the first step T cells are isolated from a donor preferably by leukapheresis methods. This results in a substantial enrichment of the T cells. The T cells are then genetically modified by transfection with a suitable vector or by transduction with a viral vector containing the genetic information for the chimeric antigen receptor, respectively. Such genetically modified T cells can then be isolated and amplified whereby those T cells which do not contain the desired genetic information can be separated from the modified T cells or at least reduced. The transfected T cells can then be applied to the patient to be treated.

Example 1

Preparation of CAR Encoding Retroviral Particles

HEK293T cells were cultured at 37° C. in a humidified incubator with 5% $CO_2$ in DMEM (Gibco, Invitrogen, Karlsruhe, Germany) supplemented with 10% fetal calf serum (Biochrom, Berlin, Germany), penicillin (100 U/ml), streptomycin (100 mg/L) and 10 mM HEPES (Sigma-Aldrich). One day prior to transfection, cells were seeded in 10 cm dishes at cell density of $5\times10^6$ cells/dish. 24 h later, cells were transfected using polyethylenimine (PEI: 0.1 mg PEI/ml, Polyscience Inc., USA). Per 10 cm dish 3 μg of a plasmid encoding the VSV-G envelope, 6 μg of a gag/pol encoding plasmid, and 10 μg of a vector plasmid coding for either CAR28 or CAR41 were used. 48 and 72 h post-transfection, supernatants containing viral vectors were collected and concentrated using ultracentrifugation (WX ultra series; Thermo Scientific: 25,000 rpm for 2 hours at 4° C.). Concentrated vectors were suspended in 100 μl of cold PBS and kept at −80° C. until used. Biological titers of the vector preparations were determined by transducing the Jurkat T cell line, followed by staining of the transduced cells with anti-human IgG to determine CAR positive cells.

Example 2

Generation of PSMA-Targeting CAR T Cells

CAR T cells were generated from peripheral blood mononuclear cells (PBMCs). PBMCs were isolated using phase separation (Ficoll, Sigma-Aldrich) according to the manufacture's recommendation and then frozen in liquid nitrogen until used. For generation of CAR T cells, PBMCs were thawed and let to recover for 24 h in RPMI complete medium [RPMI 1640 medium (Gibco, Invitrogen, Karlsruhe, Germany) supplemented with 10% fetal calf serum (Biochrom, Berlin, Germany), penicillin (100 U/ml), streptomycin (100 mg/L) and 10 mM HEPES buffer (Sigma-Aldrich)]. Then, PBMCs were activated using anti-CD2/CD3/CD28 antibodies (Immunocult, StemCell Technologies) and cultured with RPMI complete medium supplemented with 100 U/ml of IL-2, 25U/ml of IL-7 and 50 U/ml of IL-15 (all from Miltenyi Biotech) for 2 to 3 days before transduction with gamma-retroviral constructs encoding either CAR28 or CAR41 with MOIs ranging from 50-300. Transduced cells were cultured in wells coated with poly-D-lysin (PDL, Sigma-Aldrich) containing RPMI complete medium supplemented with 5 μg/ml of protamine sulfate (Sigma-Aldrich) and 1000 U/ml of IL-2, 25 U/ml of IL-7 and 50 U/ml of IL-15. After one day, medium was changed and cells were further expanded for 8-9 days in RPMI complete medium supplemented with 100 U/ml of IL-2, 25 U/ml of IL-7 and 50 U/ml of IL-15 before being frozen in liquid nitrogen until further use.

Example 3

Quality Assessment of CAR T Cells

To monitor CAR and TCR expression by flow cytometry (FACS Canto II or Accuri, BD Biosciences), cells were stained with anti-human IgG-PE (Southern Biotech) and CD3-APC (Miltenyi Biotec), respectively. As shown in FIG. 1B, up to 50% transduction efficiency was achieved for both CAR28 or CAR41. For quality assessment, CAR T cells were harvested and stained with anti-human CD62L-Bv421 (BD Biosciences), anti-human CD45RA-FITC (Biolegend), anti-human CD3-APC/H7 (BD Biosciences) and anti-human IgG-PE (CAR) (Southern Biotec) at the end of the expansion period (FIG. 1C, D). The T cell phenotype was determined based on the expression of CD62L and CD45RA. Cells were pre-gated on CD3+/CAR− for untransduced (UT) T cells or on CD3+/CAR+ for both types of CAR T cells (FIGS. 1C, D). Both the transduction and expansion protocol did not induce T cell differentiation, as high percentages of undifferentiated cells with naïve T cell (Tn), T stem cell memory (Tscm) or central memory T cell (Tcm) phenotypes, respectively, in combination with a low fraction of terminally differentiated effector T cells (Teff) were present (FIGS. 1C, D), indicating that the protocol allowed for the generation of high quality CAR T cell products.

Example 4

In Vitro Cytotoxicity of Manufactured CAR T Cells

The cytotoxic potential of the manufactured CAR T cells was determined by assessing cell viability using the XTT assay, as previously described. CAR T cells were co-cultured with either PSMA-positive C4-2 tumor cells or antigen-negative tumor control cells (Du145) in 96 well plates for 48 h at different effector to target ratios in a final volume of 200 μl/well of RPMI complete medium without any cytokines. To determine cell viability as a function of metabolic activity, 100 μl/well of medium was removed and replaced with 100 μl/well of XTT solution (Sigma-Aldrich) and cells incubated at 37° C. Colorimetric changes were quantified using an ELISA reader (Infinite F50, Tecan) at 450 nm. Cytotoxicity is indicated as the percentage of dead cells, which equals 100% minus the percentage of viable cells. Viability was calculated according to the equation $[OD_{E+T}-OD_{E\ only}]/[OD_{T\ only}-OD_{medium\ only}]$(E, effector cells=CAR T cells; T, target cells=tumor cells). As shown in FIG. 2A, CAR28 T cells eliminated ~90% of target cells at an effector to target (E:T) ratio of 1:4, while CAR41 T cells demonstrated comparable activity at an E:T ratio of 1:1. Both types of CAR T cells revealed some minimal alloreactivity when co-cultured with PSMA-negative tumor cells (DU 145) (FIG. 2B). Together, the results demonstrate that both types of D7-based CAR T cells eliminate PSMA-positive target cells with high efficiency and specificity.

Example 5

Cytokine Release by Activated CAR T Cells

CAR T cells were co-cultured with either PSMA-positive C4-2 tumor cells or antigen negative DU 145 tumor cells for 48 h at an effector to target ratio of 1:1 in a final volume of 200 μl/well of RPMI complete medium without any cytokines. To evaluate the cytokines that were released from the CAR T cells during this time, supernatants were collected and evaluated by a multiplexed bead-based immunoassay (cytometric bead array, CBA assay, BD Biosciences) according to the manufacturer's recommendations. Three analytes, interferon gamma (IFN-g), granzyme A (Gr.A) and granzyme B (Gr.B), were determined (FIG. 2C).

Both types of the D7-based CAR T cells secreted the measured pro-inflammatory cytokines upon antigen stimulation, although CAR41 T cells released significantly less cytokines than CAR28 T cells.

Example 6

Cell Differentiation and Exhaustion Upon Antigen Stimulation

CAR T cells were stimulated with PSMA-positive C4-2 tumor cells for 24 h at an effector to target ratio of 1:1, before cells were harvested and stained for T cell phenotype and exhaustion profiles. Assessment of the CAR T cell phenotype upon antigen stimulation revealed that CAR41 cells were less prone to differentiate as compared to CAR28 cells, as indicated by the presence of a significantly higher number of undifferentiated T cell subtypes, such as Tn,scm and Tcm (FIG. 3A, B).

To monitor CAR T cell exhaustion upon specific antigen stimulation, CAR T cells were stimulated with PSMA-positive tumor cells (C4-2) for 24 h, before cells were harvested and stained with anti-human CD279-FITC (PD-1, BD Biosciences), anti-human CD223-eFluor710 (LAG-3, BD Biosciences), anti-human CD3-APC/H7 (BD Biosciences) and anti-human IgG-PE (Southern Biotec). The exhaustion profile was determined by flow cytometry (FACS Canto II) based on the expression of CD279 (PD-1) and CD223 (LAG-3). Cells were pre-gated either on CD3+/CAR− for UT T cells or CD3+/CAR+ for both types of CARs. Yet again, CAR41 cells displayed a different phenotype than CAR28 cells. The significantly reduced number of LAG-3 positive CAR41 T cells is indicative of a less exhausted T cell phenotype (FIG. 3C, D).

Example 7

PSMA Expression of the Prostate Cancer Target Cells $C4\text{-}2^{luc+}$

The PSMA expressing, androgen-independent prostate cancer cell line C4-2 was grown in RPMI 1640 medium (Gibco, Invitrogen, Karlsruhe, Germany) supplemented with penicillin (100 U/ml), streptomycin (100 mg/L) and 10% fetal calf serum (FCS, Biochrom, Berlin, Germany) at 37° C. in a humidified atmosphere of 5% $CO_2$. For in vivo bioluminescence imaging, C4-2 cells were transduced with a lentiviral vector encoding firefly luciferase, a neomycin resistance gene, and green-fluorescent protein (GFP). The cells were named $C4\text{-}2^{luc+}$ cells and selected with 2 mg/ml of the neomycin analog Geneticin (G-418 Sulfate) as previously described. $C4\text{-}2^{luc+}$ cells were tested for PSMA expression by flow cytometry as described previously. In brief, $2\times10^5$ $C4\text{-}2^{luc+}$ cells/well in PBS with 3% FCS and 0.1% $NaN_3$ were incubated with different concentrations of the anti-PSMA mAb 3/F11, the parental mAb of the scFv D7, for 1 h on ice. After washing, cells were incubated with 25 μl goat anti-mouse Ig-RPE (Becton-Dickinson, Mountain View, CA) for 40 min on ice. Cells were then washed repeatedly and suspended in 200 μl PBS containing 1 μg/ml propidium iodide, 3% FCS and 0.1% $NaN_3$. Analysis of stained cells was performed using a FACSCalibur flow cytometer with CellQuest Pro software (BD Biosciences, Heidelberg, Germany).

As shown in FIG. 4A, the mAb 3/F11 bound with a binding constant (kd), defined as the half-maximal saturation concentration, of 0.96 μg/ml (about 6.3 nM) to the C4-$2^{luc+}$ cells. This proved the high expression of PSMA on this cell line. C4-$2^{luc+}$ cells were shown to be PSMA positive at saturation concentrations, while DU 145 prostate cancer control cells were shown to be PSMA negative (FIG. 4B).

Example 8

Bioluminescence of C4-$2^{luc+}$ Cells

Bioluminescence of the C4-$2^{luc+}$ cells was tested with help of the in vivo imaging system IVIS 200 (Xenogen VivoVision). For this, cells were seeded in different numbers into 96-well plates (Nunc Delta Surface, Thermo Fisher Scientific, Roskilde, Denmark) and incubated with 40 μl luciferin/well (BioSynth AG, Staad, Switzerland) as a substrate. Luminescence was analyzed using the software Living Image 3.0 within 10-30 min (Caliper Lifesciences).

Bioluminescence Imaging (BLI) showed that there was linearity between the number of C4-$2^{luc+}$ cells and bioluminescence (quantified as region of interest (ROI). No luminescence signal could be detected with untransduced C4-2 cells and background staining was determined with ROI of max. $2.362\times10^6$ photons/sec/cm$^2$ (FIG. 5).

Example 9

Treatment of C4-$2^{luc+}$ Tumor Xenografts by Intratumoral Injection of CAR T Cells 5-6 week old male SCID CB17/lcr-Prkdc scid/Crl mice (20-25 g, Janvier Labs, St Berthevin Cedex, France) were injected with $1.5\times10^6$ C4-$2^{luc+}$ cells in PBS mixed with 50% Matrigel (Collaborative Biomedical Products, Chicago, IL) s.c. into the right flank. Tumor growth was monitored by BLI. For this, 200 μl of luciferin (BioSynth AG, Staad, Switzerland) were injected i.p. into the animals and BLI was done 10-30 min after injection under anesthesia using the Living imaging system IVIS 200 (Xenogen VivoVision). Tumor volumes were calculated from BLI pictures using the software Living Image 3.0 and the formula Volume=$d^2\times D/2$, where D was the large diameter and d the small diameter of the tumor. When tumors reached volumes of about 60-80 mm$^3$, mice were injected intratumorally with only one dose of $5\times10^6$ CAR28 (n=5) or CAR41 T cells (n=5), respectively (day 1 of treatment) (FIG. 6A). As controls, mice were injected with un-transduced T cells (UT, n=7) or left untreated (control, n=6). Tumor growth was monitored via BLI on days 1, 3, 8, 15, and 22 of treatment. Control groups (UT and untreated) showed a fast tumor growth. A reduced tumor growth was reached with the CAR41 T cells. A marked tumor regression was found in mice treated with CAR28 T cells (FIGS. 6B, C, and D). Until end of treatment at day 22, all animals of the control groups showed growing tumors. According to the animal protection guidelines, one mouse of the untreated group had to be killed due to an ulcerating tumor at day 15.

At day 22, mean tumor end volumes of 1469.4±961.5 mm$^3$ (untreated control) and 1289.1±636.8 mm$^3$ (UT) were reached, respectively. In contrast, 5/5 mice treated with CAR28 T cells showed a complete tumor remission (CR) from day 8 on and 4 mice remained tumor free until the end of the experiment. In the remaining animal a small tumor was detected at day 22 and verified by histological examination with a volume of 0.55 mm$^3$. For all mice treated with CAR28, a mean tumor volume of 0.11±0.22 mm$^3$ was calculated for day 22, which was statistically significant compared to the control groups (*$p<0.05$) (FIGS. 6B and 6D). Mice injected intratumorally with CAR41 T cells showed a different response to the treatment. One of the five animals treated showed a CR (FIGS. 6B and 6D). Another animal showed a PR, whereas the others had tumor progression until day 22 of treatment. In summary, a mean tumor volume in this group of 397.7±393.6 mm$^3$ was determined (FIG. 6C).

Example 10

Adverse Side Effects

According to the animal protection guidelines, mice were observed for apparent signs of toxicity during treatment (loss of weight and appetite, changes in pelage, fever, tension, apathy, aggression, respiratory disorders, paralyses, death) and termination criteria were defined as follows: significantly reduced food intake, decrease of the initial body weight>20%, spasms, paralysis, abnormal breathing disorders, apathy, aggressiveness as a sign of severe pain, tumor diameter>20 mm, ulcerating tumor. With exception of one mouse of the untreated control group, which had to be killed at day 15 because of an ulcerating tumor, no mouse showed apparent signs of toxicity and no animal reached one or more determination criteria. FIG. 7 demonstrates that no animal showed a critical decrease of its initial body weight of >20%. Taken together, all animals have tolerated the intratumoral treatment with the anti-PSMA CAR T cells well without apparent signs of unspecific toxicity.

Example 11

Treatment of C4-$2^{luc+}$ Tumor Xenografts by Intravenous Injection of CAR T Cells Mice with C4-$2^{luc+}$ tumor xenografts were intravenously injected with only one dose of $5\times10^6$ CAR28 (n=5), CAR41 (n=5), or UT T cells (n=5) in 100 μl of PBS, respectively (day 1 of treatment) (FIG. 8A). Control mice (n=6) remained untreated. Tumor growth was monitored as described above. Compared to the control (tumor end volume: 1469.4±961.5 mm$^3$) and the UT group (tumor end volume: 1275.7±544.5 mm$^3$), mice injected with CAR28 T cells showed a similar tumor growth with a mean tumor volume of 1427.3±448.5 mm$^3$ at the end of treatment at day 22 (FIGS. 8B and 8C). For animals treated with the CAR41 T cells a mean tumor volume of 1529.3±971.0 mm$^3$ was determined (FIG. 8C). Tumor growth was not controlled in animals treated either with CAR41 or CAR28 intravenously (FIGS. 8B, C, and D).

In summary, intratumoral application of PSMA CAR T cells, both CAR28 and CAR41, completely eliminated tumors in vivo (FIG. 6). In contrast, intravenous injection of the CAR T cells did not lead to any antitumor activity (FIG. 8), suggesting that the intratumoral injection allowed the CAR T cells to bypass the TME, while upon intravenous injection the CAR T cells were likely inhibited by the TME.

Example 12

Treatment of C4-$2^{luc+}$ Tumor Xenografts by Combination of Chemotherapy and Intravenous Injection of CAR T Cells Mice with large C4-$2^{luc+}$ tumor xenografts (200-250 mm$^3$) were intraperitoneally injected with 3 daily cycles of docetaxel (DOC, 6 mg/kg bw on days 1, 2, and 3 of treatment) (FIG. 9A). 48 hours after the last cycle, mice were intravenously injected with only one dose of $5\times10^6$ CAR28 (n=3) CAR41 T cells (n=3), or PBS (n=3) respectively (FIG. 9A). Control animals (n=4) remained completely untreated. Tumor growth was monitored by BLI as described above. Compared to the control group, mice injected with DOC alone and with DOC+CAR28 showed an inhibition of tumor growth (FIG. 9B). Compared to the control group (1817.5±165.5 $mm^3$) tumor end volumes of 338.2±355.6 $mm^3$ for mice treated with DOC alone and of 599.9±317.2 $mm^3$ for mice treated with DOC+CAR28 were reached on day 17 (FIG. 9C). In contrast, 2/3 animals treated with the DOC+CAR41 combination therapy showed CR and 1/3 mice a PR (FIG. 9B). A mean tumor volume of 50.2±71.0 $mm^3$ was determined (FIG. 9C).

These results indicate that the D7-CAR T cells are effective in eliminating large tumors upon a single dose administration of CAR T cells in combination with chemotherapeutic agents, such as docetaxel (FIG. 9D).

Example 13

Humanization of Murine Sequences

In order to avoid later potential disadvantageous effects like antibodies generated in human patients against the murine part of the antigen binding fragment, the antigen binding fragment derived from the construct D7 was humanized.

In the course of humanizing the sequences the anti-PSMA binding sequence derived from the construct D7 was compared with the sequences of human stem cells. A sequence having a very high homology was selected and the area wherein the CDR binding sequences are located has been determined. For the determination of the CDR sequences several methods are known. The most preferred methods are the method according to Kabat and the IMGT method. IMGT, the International Immunogene Tics database, is a highly qualified integrated information system specializing in immunoglobulin molecules. Since the methods according to Kabat and IMGT provide somewhat different results, the sequences of different variants (hum D7 VH1-5 and hum D7 VL1-5) are shown in FIGS. 14 A and B. The relevant CDR regions according to Kabat and to IMGT are shown.

It is important to note that even by using the two different methods the sequence of CDRH3 having the amino acid sequence ARDGNFPYYAMDS (SEQ ID NO:11) and in CDRL3 having the sequence SQSTHVPT (SEQ ID NO:12) are identical according to both determination methods. It is therefore assumed that those two CDRs, namely CDRH3 and CDRL3 are important for the proper function of the construct. The humanized sequences as shown in FIGS. 14*a* and *b* correspond to SEQ ID NO:13 to 23.

Example 14

The biological activity of a preferred construct according to the present invention has been compared with a construct wherein the PSMA binding fragment is derived from the antibody J591. Furthermore, it was compared with a similar construct wherein the antigen binding construct was derived from another antibody (3D8).

The experiments and the results obtained therefrom are depicted in FIGS. 15A-15I.

FIG. 15A is a schematic representation of different anti-PSMA-CAR28 constructs which are identical except the PSMA binding fragment. In construct CAR28 (D7) the fragment according to the invention was used. In CAR28 (J591) the PSMA fragment was derived from the antibody J591 and in CAR28 (3D8) the PSMA fragment was derived from a PSMA binding antibody (3D8).

The constructs were introduced into Jurkat T-cell lines and the expression of the constructs was measured. In FIG. 15B the control is designated as UT (untransduced). FIG. 15B shows that all CAR constructs measured in flow cytometry are properly expressed in the Jurkat T-cell line except the control, which is designated as UT (untransduced).

In FIG. 15C the antigen-specific activation profile of the transduced JURKAT cells is measured by monitoring the expression of the activation marker upon antigen stimulation. As opposed to D7 and J591 based CARs the 3D8 based CAR mediated only weak activation of the transduced Jurkat cells upon expansion to PSMA expressed tumor cells.

FIG. 15D shows the CAR expression in primary T-cells. It can be seen that the construct according to the invention CAR28 (D7) is better expressed (42%) compared with CAR28 (J591) (30%). The expression of the construct wherein the PSMA binding fragment is derived from 3D8 is very low (4%). A construct which is not expressed to a sufficient extent in primary T-cells is not suitable for later therapeutic use.

The cytotoxicity profiles of the CAR28 T-cells on indicator cells, namely C4-2 (PSMA+/PDL1−); LNCap (PSMA+/PDL1+) and DU145 (PSMA−/PDI1+) is shown in in FIG. 15E-15G. To assess the cytotoxicity profile of the CAR T cells different ratios of effector (CAR28 T-cells): Target cells (different tumor cells, namely C4-2, LNCaP and DU145) have been determined. The construct according to the invention is superior to constructs having the antigen binding fragment derived from the construct J591, as can be seen from FIG. 15E and FIG. 15F. At lower effector:target ratios the construct according to the invention is always superior than the comparative construct. The effector target ratio is a very important aspect for the clinical use since very high effector:target ratios cannot be provided in real life. The lower the effector:target ratio is, the better the construct is.

FIG. 15H and FIG. 15I show the PSMA and PD-L-1 expression on the prostate cancer cell lines LNCaP, C4-2 and DU145.

Example 15

In an additional experiment it could be shown that a combination of chemotherapy together with CAR therapy is superior to chemotherapy alone.

The experiments are shown in FIG. 16A and FIG. 16B. FIG. 16A is a schematic of combination therapy of mice bearing subcutaneous C4-$2^{luc+}$ xenografts with docetaxel (DOC) plus CAR T cells. Mice with 150-200 $mm^3$ tumors were injected with 2 doses of 6 mg/kg bw DOC on days 1 and 2 followed by i.v. injection of CAR28 or CAR41 T cells on day 8. Tumor growth was monitored by palpation and BLI until day 22.

The results of the experiments are shown in FIG. 16B: in vivo antitumor activity of CAR28 and CAR41 T cells in combination with DOC in mice bearing subcutaneous C4-$2^{luc}$ xenografts. Statistically significant differences in tumor volume between DOC+CAR28 treated animals and untreated control were determined on days 15, 17, and 22 of treatment. Statistically significant differences in tumor volume between DOC+CAR28 treated animals and mice, which were only treated with DOC, were determined on days 17 and 22 of treatment. Moreover, tumor volume of animals treated with DOC+CAR41 was significantly smaller than that of the control group on day 22. This proves that combination treatment was superior to chemotherapy alone. Unpaired t-test, *$p<0.05$.

From the experiments it can be clearly seen that there is a synergistic effect of the CAR28 and CAR 41 constructs according to the invention together with a chemotherapeutic agent whereby the effect has been exemplified with docetaxel.

The invention claimed is:

1. A chimeric antigen receptor against a prostate specific membrane antigen (PSMA), said chimeric antigen receptor comprising:

- (a) an antigen-binding fragment which binds specifically to said PSMA, wherein said antigen binding fragment comprises an amino acid sequence that is at least 90% homologous to SEQ ID NO: 1 and includes the following variable regions:
  - (i) a CDR-H1 selected from the group consisting of SEQ ID NO: 2, 42, and 43,
  - (ii) a CDR-H2 selected from the group consisting of SEQ ID NO: 3, 44, 45, 46, 47, 48, 49, 50 and 51,
  - (iii) a CDR-H3 comprising SEQ ID NO: 4,
  - (iv) a CDR-L1 selected from the group consisting of SEQ ID NO: 5, 52, 53, and 54,
  - (v) a CDR-L2 selected from the group consisting of SEQ ID NO: 6, 55, and 56, and
  - (vi) a CDR-L3 comprising SEQ ID NO:7,
- (b) a transmembrane domain, and
- (c) an intracellular signaling domain.

2. The chimeric antigen receptor according to claim 1, characterized in that the antigen-binding fragment is humanized.

3. The chimeric antigen receptor according to claim 2, characterized in that said antigen binding fragment comprises amino acid residues 99 to 112 of SEQ ID NO: 1 (ARDGNFPYYAMDSW).

4. The chimeric antigen receptor according to claim 2, characterized in that said antigen binding fragment comprises the amino acid sequence of SEQ ID NO: 7 (SQSTHVPT).

5. The chimeric antigen receptor according to claim 1, wherein said chimeric antigen receptor further includes (d) a co-stimulatory domain, further wherein said intracellular signaling domain is a CD3ζ cytoplasmic domain and said co-stimulatory domain is a CD28 or 4-1BB cytoplasmic domain or a combination thereof.

6. A nucleic acid coding for the chimeric antigen receptor according to claim 1.

7. A vector coding for the chimeric antigen receptor according to claim 1.

8. The vector according to claim 7, characterized in that said nucleic acid coding for said chimeric antigen receptor comprises SEQ ID NO:10, SEQ ID NO:11, or a sequence that is at least 95% identical to either SEQ ID NO:10 or SEQ ID NO:11.

9. An in vitro method of providing T cells comprising the chimeric antigen receptor according to claim 1, said method comprising the steps of:

- isolating said T cells from a donor by leukapheresis;
- transfecting/transducing said T cells with a vector coding for said chimeric antigen receptor; and
- isolating and amplifying the transfected/transduced T cells.

10. A T cell containing genetic information coding for the chimeric antigen receptor according to claim 1.

11. A method of treating prostate cancer or a prostate-derived tumor, said method comprising the step of administering an effective amount of a composition containing the chimeric antigen receptor according to claim 1 or a nucleic acid or vector encoding same to a patient in need thereof.

12. A method of treating a solid tumor expressing PSMA, said method comprising the step of introducing an agent having anti-tumor activity into said solid tumor, wherein said agent includes the chimeric antigen receptor according to claim 1 or a nucleic acid or vector encoding same.

13. The method according to claim 11, wherein said method further comprises the step of administering a chemotherapeutically active agent to said patient, whereby said chemotherapeutically active agent comprises a cytotoxic substance selected from the group consisting of taxol derivatives, 5-fluorouracil, cyclophosphamide, mitoxanthrione, docetaxel and capacitaxel.

14. The method according to claim 11, wherein said method further comprises the step of administering a biopharmaceutical selected from the group consisting of proteins, antibodies, vaccines, blood, blood components, allergenics, recombinant therapeutic proteins, gene therapies, somatic cells, tissues, cell therapies, enzyme inhibitors, and anti-genomic therapeutics.

15. The method of claim 11, wherein said biopharmaceutical is a protein kinase inhibitor.

16. The chimeric antigen receptor according to claim 1, characterized in that said antigen-binding fragment contains:

a. a variable heavy chain having an amino acid sequence selected from the group consisting of: SEQ ID NO: 21, 22, 23, 24, and 25; and b. a variable light chain having an amino acid sequence selected from the group consisting of: SEQ ID NO: 26, 27, 28, 29, and 30.

17. The chimeric antigen receptor according to claim 1, characterized in that said antigen-binding fragment contains:

a. a variable heavy chain having an amino acid sequence selected from the group consisting of: SEQ ID NO: 33, 34, 35, and 36; and b. a variable light chain having an amino acid sequence selected from the group consisting of: SEQ ID NO: 38, 39, 40, and 41.

18. The chimeric antigen receptor according to claim 16, characterized in that said antigen binding fragment comprises a variable heavy chain comprising the amino acid sequence of SEQ ID NO: 23 and a variable light chain comprising the amino acid sequence of SEQ ID NO: 28.

19. The chimeric antigen receptor according to claim 1, characterized in that said receptor comprises the amino acid sequence of SEQ ID NO: 14 or 17.

* * * * *

SEQUENCE LISTING

```
<160> NUMBER OF SEQ ID NOS: 56

<210> SEQ ID NO 1
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: D 7

<400> SEQUENCE: 1

Met Ala Gln Val Gln Leu Gln Gln Ser Gly Ala Glu Leu Val Glu Pro
1               5                   10                  15

Gly Ala Ser Val Lys Leu Ser Cys Lys Ala Ser Gly Tyr Thr Phe Thr
            20                  25                  30

Tyr Phe Asp Ile Asn Trp Leu Arg Gln Arg Pro Glu Gln Gly Leu Glu
        35                  40                  45

Trp Ile Gly Gly Ile Ser Pro Gly Asp Gly Asn Thr Asn Tyr Asn Glu
    50                  55                  60

Asn Phe Lys Gly Lys Ala Thr Leu Thr Ile Asp Lys Ser Ser Thr Thr
65                  70                  75                  80

Ala Tyr Ile Gln Leu Ser Arg Leu Thr Ser Glu Asp Ser Ala Val Tyr
                85                  90                  95

Phe Cys Ala Arg Asp Gly Asn Phe Pro Tyr Tyr Ala Met Asp Ser Trp
            100                 105                 110

Gly Gln Gly Thr Ser Val Thr Val Ser Ser Ala Lys Thr Thr Pro Lys
        115                 120                 125

Leu Glu Glu Gly Glu Phe Ser Glu Ala Arg Val Asp Ile Glu Leu Thr
    130                 135                 140

Gln Ser Pro Leu Ser Leu Pro Val Ile Leu Gly Asp Gln Ala Ser Ile
145                 150                 155                 160

Ser Cys Arg Ser Ser Gln Ser Leu Val His Ser Asn Gly Asn Thr Tyr
                165                 170                 175

Leu His Trp Phe Leu Gln Lys Pro Gly Gln Ser Pro Lys Leu Leu Ile
            180                 185                 190

Tyr Thr Val Ser Asn Arg Phe Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Leu Gly Val Tyr Phe Cys Ser Gln Ser Thr His Val Pro Thr
225                 230                 235                 240

Phe Gly Gly Gly Thr Lys Leu Glu Ile Lys Arg Ala Asp Ala Ala Ala
                245                 250                 255

Ala Gly Ser


<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-H1

<400> SEQUENCE: 2

Tyr Phe Asp Ile Asn
```

1 5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDR-H2

<400> SEQUENCE: 3

Gly Ile Ser Pro Gly Asp Gly Asn Thr Asn Tyr Asn Glu Asn Phe Lys
1 5 10 15

Gly

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDR - H3

<400> SEQUENCE: 4

Asp Gly Asn Phe Pro Tyr Tyr Ala Met Asp Ser
1 5 10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDR - L1

<400> SEQUENCE: 5

Arg Ser Ser Gln Ser Leu Val His Ser Asn Gly Asn Thr Tyr Leu His
1 5 10 15

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDR - L2

<400> SEQUENCE: 6

Thr Val Ser Asn Arg Phe Ser
1 5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: CDR - L3

<400> SEQUENCE: 7

Ser Gln Ser Thr His Val Pro Thr
1 5

<210> SEQ ID NO 8
<211> LENGTH: 777
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: coding region

<400> SEQUENCE: 8
atggcccagg tgcagctgca gcagtctggg gctgaactgg tagagcctgg ggcttcagtg 60
aaactgtcct gcaaggcttc tggctacacc ttcacatact ttgacataaa ctggttgaga 120
cagaggcctg aacagggact tgagtggatt ggagggattt ctcctggaga tggtaataca 180
aactacaatg agaacttcaa gggcaaggcc acactgacta tagacaaatc ctccaccaca 240
gcctacattc agctcagcag gctgacatct gaggactctg ctgtctattt ctgtgcaaga 300
gatggcaact tcccttacta tgctatggac tcatggggtc aaggaacctc agtcaccgtc 360
tcctcagcca aaacgacacc caagcttgaa gaaggtgaat tttcagaagc acgcgtagac 420
attgagctca cccaatctcc actctccctg cctgtcattc ttggagatca agcctccatc 480
tcttgcagat ctagtcagag ccttgtacac agtaatggaa acacctattt acattggttt 540
ctgcagaagc caggccagtc tccaaagctc ctgatctaca cagtttccaa ccgattttct 600
ggggtcccag acaggttcag tggcagtgga tcagggacag atttcacact caagatcagc 660
agagtggagg ctgaggatct gggagtttat ttctgctctc aaagtaccca tgttcccacg 720
ttcggagggg ggaccaagct ggaaataaaa cgggctgatg ctgcggccgc tggatcc 777

<210> SEQ ID NO 9
<211> LENGTH: 777
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: complementary strand

<400> SEQUENCE: 9
taccgggtcc acgtcgacgt cgtcagaccc cgacttgacc atctcggacc ccgaagtcac 60
tttgacagga cgttccgaag accgatgtgg aagtgtatga aactgtattt gaccaactct 120
gtctccggac ttgtccctga actcacctaa cctccctaaa gaggacctct accattatgt 180
ttgatgttac tcttgaagtt cccgttccgg tgtgactgat atctgtttag gaggtggtgt 240
cggatgtaag tcgagtcgtc cgactgtaga ctcctgagac gacagataaa gacacgttct 300
ctaccgttga agggaatgat acgatacctg agtaccccag ttccttggag tcagtggcag 360
aggagtcggt tttgctgtgg gttcgaactt cttccactta aaagtcttcg tgcgcatctg 420
taactcgagt gggttagagg tgagagggac ggacagtaag aacctctagt tcggaggtag 480
agaacgtcta gatcagtctc ggaacatgtg tcattacctt tgtggataaa tgtaaccaaa 540
gacgtcttcg gtccggtcag aggtttcgag gactagatgt gtcaaaggtt ggctaaaaga 600
ccccagggtc tgtccaagtc accgtcacct agtccctgtc taaagtgtga gttctagtcg 660

```
tctcacctcc gactcctaga ccctcaaata aagacgagag tttcatgggt acaagggtgc    720

aagcctcccc cctggttcga cctttatttt gcccgactac gacgccggcg acctagg       777


<210> SEQ ID NO 10
<211> LENGTH: 2103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: construct CD 28

<400> SEQUENCE: 10

atggattttc aggtgcagat tttcagcttc ctgctaatca gtgcctcagt cataatgtct     60

agaatggccc aggtgcagct tcaacagtct ggcgcggagc tggtcgagcc cggtgctagc    120

gttaagctga gttgtaaggc gtccggctac acatttacct acttcgatat caattggctg    180

agacaaaggc ctgaacaggg cctggaatgg atcggcggaa tctctcccgg agatgggaat    240

acaaattata acgagaactt caagggaaag gctactctta ctatagacaa gtccagcact    300

acggcctaca tccagctgtc ccgcctcacg agcgaggaca gcgccgtgta tttctgtgca    360

agggacggca acttccccta ctatgcaatg gattcttggg ggcagggcac ttccgtcaca    420

gtgagctctg ccaagaccac accgaaactg ggcggaggag gcagtggagg tggggggagc    480

gggggtgggg gaagtgctcg cgtggatatt gagctcactc agagtcctct gtctctccct    540

gtgatactgg gcgaccaagc tagcattagc tgccgaagca gccaatcact ggtccactct    600

aacggaaaca cctatcttca ctggtttctc caaaagcctg gacagtcccc gaagttgctt    660

atttatactg tcagcaaccg attctcaggg gtccccgatc gattcagcgg cagcgggagc    720

gggaccgact ttaccctcaa gatctcccgc gtggaggccg aggacctggg agtctatttc    780

tgcagccagt ctactcatgt gccgacgttc ggaggaggga cgaagttgga gataaaaaga    840

tcggatcccg ccgagcccaa atctcctgac aaaactcaca catgcccacc gtgcccagca    900

cctccagtcg cgggaccgtc agtcttcctc ttccccccaa aacccaagga caccctcatg    960

atcgcccgga cccctgaggt cacatgcgtg gtggtggacg tgagccacga agaccctgag   1020

gtcaagttca actggtacgt ggacggcgtg gaggtgcata atgccaagac aaagccgcgg   1080

gaggagcagt acaacagcac gtaccgtgtg gtcagcgtcc tcaccgtcct gcaccaggac   1140

tggctgaatg gcaaggagta caagtgcaag gtctccaaca aagccctccc agcccccatc   1200

gagaaaacca tctccaaagc caaagggcag ccccgagaac cacaggtgta caccctgccc   1260

ccatcccggg atgagctgac caagaaccag gtcagcctga cctgcctggt caaaggcttc   1320

tatcccagcg acatcgccgt ggagtgggag agcaatgggc agccggagaa caactacaag   1380

accacgcctc ccgtgctgga ctccgacggc tccttcttcc tctacagcaa gctcaccgtg   1440

gacaagagca ggtggcagca ggggaacgtc ttctcatgct ccgtgatgca tgaggctctg   1500

cacaaccact acacgcagaa gagcctctcc ctgtctccgg gtaaaaaaga tcccaaattt   1560

tgggtgctgg tggtggttgg tggagtcctg gcttgctata gcttgctagt aacagtggcc   1620

tttattattt tctgggtgag gagtaagagg agcaggctcc tgcacagtga ctacatgaac   1680

atgactcccc gccgccccgg gcccacccgc aagcattacc aggcctatgc cgccgcacgc   1740

gacttcgcag cctatcgctc cctgagagtg aagttcagca ggagcgcaga cgcccccgcg   1800

taccagcagg gccagaacca gctctataac gagctcaatc taggacgaag agaggagtac   1860
```

gatgttttgg acaagagacg tggccgggac cctgagatgg ggggaaagcc gagaaggaag 1920
aaccctcagg aaggcctgta caatgaactg cagaaagata agatggcgga ggcctacagt 1980
gagattggga tgaaaggcga gcgccggagg ggcaaggggc acgatggcct ttaccagggt 2040
ctcagtacag ccaccaagga cacctacgac gcccttcaca tgcaggccct gccccctcgc 2100
taa 2103

<210> SEQ ID NO 11
<211> LENGTH: 2097
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 4-1 BB

<400> SEQUENCE: 11 atggatttc aggtgcagat tttcagcttc ctgctaatca gtgcctcagt cataatgtct 60
agaatggccc aggtgcagct tcaacagtct ggcgcggagc tggtcgagcc cggtgctagc 120
gttaagctga gttgtaaggc gtccggctac acatttacct acttcgatat caattggctg 180
agacaaaggc ctgaacaggg cctggaatgg atcggcggaa tctctcccgg agatgggaat 240
acaaattata acgagaactt caagggaaag gctactctta ctatagacaa gtccagcact 300
acggcctaca tccagctgtc ccgcctcacg agcgaggaca gcgccgtgta tttctgtgca 360
agggacggca acttccccta ctatgcaatg gattcttggg ggcagggcac ttccgtcaca 420
gtgagctctg ccaagaccac accgaaactg ggcggaggag gcagtggagg tgggggggagc 480 gggggtgggg gaagtgctcg cgtggatatt gagctcactc agagtcctct gtctctccct 540
gtgatactgg gcgaccaagc tagcattagc tgccgaagca gccaatcact ggtccactct 600
aacggaaaca cctatcttca ctggtttctc caaaagcctg gacagtcccc gaagttgctt 660
atttatactg tcagcaaccg attctcaggg gtccccgatc gattcagcgg cagcgggagc 720
gggaccgact ttaccctcaa gatctcccgc gtggaggccg aggacctggg agtctatttc 780
tgcagccagt ctactcatgt gccgacgttc ggaggaggga cgaagttgga gataaaaaga 840
gcggccgctc tacccgccga gcccaaatct cctgacaaaa ctcacacatg cccaccgtgc 900
ccagcacctc cagtcgcggg accgtcagtc ttcctcttcc ccccaaaacc caaggacacc 960
ctcatgatcg cccggacccc tgaggtcaca tgcgtggtgg tggacgtgag ccacgaagac 1020
cctgaggtca agttcaactg gtacgtggac ggcgtggagg tgcataatgc caagacaaag 1080
ccgcgggagg agcagtacaa cagcacgtac cgtgtggtca gcgtcctcac cgtcctgcac 1140
caggactggc tgaatggcaa ggagtacaag tgcaaggtct ccaacaaagc cctcccagcc 1200
cccatcgaga aaaccatctc caaagccaaa gggcagcccc gagaaccaca ggtgtacacc 1260
ctgcccccat cccgggatga gctgaccaag aaccaggtca gcctgacctg cctggtcaaa 1320
ggcttctatc ccagcgacat cgccgtggag tgggagagca atgggcagcc ggagaacaac 1380
tacaagacca cgcctcccgt gctggactcc gacggctcct tcttcctcta cagcaagctc 1440
accgtggaca agagcaggtg gcagcagggg aacgtcttct catgctccgt gatgcatgag 1500
gctctgcaca accactacac gcagaagagc ctctcgagcc tgtctccggg taaaaaaatc 1560
tacatctggg cgcccttggc cgggacttgt ggggtccttc tcctgtcact ggttatcacc 1620
ctttactgca aacggggcag aaagaaactc ctgtatatat tcaaacaacc atttatgaga 1680

```
ccagtacaaa ctactcaaga ggaagatggc tgtagctgcc gatttccaga agaagaagaa   1740

ggaggatgtg aactgctgag agtgaagttc agcaggagcg cagacgcccc cgcgtaccag   1800

cagggccaga accagctcta taacgagctc aatctaggac gaagagagga gtacgatgtt   1860

ttggacaaga gacgtggccg ggaccctgag atggggggaa agccgagaag gaagaaccct   1920

caggaaggcc tgtacaatga actgcagaaa gataagatgg cggaggccta cagtgagatt   1980

gggatgaaag gcgagcgccg gaggggcaag gggcacgatg gcctttacca gggtctcagt   2040

acagccacca aggacaccta cgacgccctt cacatgcagg ccctgccccc tcgctaa      2097
```

<210> SEQ ID NO 12
<211> LENGTH: 779
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: coding strand, optimized for eucariotic expression, Figure 10

<400> SEQUENCE: 12

```
atggcccagg tgcagcttca acagtctggc gcggagctgg tcgagcccgg tgctagcgtt     60

aagctgagtt gtaaggcgtc cggctacaca tttacctact tcgatatcaa ttggctgaga    120

caaaggcctg aacagggcct ggaatggatc ggcggaatct ctcccggaga tgggaataca    180

aattataacg agaacttcaa gggaaaggct actcttacta tagacaagtc cagcactacg    240

gcctacatcc agctgtcccg cctcacgagc gaggacagcg ccgtgtattt ctgtgcaagg    300

gacggcaact tcccctacta tgcaatggat tcttgggggc agggcacttc cgtcacagtg    360

agctctgcca agaccacacc gaaactgggc ggaggaggca gtggaggtgg ggggagcggg    420

ggtgggggaa gtgctcgcgt ggatattgag ctcactcaga gtcctctgtc tctccctgtg    480

atactgggcg accaagctag cattagctgc cgaagcagcc aatcactggt ccactctaac    540

ggaaacacct atcttcactg gtttctccaa aagcctggac agtccccgaa gttgcttatt    600

tcgatactgt gagtaaccga ttctcagggg tccccgatcg attcagcggc agcgggagcg    660

ggaccgactt taccctcaag atctcccgcg tggaggccga ggacctggga gtctatttct    720

gcagccagtc tactcatgtg ccgacgttcg gaggagggac gaagttggag ataaaaaga     779
```

<210> SEQ ID NO 13
<211> LENGTH: 777
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: complementary strand

<400> SEQUENCE: 13

```
taccgggtcc acgtcgaagt tgtcagaccg cgcctcgacc agctcgggcc acgatcgcaa     60

ttcgactcaa cattccgcag gccgatgtgt aaatggatga agctatagtt aaccgactct    120

gtttccggac ttgtcccgga ccttacctag ccgccttaga gagggcctct acccttatgt    180

ttaatattgc tcttgaagtt ccctttccga tgagaatgat atctgttcag gtcgtgatgc    240

cggatgtagg tcgacagggc ggagtgctcg ctcctgtcgc ggcacataaa gacacgttcc    300

ctgccgttga aggggatgat acgttaccta agaacccccg tcccgtgaag gcagtgtcac    360
```

-continued

```
tcgagacggt tctggtgtgg ctttgacccg cctcctccgt cacctccacc cccctcgccc    420

ccaccccctt cacgagcgca cctataactc gagtgagtct caggagacag agagggacac    480

tatgacccgc tggttcgatc gtaatcgacg gcttcgtcgg ttagtgacca ggtgagattg    540

cctttgtgga tagaagtgac caaagaggtt ttcggacctg tcaggggctt caacgaataa    600

atatgacagt cgttggctaa gagtccccag ggctagcta agtcgccgtc gccctcgccc    660

tggctgaaat gggagttcta gagggcgcac ctccggctcc tggaccctca gataaagacg    720

tcggtcagat gagtacacgg ctgcaagcct cctccctgct tcaacctcta tttttct       777
```

```
<210> SEQ ID NO 14
<211> LENGTH: 700
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAR with CD28

<400> SEQUENCE: 14

Met Asp Phe Gln Val Gln Ile Phe Ser Phe Leu Leu Ile Ser Ala Ser
1               5                   10                  15

Val Ile Met Ser Arg Met Ala Gln Val Gln Leu Gln Gln Ser Gly Ala
            20                  25                  30

Glu Leu Val Glu Pro Gly Ala Ser Val Lys Leu Ser Cys Lys Ala Ser
        35                  40                  45

Gly Tyr Thr Phe Thr Tyr Phe Asp Ile Asn Trp Leu Arg Gln Arg Pro
    50                  55                  60

Glu Gln Gly Leu Glu Trp Ile Gly Gly Ile Ser Pro Gly Asp Gly Asn
65                  70                  75                  80

Thr Asn Tyr Asn Glu Asn Phe Lys Gly Lys Ala Thr Leu Thr Ile Asp
                85                  90                  95

Lys Ser Ser Thr Thr Ala Tyr Ile Gln Leu Ser Arg Leu Thr Ser Glu
            100                 105                 110

Asp Ser Ala Val Tyr Phe Cys Ala Arg Asp Gly Asn Phe Pro Tyr Tyr
        115                 120                 125

Ala Met Asp Ser Trp Gly Gln Gly Thr Ser Val Thr Val Ser Ser Ala
    130                 135                 140

Lys Thr Thr Pro Lys Leu Gly Gly Gly Gly Ser Gly Gly Gly Gly Ser
145                 150                 155                 160

Gly Gly Gly Gly Ser Ala Arg Val Asp Ile Glu Leu Thr Gln Ser Pro
                165                 170                 175

Leu Ser Leu Pro Val Ile Leu Gly Asp Gln Ala Ser Ile Ser Cys Arg
            180                 185                 190

Ser Ser Gln Ser Leu Val His Ser Asn Gly Asn Thr Tyr Leu His Trp
        195                 200                 205

Phe Leu Gln Lys Pro Gly Gln Ser Pro Lys Leu Leu Ile Tyr Thr Val
    210                 215                 220

Ser Asn Arg Phe Ser Gly Val Pro Asp Arg Phe Ser Gly Ser Gly Ser
225                 230                 235                 240

Gly Thr Asp Phe Thr Leu Lys Ile Ser Arg Val Glu Ala Glu Asp Leu
                245                 250                 255

Gly Val Tyr Phe Cys Ser Gln Ser Thr His Val Pro Thr Phe Gly Gly
            260                 265                 270

Gly Thr Lys Leu Glu Ile Lys Arg Ser Asp Pro Ala Glu Pro Lys Ser
```

```
        275                 280                 285

Pro Asp Lys Thr His Thr Cys Pro Pro Cys Pro Ala Pro Pro Val Ala
    290                 295                 300

Gly Pro Ser Val Phe Leu Phe Pro Pro Lys Pro Lys Asp Thr Leu Met
305                 310                 315                 320

Ile Ala Arg Thr Pro Glu Val Thr Cys Val Val Val Asp Val Ser His
                325                 330                 335

Glu Asp Pro Glu Val Lys Phe Asn Trp Tyr Val Asp Gly Val Glu Val
            340                 345                 350

His Asn Ala Lys Thr Lys Pro Arg Glu Glu Gln Tyr Asn Ser Thr Tyr
        355                 360                 365

Arg Val Val Ser Val Leu Thr Val Leu His Gln Asp Trp Leu Asn Gly
    370                 375                 380

Lys Glu Tyr Lys Cys Lys Val Ser Asn Lys Ala Leu Pro Ala Pro Ile
385                 390                 395                 400

Glu Lys Thr Ile Ser Lys Ala Lys Gly Gln Pro Arg Glu Pro Gln Val
                405                 410                 415

Tyr Thr Leu Pro Pro Ser Arg Asp Glu Leu Thr Lys Asn Gln Val Ser
            420                 425                 430

Leu Thr Cys Leu Val Lys Gly Phe Tyr Pro Ser Asp Ile Ala Val Glu
        435                 440                 445

Trp Glu Ser Asn Gly Gln Pro Glu Asn Asn Tyr Lys Thr Thr Pro Pro
    450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
            500                 505                 510

Pro Gly Lys Lys Asp Pro Lys Phe Trp Val Leu Val Val Val Gly Gly
        515                 520                 525

Val Leu Ala Cys Tyr Ser Leu Leu Val Thr Val Ala Phe Ile Ile Phe
    530                 535                 540

Trp Val Arg Ser Lys Arg Ser Arg Leu Leu His Ser Asp Tyr Met Asn
545                 550                 555                 560

Met Thr Pro Arg Arg Pro Gly Pro Thr Arg Lys His Tyr Gln Ala Tyr
                565                 570                 575

Ala Ala Ala Arg Asp Phe Ala Ala Tyr Arg Ser Leu Arg Val Lys Phe
            580                 585                 590

Ser Arg Ser Ala Asp Ala Pro Ala Tyr Gln Gln Gly Gln Asn Gln Leu
        595                 600                 605

Tyr Asn Glu Leu Asn Leu Gly Arg Arg Glu Glu Tyr Asp Val Leu Asp
    610                 615                 620

Lys Arg Arg Gly Arg Asp Pro Glu Met Gly Gly Lys Pro Arg Arg Lys
625                 630                 635                 640

Asn Pro Gln Glu Gly Leu Tyr Asn Glu Leu Gln Lys Asp Lys Met Ala
                645                 650                 655

Glu Ala Tyr Ser Glu Ile Gly Met Lys Gly Glu Arg Arg Arg Gly Lys
            660                 665                 670

Gly His Asp Gly Leu Tyr Gln Gly Leu Ser Thr Ala Thr Lys Asp Thr
        675                 680                 685

Tyr Asp Ala Leu His Met Gln Ala Leu Pro Pro Arg
    690                 695                 700
```

<210> SEQ ID NO 15

<400> SEQUENCE: 15

000

<210> SEQ ID NO 16
<211> LENGTH: 2103
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: complementary strand

<400> SEQUENCE: 16
tacctaaaag tccacgtcta aaagtcgaag gacgattagt cacggagtca gtattacaga 60
tcttaccggg tccacgtcga agttgtcaga ccgcgcctcg accagctcgg gccacgatcg 120
caattcgact caacattccg caggccgatg tgtaaatgga tgaagctata gttaaccgac 180
tctgtttccg gacttgtccc ggaccttacc tagccgcctt agagagggcc tctaccctta 240
tgtttaatat tgctcttgaa gttccctttc cgatgagaat gatatctgtt caggtcgtga 300
tgccggatgt aggtcgacag ggcggagtgc tcgctcctgt cgcggcacat aaagacacgt 360
tccctgccgt tgaaggggat gatacgttac ctaagaaccc ccgtcccgtg aaggcagtgt 420
cactcgagac ggttctggtg tggctttgac ccgcctcctc cgtcacctcc acccccctcg 480
cccccacccc cttcacgagc gcacctataa ctcgagtgag tctcaggaga cagagaggga 540
cactatgacc cgctggttcg atcgtaatcg acggcttcgt cggttagtga ccaggtgaga 600
ttgcctttgt ggatagaagt gaccaaagag gttttcggac ctgtcagggg cttcaacgaa 660
taaatatgac agtcgttggc taagagtccc caggggctag ctaagtcgcc gtcgccctcg 720
ccctggctga aatgggagtt ctagagggcg cacctccggc tcctggaccc tcagataaag 780
acgtcggtca gatgagtaca cggctgcaag cctcctccct gcttcaacct ctatttttct 840
agcctagggc ggctcgggtt tagaggactg ttttgagtgt gtacgggtgg cacgggtcgt 900
ggaggtcagc gccctggcag tcagaaggag aagggggggtt ttgggttcct gtgggagtac 960
tagcgggcct ggggactcca gtgtacgcac caccacctgc actcggtgct tctgggactc 1020
cagttcaagt tgaccatgca cctgccgcac ctccacgtat tacggttctg tttcggcgcc 1080
ctcctcgtca tgttgtcgtg catggcacac cagtcgcagg agtggcagga cgtggtcctg 1140
accgacttac cgttcctcat gttcacgttc cagaggttgt ttcgggaggg tcgggggtag 1200
ctcttttggt agaggtttcg gtttcccgtc ggggctcttg gtgtccacat gtgggacggg 1260
ggtagggccc tactcgactg gttcttggtc cagtcggact ggacggacca gtttccgaag 1320
atagggtcgc tgtagcggca cctcaccctc tcgttacccg tcggcctctt gttgatgttc 1380
tggtgcggag ggcacgacct gaggctgccg aggaagaagg agatgtcgtt cgagtggcac 1440
ctgttctcgt ccaccgtcgt ccccttgcag aagagtacga ggcactacgt actccgagac 1500
gtgttggtga tgtgcgtctt ctcggagagg gacagaggcc catttttttct agggtttaaa 1560 acccacgacc accaccaacc acctcaggac cgaacgatat cgaacgatca ttgtcaccgg 1620
aaataataaa agacccactc ctcattctcc tcgtccgagg acgtgtcact gatgtacttg 1680
tactgagggg cggcggggcc cgggtgggcg ttcgtaatgg tccggatacg gcggcgtgcg 1740

-continued

```
ctgaagcgtc ggatagcgag ggactctcac ttcaagtcgt cctcgcgtct gcgggggcgc   1800

atggtcgtcc cggtcttggt cgagatattg ctcgagttag atcctgcttc tctcctcatg   1860

ctacaaaacc tgttctctgc accggccctg ggactctacc cccctttcgg ctcttccttc   1920

ttgggagtcc ttccggacat gttacttgac gtctttctat tctaccgcct ccggatgtca   1980

ctctaaccct actttccgct cgcggcctcc ccgttccccg tgctaccgga aatggtccca   2040

gagtcatgtc ggtggttcct gtggatgctg cgggaagtgt acgtccggga cgggggagcg   2100

att                                                                 2103
```

```
<210> SEQ ID NO 17
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAR with 4-1 BB

<400> SEQUENCE: 17

Met Asp Phe Gln Val Gln Ile Phe Ser Phe Leu Leu Ile Ser Ala Ser
1               5                   10                  15

Val Ile Met Ser Arg Met Ala Gln Val Gln Leu Gln Gln Ser Gly Ala
            20                  25                  30

Glu Leu Val Glu Pro Gly Ala Ser Val Lys Leu Ser Cys Lys Ala Ser
        35                  40                  45

Gly Tyr Thr Phe Thr Tyr Phe Asp Ile Asn Trp Leu Arg Gln Arg Pro
    50                  55                  60

Glu Gln Gly Leu Glu Trp Ile Gly Gly Ile Ser Pro Gly Asp Gly Asn
65                  70                  75                  80

Thr Asn Tyr Asn Glu Asn Phe Lys Gly Lys Ala Thr Leu Thr Ile Asp
                85                  90                  95

Lys Ser Ser Thr Thr Ala Tyr Ile Gln Leu Ser Arg Leu Thr Ser Glu
            100                 105                 110

Asp Ser Ala Val Tyr Phe Cys Ala Arg Asp Gly Asn Phe Pro Tyr Tyr
        115                 120                 125

Ala Met Asp Ser Trp Gly Gln Gly Thr Ser Val Thr Val Ser Ser Ala
    130                 135                 140

Lys Thr Thr Pro Lys Leu Gly Gly Gly Gly Ser Gly Gly Gly Gly Ser
145                 150                 155                 160

Gly Gly Gly Gly Ser Ala Arg Val Asp Ile Glu Leu Thr Gln Ser Pro
                165                 170                 175

Leu Ser Leu Pro Val Ile Leu Gly Asp Gln Ala Ser Ile Ser Cys Arg
            180                 185                 190

Ser Ser Gln Ser Leu Val His Ser Asn Gly Asn Thr Tyr Leu His Trp
        195                 200                 205

Phe Leu Gln Lys Pro Gly Gln Ser Pro Lys Leu Leu Ile Tyr Thr Val
    210                 215                 220

Ser Asn Arg Phe Ser Gly Val Pro Asp Arg Phe Ser Gly Ser Gly Ser
225                 230                 235                 240

Gly Thr Asp Phe Thr Leu Lys Ile Ser Arg Val Glu Ala Glu Asp Leu
                245                 250                 255

Gly Val Tyr Phe Cys Ser Gln Ser Thr His Val Pro Thr Phe Gly Gly
            260                 265                 270

Gly Thr Lys Leu Glu Ile Lys Arg Ala Ala Ala Leu Pro Ala Glu Pro
```

-continued

```
        275                 280                 285

Lys Ser Pro Asp Lys Thr His Thr Cys Pro Pro Cys Pro Ala Pro Pro
    290                 295                 300

Val Ala Gly Pro Ser Val Phe Leu Phe Pro Pro Lys Pro Lys Asp Thr
305                 310                 315                 320

Leu Met Ile Ala Arg Thr Pro Glu Val Thr Cys Val Val Val Asp Val
                325                 330                 335

Ser His Glu Asp Pro Glu Val Lys Phe Asn Trp Tyr Val Asp Gly Val
            340                 345                 350

Glu Val His Asn Ala Lys Thr Lys Pro Arg Glu Glu Gln Tyr Asn Ser
        355                 360                 365

Thr Tyr Arg Val Val Ser Val Leu Thr Val Leu His Gln Asp Trp Leu
    370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
                405                 410                 415

Gln Val Tyr Thr Leu Pro Pro Ser Arg Asp Glu Leu Thr Lys Asn Gln
            420                 425                 430

Val Ser Leu Thr Cys Leu Val Lys Gly Phe Tyr Pro Ser Asp Ile Ala
        435                 440                 445

Val Glu Trp Glu Ser Asn Gly Gln Pro Glu Asn Asn Tyr Lys Thr Thr
    450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
                485                 490                 495

Val Met His Glu Ala Leu His Asn His Tyr Thr Gln Lys Ser Leu Ser
            500                 505                 510

Ser Leu Ser Pro Gly Lys Lys Ile Tyr Ile Trp Ala Pro Leu Ala Gly
        515                 520                 525

Thr Cys Gly Val Leu Leu Leu Ser Leu Val Ile Thr Leu Tyr Cys Lys
    530                 535                 540

Arg Gly Arg Lys Lys Leu Leu Tyr Ile Phe Lys Gln Pro Phe Met Arg
545                 550                 555                 560

Pro Val Gln Thr Thr Gln Glu Glu Asp Gly Cys Ser Cys Arg Phe Pro
                565                 570                 575

Glu Glu Glu Glu Gly Gly Cys Glu Leu Leu Arg Val Lys Phe Ser Arg
            580                 585                 590

Ser Ala Asp Ala Pro Ala Tyr Gln Gln Gly Gln Asn Gln Leu Tyr Asn
        595                 600                 605

Glu Leu Asn Leu Gly Arg Arg Glu Glu Tyr Asp Val Leu Asp Lys Arg
    610                 615                 620

Arg Gly Arg Asp Pro Glu Met Gly Gly Lys Pro Arg Arg Lys Asn Pro
625                 630                 635                 640

Gln Glu Gly Leu Tyr Asn Glu Leu Gln Lys Asp Lys Met Ala Glu Ala
                645                 650                 655

Tyr Ser Glu Ile Gly Met Lys Gly Glu Arg Arg Arg Gly Lys Gly His
            660                 665                 670

Asp Gly Leu Tyr Gln Gly Leu Ser Thr Ala Thr Lys Asp Thr Tyr Asp
        675                 680                 685

Ala Leu His Met Gln Ala Leu Pro Pro Arg
    690                 695
```

<210> SEQ ID NO 18

<400> SEQUENCE: 18

000

<210> SEQ ID NO 19
<211> LENGTH: 2097
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: complementary strand

<400> SEQUENCE: 19
tacctaaaag tccacgtcta aaagtcgaag gacgattagt cacggagtca gtattacaga 60
tcttaccggg tccacgtcga agttgtcaga ccgcgcctcg accagctcgg gccacgatcg 120
caattcgact caacattccg caggccgatg tgtaaatgga tgaagctata gttaaccgac 180
tctgtttccg gacttgtccc ggaccttacc tagccgcctt agagagggcc tctaccctta 240
tgtttaatat tgctcttgaa gttccctttc cgatgagaat gatatctgtt caggtcgtga 300
tgccggatgt aggtcgacag ggcggagtgc tcgctcctgt cgcggcacat aaagacacgt 360
tccctgccgt tgaaggggat gatacgttac ctaagaaccc ccgtcccgtg aaggcagtgt 420
cactcgagac ggttctggtg tggctttgac ccgcctcctc cgtcacctcc accccccctcg 480 cccccacccc cttcacgagc gcacctataa ctcgagtgag tctcaggaga cagagaggga 540
cactatgacc cgctggttcg atcgtaatcg acggcttcgt cggttagtga ccaggtgaga 600
ttgcctttgt ggatagaagt gaccaaagag gttttcggac ctgtcagggg cttcaacgaa 660
taaatatgac agtcgttggc taagagtccc caggggctag ctaagtcgcc gtcgccctcg 720
ccctggctga aatgggagtt ctagagggcg cacctccggc tcctggaccc tcagataaag 780
acgtcggtca gatgagtaca cggctgcaag cctcctccct gcttcaacct ctatttttct 840
cgccggcgag atgggcggct cgggtttaga ggactgtttt gagtgtgtac gggtggcacg 900
ggtcgtggag gtcagcgccc tggcagtcag aaggagaagg ggggttttgg gttcctgtgg 960
gagtactagc gggcctgggg actccagtgt acgcaccacc acctgcactc ggtgcttctg 1020
ggactccagt tcaagttgac catgcacctg ccgcacctcc acgtattacg gttctgtttc 1080
ggcgccctcc tcgtcatgtt gtcgtgcatg gcacaccagt cgcaggagtg gcaggacgtg 1140
gtcctgaccg acttaccgtt cctcatgttc acgttccaga ggttgtttcg ggagggtcgg 1200
gggtagctct tttggtagag gtttcggttt cccgtcgggg ctcttggtgt ccacatgtgg 1260
gacgggggta gggccctact cgactggttc ttggtccagt cggactggac ggaccagttt 1320
ccgaagatag ggtcgctgta gcggcacctc accctctcgt tacccgtcgg cctcttgttg 1380
atgttctggt gcggagggca cgacctgagg ctgccgagga agaaggagat gtcgttcgag 1440
tggcacctgt tctcgtccac cgtcgtcccc ttgcagaaga gtacgaggca ctacgtactc 1500
cgagacgtgt tggtgatgtg cgtcttctcg gagagctcgg acagaggccc attttttttag 1560 atgtagaccc gcgggaaccg gccctgaaca ccccaggaag aggacagtga ccaatagtgg 1620
gaaatgacgt ttgccccgtc tttctttgag gacatatata agtttgttgg taaatactct 1680
ggtcatgttt gatgagttct ccttctaccg acatcgacgg ctaaaggtct tcttcttctt 1740
cctcctacac ttgacgactc tcacttcaag tcgtcctcgc gtctgcgggg gcgcatggtc 1800
gtcccggtct tggtcgagat attgctcgag ttagatcctg cttctctcct catgctacaa 1860
aacctgttct ctgcaccggc cctgggactc taccccccctt tcggctcttc cttcttggga 1920
gtccttccgg acatgttact tgacgtcttt ctattctacc gcctccggat gtcactctaa 1980
ccctactttc cgctcgcggc ctccccgttc cccgtgctac cggaaatggt cccagagtca 2040
tgtcggtggt tcctgtggat gctgcgggaa gtgtacgtcc gggacggggg agcgatt 2097

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: D7 VH murine

<400> SEQUENCE: 20

Gln Val Gln Leu Gln Gln Ser Gly Ala Glu Leu Val Glu Pro Gly Ala
1 5 10 15

Ser Val Lys Leu Ser Cys Lys Ala Ser Gly Tyr Thr Phe Thr Tyr Phe
20 25 30

Asp Ile Asn Trp Leu Arg Gln Arg Pro Glu Gln Gly Leu Glu Trp Ile
35 40 45

Gly Gly Ile Ser Pro Gly Asp Gly Asn Thr Asn Tyr Asn Glu Asn Phe
50 55 60

Lys Gly Lys Ala Thr Leu Thr Ile Asp Lys Ser Ser Thr Thr Ala Tyr
65 70 75 80

Ile Gln Leu Ser Arg Leu Thr Ser Glu Asp Ser Ala Val Tyr Phe Cys
85 90 95

Ala Arg Asp Gly Asn Phe Pro Tyr Tyr Ala Met Asp Ser Trp Gly Gln
100 105 110

Gly Thr Ser Val Thr Val Ser Ser
115 120

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: hum D7 VH 1

<400> SEQUENCE: 21

Gln Val Gln Leu Gln Gln Ser Gly Ala Glu Val Val Glu Pro Gly Ala
1 5 10 15

Ser Val Lys Leu Ser Cys Lys Ala Ser Gly Tyr Thr Phe Thr Tyr Phe
20 25 30

Asp Met Asn Trp Val Arg Gln Arg Pro Glu Gln Gly Leu Glu Trp Met
35 40 45

Gly Gly Ile Ser Pro Gly Asp Gly Asn Thr Asn Tyr Asn Gln Asn Phe
50 55 60

Lys Gly Arg Val Thr Met Thr Ile Asp Lys Ser Ser Ser Thr Ala Tyr
65 70 75 80

Met Glu Leu Ser Arg Leu Thr Ser Asp Asp Thr Ala Val Tyr Phe Cys
85 90 95

```
Ala Arg Asp Gly Asn Phe Pro Tyr Tyr Ala Met Asp Ser Trp Gly Gln
            100                 105                 110

Gly Thr Ser Val Thr Val Ser Ser
        115                 120


<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hum D7 VH2

<400> SEQUENCE: 22

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Tyr Phe
            20                  25                  30

Asp Met Asn Trp Val Arg Gln Arg Pro Glu Gln Gly Leu Glu Trp Met
        35                  40                  45

Gly Gly Ile Ser Pro Gly Asp Gly Asn Thr Asn Tyr Asn Gln Lys Phe
    50                  55                  60

Gln Gly Arg Val Thr Met Thr Arg Asp Lys Ser Ser Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Ser Val Thr Val Ser Ser
        115                 120


<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hum D7 VH3

<400> SEQUENCE: 23

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Tyr Phe
            20                  25                  30

Asp Met His Trp Val Arg Gln Ala Pro Gly Gln Gly Leu Glu Trp Met
        35                  40                  45

Gly Trp Ile Ser Pro Gly Asp Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Ser Val Thr Val Ser Ser
```

115 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: hum d7 VH4

<400> SEQUENCE: 24

Gln Val Gln Leu Val Gln Ser Gly Ala Glu Val Val Lys Pro Gly Ala
1 5 10 15

Ser Val Lys Leu Ser Cys Lys Ala Ser Gly Tyr Thr Phe Thr Tyr Phe
20 25 30

Asp Ile Asn Trp Leu Arg Gln Arg Pro Gly Gln Gly Leu Glu Trp Ile
35 40 45

Gly Gly Ile Ser Pro Gly Asp Gly Asn Thr Asn Tyr Asn Gln Lys Phe
50 55 60

Gln Gly Arg Ala Thr Leu Thr Ile Asp Thr Ser Ser Ser Thr Ala Tyr
65 70 75 80

Ile Glu Leu Ser Arg Leu Arg Ser Asp Asp Thr Ala Val Tyr Phe Cys
85 90 95

Ala Arg Asp Gly Asn Phe Pro Tyr Tyr Ala Met Asp Ser Trp Gly Gln
100 105 110

Gly Thr Leu Val Thr Val Ser Ser
115 120

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: hum D7 VH5

<400> SEQUENCE: 25

Gln Val Gln Leu Val Gln Ser Gly Ala Glu Val Val Lys Pro Gly Ala
1 5 10 15

Ser Val Lys Val Ser Cys Lys Ala Ser Gly Tyr Thr Phe Thr Tyr Phe
20 25 30

Asp Met Asn Trp Leu Arg Gln Ala Pro Gly Gln Gly Leu Glu Trp Met
35 40 45

Gly Gly Ile Ser Pro Gly Asp Gly Asn Thr Asn Tyr Ala Gln Lys Phe
50 55 60

Gln Gly Arg Val Thr Met Thr Ile Asp Thr Ser Ser Ser Thr Ala Tyr
65 70 75 80

Met Glu Leu Ser Arg Leu Arg Ser Asp Asp Thr Ala Val Tyr Tyr Cys
85 90 95

Ala Arg Asp Gly Asn Phe Pro Tyr Tyr Ala Met Asp Ser Trp Gly Gln
100 105 110

Gly Thr Leu Val Thr Val Ser Ser
115 120

<210> SEQ ID NO 26
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: humD7 VL1

<400> SEQUENCE: 26

Asp Val Glu Met Thr Gln Ser Pro Leu Ser Leu Pro Val Ile Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Phe Leu Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Thr Phe Gly Gly Gly Thr Lys Leu Glu Ile Lys
            100                 105                 110


<210> SEQ ID NO 27
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hum D7 VL2

<400> SEQUENCE: 27

Asp Val Val Met Thr Gln Ser Pro Leu Ser Leu Pro Val Ile Leu Gly
1               5                   10                  15

Gln Gln Ala Ser Ile Ser Cys Arg Ser Ser Gln Ser Leu Val His Ser
            20                  25                  30

Asn Gly Asn Thr Tyr Leu His Trp Phe Leu Gln Arg Pro Gly Gln Ser
        35                  40                  45

Pro Arg Arg Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Thr Phe Gly Gly Gly Thr Lys Leu Glu Ile Lys
            100                 105                 110


<210> SEQ ID NO 28
<211> LENGTH: 111
<212> TYPE: PRT
<213> ORGANISM: Human mastadenovirus C

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30
```

Asn Gly Asn Thr Tyr Leu Asn Trp Phe Gln Gln Arg Pro Gly Gln Ser
35 40 45

Pro Arg Arg Leu Ile Tyr Thr Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Thr Phe Gly Gly Gly Thr Lys Leu Glu Ile Lys
100 105 110

<210> SEQ ID NO 29
<211> LENGTH: 111
<212> TYPE: PRT
<213> ORGANISM: Human mastadenovirus C

<400> SEQUENCE: 29

Asp Ile Val Leu Thr Gln Ser Pro Leu Ser Leu Pro Val Thr Leu Gly
1 5 10 15

Gln Gln Ala Ser Ile Ser Cys Arg Ser Ser Gln Ser Leu Val His Ser
20 25 30

Asn Gly Asn Thr Tyr Leu His Trp Phe Leu Gln Arg Pro Gly Gln Ser
35 40 45

Pro Arg Leu Leu Ile Tyr Thr Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Phe Cys Ser Gln Ser
85 90 95

Thr His Val Pro Thr Phe Gly Gly Gly Thr Lys Leu Glu Ile Lys
100 105 110

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: hum D7 VL5

<400> SEQUENCE: 30

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val His Ser
20 25 30

Asn Gly Asn Thr Tyr Leu His Trp Phe Gln Gln Arg Pro Gly Gln Ser
35 40 45

Pro Arg Leu Leu Ile Tyr Thr Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Thr Phe Gly Gly Gly Thr Lys Val Glu Ile Lys
100 105 110

<210> SEQ ID NO 31
<211> LENGTH: 111
<212> TYPE: PRT
<213> ORGANISM: Mus sp.
<220> FEATURE:
<223> OTHER INFORMATION: murine D7 VL

<400> SEQUENCE: 31

```
Asp Ile Glu Leu Thr Gln Ser Pro Leu Ser Leu Pro Val Ile Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Phe Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Gly Gly Thr Lys Leu Glu Ile Lys
            100                 105                 110
```

<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Tyr Phe Asp Ile Asn Gly Ile Ser Pro Gly Asp Gly Asn Thr Asn Tyr
1               5                   10                  15

Asn Glu Asn Phe Lys Gly Asp Gly Asn Phe Pro Tyr Tyr Ala Met Asp
            20                  25                  30

Ser
```

<210> SEQ ID NO 33
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Tyr Phe Asp Ile Asn Gly Ile Ser Pro Gly Asp Gly Asn Thr Asn Tyr
1               5                   10                  15

Asn Glu Asn Phe Lys Gly Asp Gly Asn Phe Pro Tyr Tyr Ala Met Asp
            20                  25                  30

Ser
```

<210> SEQ ID NO 34
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (17)..(17)

<223> OTHER INFORMATION: G, A, V, L, I, or P
<220> FEATURE:
<221> NAME/KEY: MOD_RES
<222> LOCATION: (18)..(18)
<223> OTHER INFORMATION: S, T, N, or Q
<220> FEATURE:
<221> NAME/KEY: MOD_RES
<222> LOCATION: (19)..(19)
<223> OTHER INFORMATION: H, K, or R
<220> FEATURE:
<221> NAME/KEY: MOD_RES
<222> LOCATION: (21)..(21)
<223> OTHER INFORMATION: S, T, N, or Q

<400> SEQUENCE: 34

```
Tyr Phe Asp Ile Asn Gly Ile Ser Pro Gly Asp Gly Asn Thr Asn Tyr
1               5                   10                  15

Xaa Xaa Xaa Phe Xaa Gly Asp Gly Asn Phe Pro Tyr Tyr Ala Met Asp
            20                  25                  30

Ser
```

<210> SEQ ID NO 35
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (14)..(14)
<223> OTHER INFORMATION: G, A, V, L, I, or P
<220> FEATURE:
<221> NAME/KEY: MOD_RES
<222> LOCATION: (17)..(17)
<223> OTHER INFORMATION: G, A, V, L, I, or P
<220> FEATURE:
<221> NAME/KEY: MOD_RES
<222> LOCATION: (18)..(18)
<223> OTHER INFORMATION: S, T, N, or Q
<220> FEATURE:
<221> NAME/KEY: MOD_RES
<222> LOCATION: (19)..(19)
<223> OTHER INFORMATION: H, K, or R
<220> FEATURE:
<221> NAME/KEY: MOD_RES
<222> LOCATION: (21)..(21)
<223> OTHER INFORMATION: S, T, N, or Q

<400> SEQUENCE: 35

```
Tyr Phe Asp Ile Asn Gly Ile Ser Pro Gly Asp Gly Asn Xaa Asn Tyr
1               5                   10                  15

Xaa Xaa Xaa Phe Xaa Gly Asp Gly Asn Phe Pro Tyr Tyr Ala Met Asp
            20                  25                  30

Ser
```

<210> SEQ ID NO 36
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (12)..(12)
<223> OTHER INFORMATION: S, T, N, or Q
<220> FEATURE:
<221> NAME/KEY: MOD_RES
<222> LOCATION: (14)..(14)
<223> OTHER INFORMATION: G, A, V, L, I, or P
<220> FEATURE:
<221> NAME/KEY: MOD_RES
<222> LOCATION: (17)..(17)
<223> OTHER INFORMATION: G, A, V, L, I, or P
<220> FEATURE:
<221> NAME/KEY: MOD_RES
<222> LOCATION: (18)..(18)
<223> OTHER INFORMATION: S, T, N, or Q
<220> FEATURE:
<221> NAME/KEY: MOD_RES
<222> LOCATION: (19)..(19)
<223> OTHER INFORMATION: H, K, or R
<220> FEATURE:
<221> NAME/KEY: MOD_RES
<222> LOCATION: (21)..(21)
<223> OTHER INFORMATION: S, T, N, or Q

<400> SEQUENCE: 36

Tyr Phe Asp Ile Asn Gly Ile Ser Pro Gly Asp Xaa Asn Xaa Asn Tyr
1 5 10 15

Xaa Xaa Xaa Phe Xaa Gly Asp Gly Asn Phe Pro Tyr Tyr Ala Met Asp
20 25 30

Ser

<210> SEQ ID NO 37
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Arg Ser Ser Gln Ser Leu Val His Ser Asn Gly Asn Thr Tyr Leu His
1 5 10 15

Thr Val Ser Asn Arg Phe Ser Ser Gln Ser Thr His Val Pro Thr
20 25 30

<210> SEQ ID NO 38
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Arg Ser Ser Gln Ser Leu Val His Ser Asn Gly Asn Thr Tyr Leu His
1 5 10 15

Thr Val Ser Asn Arg Phe Ser Ser Gln Ser Thr His Val Pro Thr
20 25 30

<210> SEQ ID NO 39
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(12)
<223> OTHER INFORMATION: S, T, N, or Q

<400> SEQUENCE: 39

Arg Ser Ser Gln Ser Leu Val His Ser Asn Gly Xaa Thr Tyr Leu His
1 5 10 15

```
Thr Val Ser Asn Arg Phe Ser Ser Gln Ser Thr His Val Pro Thr
            20                  25                  30


<210> SEQ ID NO 40
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: S, T, N, or Q
<220> FEATURE:
<221> NAME/KEY: MOD_RES
<222> LOCATION: (12)..(12)
<223> OTHER INFORMATION: S, T, N, or Q

<400> SEQUENCE: 40

Arg Ser Ser Gln Ser Leu Val His Ser Xaa Gly Xaa Thr Tyr Leu His
1               5                   10                  15

Thr Val Ser Asn Arg Phe Ser Ser Gln Ser Thr His Val Pro Thr
            20                  25                  30


<210> SEQ ID NO 41
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: S, T, N, or Q
<220> FEATURE:
<221> NAME/KEY: MOD_RES
<222> LOCATION: (12)..(12)
<223> OTHER INFORMATION: S, T, N, or Q
<220> FEATURE:
<221> NAME/KEY: MOD_RES
<222> LOCATION: (22)..(22)
<223> OTHER INFORMATION: G, A, V, L, I, or P

<400> SEQUENCE: 41

Arg Ser Ser Gln Ser Leu Val His Ser Xaa Gly Xaa Thr Tyr Leu His
1               5                   10                  15

Thr Val Ser Asn Arg Xaa Ser Ser Gln Ser Thr His Val Pro Thr
            20                  25                  30


<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Phe Asp Met Asn
1               5


<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 43

Tyr Phe Asp Met His
1 5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Gly Ile Ser Pro Gly Asp Gly Asn Thr Asn Tyr Asn Gln Asn Phe Lys
1 5 10 15

Gly

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Gly Ile Ser Pro Gly Asp Gly Asn Thr Asn Tyr Asn Gln Lys Phe Gln
1 5 10 15

Gly

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Trp Ile Ser Pro Gly Asp Gly Asn Thr Asn Tyr Ala Gln Lys Phe Gln
1 5 10 15

Gly

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Gly Ile Ser Pro Gly Asp Gly Asn Thr Asn Tyr Asn Gln Lys Phe Gln
1 5 10 15

Gly

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Gly Ile Ser Pro Gly Asp Gly Asn Thr Asn Tyr Ala Gln Lys Phe Gln
1 5 10 15

Gly

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (12)..(12)
<223> OTHER INFORMATION: G, A, V, L, I, or P
<220> FEATURE:
<221> NAME/KEY: MOD_RES
<222> LOCATION: (13)..(13)
<223> OTHER INFORMATION: S, T, N, or Q
<220> FEATURE:
<221> NAME/KEY: MOD_RES
<222> LOCATION: (14)..(14)
<223> OTHER INFORMATION: H, K, or R
<220> FEATURE:
<221> NAME/KEY: MOD_RES
<222> LOCATION: (16)..(16)
<223> OTHER INFORMATION: S, T, N, or Q

<400> SEQUENCE: 49

Gly Ile Ser Pro Gly Asp Gly Asn Thr Asn Tyr Xaa Xaa Xaa Phe Xaa
1 5 10 15

Gly

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (9)..(9)
<223> OTHER INFORMATION: G, A, V, L, I, or P
<220> FEATURE:
<221> NAME/KEY: MOD_RES
<222> LOCATION: (12)..(12)
<223> OTHER INFORMATION: G, A, V, L, I, or P
<220> FEATURE:
<221> NAME/KEY: MOD_RES
<222> LOCATION: (13)..(13)
<223> OTHER INFORMATION: S, T, N, or Q
<220> FEATURE:
<221> NAME/KEY: MOD_RES
<222> LOCATION: (14)..(14)
<223> OTHER INFORMATION: H, K, or R
<220> FEATURE:
<221> NAME/KEY: MOD_RES
<222> LOCATION: (16)..(16)
<223> OTHER INFORMATION: S, T, N, or Q

<400> SEQUENCE: 50

Gly Ile Ser Pro Gly Asp Gly Asn Xaa Asn Tyr Xaa Xaa Xaa Phe Xaa
1 5 10 15

Gly

<210> SEQ ID NO 51
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: S, T, N, or Q
<220> FEATURE:
<221> NAME/KEY: MOD_RES
<222> LOCATION: (9)..(9)
<223> OTHER INFORMATION: G, A, V, L, I, or P
<220> FEATURE:
<221> NAME/KEY: MOD_RES
<222> LOCATION: (12)..(12)
<223> OTHER INFORMATION: G, A, V, L, I, or P
<220> FEATURE:
<221> NAME/KEY: MOD_RES
<222> LOCATION: (13)..(13)
<223> OTHER INFORMATION: S, T, N, or Q
<220> FEATURE:
<221> NAME/KEY: MOD_RES
<222> LOCATION: (14)..(14)
<223> OTHER INFORMATION: H, K, or R
<220> FEATURE:
<221> NAME/KEY: MOD_RES
<222> LOCATION: (16)..(16)
<223> OTHER INFORMATION: S, T, N, or Q

<400> SEQUENCE: 51

Gly Ile Ser Pro Gly Asp Xaa Asn Xaa Asn Tyr Xaa Xaa Xaa Phe Xaa
1               5                   10                  15

Gly


<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Ser Gln Ser Leu Val His Ser Asn Gly Asn Thr Tyr Leu Asn
1               5                   10                  15


<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: S, T, N, or Q

<400> SEQUENCE: 53

Arg Ser Ser Gln Ser Leu Val His Ser Asn Gly Xaa Thr Tyr Leu His
1               5                   10                  15


<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
```

-continued

```
<223> OTHER INFORMATION: S, T, N, or Q
<220> FEATURE:
<221> NAME/KEY: MOD_RES
<222> LOCATION: (12)..(12)
<223> OTHER INFORMATION: S, T, N, or Q

<400> SEQUENCE: 54

Arg Ser Ser Gln Ser Leu Val His Ser Xaa Gly Xaa Thr Tyr Leu His
1               5                   10                  15


<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Val Ser Asn Arg Phe Asp
1               5


<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: G, A, V, L, I, or P

<400> SEQUENCE: 56

Thr Val Ser Asn Arg Xaa Ser
1               5
```